United States Patent
Gennaro et al.

(10) Patent No.: US 7,595,383 B1
(45) Date of Patent: Sep. 29, 2009

(54) **SECRETED PROTEINS OF *MYCOBACTERIUM TUBERCULOSIS* AND THEIR USE AS VACCINES AND DIAGNOSTIC REAGENTS**

(75) Inventors: Maria Laura Gennaro, New York, NY (US); Manuel J. Gomez, Madrid (ES)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 10/009,384

(22) PCT Filed: May 4, 2000

(86) PCT No.: PCT/US00/12197

§ 371 (c)(1),
(2), (4) Date: Aug. 20, 2002

(87) PCT Pub. No.: WO00/66143

PCT Pub. Date: Nov. 9, 2000

(51) Int. Cl.
*C07H 21/04* (2006.01)
*C07H 21/02* (2006.01)
*A61K 39/04* (2006.01)

(52) U.S. Cl. .............. 536/23.7; 424/185.1; 424/190.1; 424/234.1; 424/248.1; 435/69.1; 435/263.1; 435/863; 530/300; 530/350; 536/23.1

(58) Field of Classification Search .............. 424/185.1, 424/190.1, 234.1, 248.1; 435/69.1, 263.1, 435/863; 530/300, 350; 536/23.1, 23.7
See application file for complete search history.

(56) References Cited

U.S. PATENT DOCUMENTS 5,108,745 A * 4/1992 Horwitz .................. 424/234.1
5,736,365 A * 4/1998 Walker et al. ............. 435/91.2

FOREIGN PATENT DOCUMENTS

WO      WO99/09186      *   2/1999

OTHER PUBLICATIONS

Ulmer, J.B., "Tuberculosis vaccines", Scand. J. Infect. Dis., vol. 33, pp. 246-248, 2001.*
Baldwin, S.L., et al, "Evaluation of new vaccines in the mouse and guinea pig model of tuberculosis." Infection and Immunity, vol. 66, No. 6, pp. 2951-2959, 1998.*
Manca et al. (1997) Infection and Immunity 65(12):4951-4957.
Manca et al. (1997) Infection and Immunity 65(1):16-23.
Gennaro et al. (1995) J. of Cell. Biochem. Suppl. Abs. No. B3-112, p 68.
Andersen et al. (1991) Infection and Immunity 59(6):1905-1910.
Borremans et al. (1989) Infection and Immunity 57(10):3123-3130.
Content et al. (1991) Infection and Immunity 59(9):3205-3212.
Horwitz et al. (1995) Proc. Natl. Acad. Sci. USA 92:1530-1534.
Roberts et al. (1995) Immunology 85:502-508.
Matsumoto et al. (1995) Scand. J. Immunol. 41:281-287.
Laqueyrerie et al. (1995) Infection and Immunity 63(10):4003-4010.
Young D. B. et al., Mycobacterial protein antigens: a compilation, Molecular Microbiology (1992) 6(2), 133-145.

* cited by examiner

*Primary Examiner*—Rodney P. Swartz
(74) *Attorney, Agent, or Firm*—Lowenstein Sandler PC

(57) ABSTRACT

The invention provides *mycobacterium tuberculosis* polypeptides and genes encoding them for use in diagnostic and prophylactic methodologies.

8 Claims, 24 Drawing Sheets

FIG. 1

MTSP1
MNRIVQFGVSAVAAAAIGIGAGSGIAAAFDGEDEVTGPDADRARAAAVQAVPGGTAGEVE
TETGEGAAAYGVLVTRPDGTRVEVHLDRDFRVLDTEPADGDGG*

MTSP2
MRLSLTALSAGVGAVAMSLTVGAGVASADPVDAVINTTCNYGQVVAALNATDPGAAAQFN
ASPVAQSYLRNFLAAPPPQRAAMAAQLQAVPGAAQYIGLVESVAGSCNNY*

MTSP3
MFTGIASHAGALGAALVVLIGAAILHDGPAAADPNQDDRFLALLEKKEIPAVANVPRVID
AAHKVCRKLDGGMPVNDIVDGLRNDAYNIDPVMRLYPVRLTTTMTRFISAAVEIYCPNHH
SKMAFAMANFEPGSNEPTHRVAASTRSAVNSGSDLRASVSDMTIMSPGWREPTGAMLASV
LGAVRAGDPLIPNPPPIPVPPPAAQTLIPPPPIVAPPPPRPAPPQQPPPPPPEVEPPAGV
PQSGGAAGSGGAGSGGGGGDGPVEPSPARPMPPGFIRLAP*

MTSP4
MTRLIPGCTLVGLMLTLLPAPTSAAGSNTATTLFPVDEVTQLETHTFLDCHPNGSCDFVA
GANLRTPDGPTGFPPGLWARQTTEIRSTNRLAYLDAHATSQFERVMKAGGSDVITTVYFG
EGPPDKYQTTGVIDSTNWSTGQPMTDVNVIVCTHMQVVYPGVNLTSPSTCAQANFS*

MTSP5
MVLRSRKSTLGVVVCLALVLGGPLNGCSSSASHRGPLNAMGSPAIPSTAQEIPNPLRGQY
EDLMEPLFPQGNPAQQRYPPWPASYDASLRVSWRQLQPTDPRTLPPDAPDDRKYDFSVID
NALTRLADRGMRLTLRVYAYSSCCKASYPDGTNIAIPDWERAIASTNTSYPGPATDPSTG
VVQVVPNFNDSTYLNDFAQLLAALGRRYDGDERLSVFEFSGYGDFSENHVAYLRDTLGAP
GPGPDESVATLGYYSQFRDQNITTASIKQLIAANVSAFPHTQLVTSPANPEIVRELFADE
VTNKLAAPVGVRSDCLGVDAPLPAWAESSTSHYVQTKDPVVAALRQRLATAPVITEWCEL
PTGSSPRAYYEKGLRDVIRYHVSMTSSVNFPDQTATSPMDPALYLVWAQANAAAGYRYSV
EAQPGSQALAGKVATISVTWTNYGAAAATEKWVPGYRLVDSTGQVVRTLPAAVDLKTLVS
DQRGDRSSDQPTPASVAETVRVDLSGLPAGHYTLRAAIDWQQHKPNGSHVVNYPPMLLSR
DGRDDSGFYPVATLDIPRDAQTAVNAS*

MTSP6
MSRLLALLCAAVCTGCVAVVLAPVSLAVVNPWFANSVGNATQVVSVVGTGGSTAKMDVYQ
RTAAGWQPLKTGITTHIGSAGMAPEAKSGYPATPMGVYSLDSAFGTAPNPGGGLPYTQVG
PNHWWSGDDNSPTFNSMQVCQKSQCPFSTADSENLQIPQYKHSVVMGVNKAKVPGKGSAF
FFHTTDGGPTAGCVAIDDATLVQIIRWLRPGAVIAIAK*

MTSP7
MIRELVTTAAITGAAIGGAPVAGADPQRYDGDVPGMNYDASLGAPCSSWERFIFGRGPSG
QAEACHFPPPNQFPPAETGYWVISYPLYGVQQVGAPCPKPQAAAQSPDGLPMLCLGARGW
QPGWFTGAGFFPPEP*

FIG. 1 (continued)

MTSP8
MGELRLVGGVLRVLVVVGAVFDVAVLNAGAASADGPVQLKSRLGDVCLDAPSGSWFSPLV
INPCNGTDFQRWNLTDDRQVESVAFPGECVNIGNALWARLQPCVNWISQHWTVQPDGLVK
SDLDACLTVLGGPDPGTWVSTRWCDPNAPDQQWDSVP*

MTSP9
MPAMTARSVVLSVLLGAHPAWATASELIQLTADFGIKETTLRVALTRMVGAGDLVRSADG
YRLSDRLLARQRRQDEAMRPRTRAWHGNWHMLIVTSIGTDARTRAALRTCMHHKRFGELR
EGVWMRPDNLDLDLESDVAARVRMLTARDEAPADLAGQLWDLSGWTEAGHRLLGDMAAAT
DMPGRFVVAAAMVRHLLTDPMLPAELLPADWPGAGLRAAYHDFATAMAKRRDATQLLEVT
*

MTSP10
VPAGVGNASGSVLDMTSVRTVPSAVALVTFAGAALSGVIPAIARADPVGHQVTYTVTTTS
DLMANIRYMSADPPSMAAFNADSSKYMITLHTPIAGGQPLVYTATLANPSQWAIVTASGG
LRVNPEFHCEIVVDGQVVVSQDGGSGVQCSTRPW*

MTSP11
MTTSKIATAFKTATFALAAGAVALGLASPADAAAGTMYGDPAAAAKYWRQQTYDDCVLMS
AADVIGQVTGREPSERAIIKVAQSTPSVVHPGSIYTKPADAEHPNSGMGTSVADIPTLLA
HYGVDAVITDEDHATATGVATGMAALEQYLGSGHAVIVSINAEMIWGQPVEETDSAGNPR
SDHAVVVTGVDTENGIVHLNDSGTPTGRDEQIPMETFVEAWATSHDFMAVTT*

MTSP12
MGVIARVVGVAACGLSLAVLAAAPTAGAEPTGALPPMTSSGSGPVIGDGDAALRQRISQQ
LFSFGDPTVQEVDGSDAAQFITAAAAVADRDVASVFLPLQRVLGCQQNTAGSGAGFGARA
YRRTDGQWGGAMLVVAKSTVSDVDALKACVKSGWRKATAGTPTSMCNNGWTYPPFADTRR
GEEGYFVLLAGTASDFCSAPNANYRTTASSWPG*

MTSP13
MRLKPAPSPAAAFAVAGLILAGWAGSVGLAGADPEPAPTPKTAIDSDGTYAVGIDIAPGT
YSSAGPVGDGTCYWKRMGNPDGALIDNALSKKPQVVTIEPTDKAFKTHGCQPWQNTGSEG
AAPAGVPGPEAGAQLQNQLGILNGLLGPTGGRVPQP*

MTSP14
MITNLRRRTAMAAAGLGAALGLGILLVPTVDAHLANGSMSEVMMSEIAGLPIPPIIHYGA
IAYAPSGASGKAWHQRTPARAEQVALEKCGDKTCKVVSRFTRCGAVAYNGSKYQGGTGLT
RRAAEDDAVNRLEGGRIVNWACN*

MTSP15
VTVLLDANVLIALVVAEHVHHDAAADWLMASDTGFATCPMTQGSLVRFLVRSGQSAAAAR
DVVSAVQCTSRHEFWPDALSFAGVEVAGVVGHRQVTDAYLAQLARSHDGQLATLDSGLAH
LHGDVAVLIPTTT*

FIG. 1 (continued)

MTSP16
VQRQSLMPQQTLAAGVFVGALLCGVVTAAVPPHARADVVAYLVNVTVRPGYNFANADAAL
SYGHGLCEKVSRGRPYAQIIADVKADFDTRDQYQASYLLSQAVNELCPALIWQLRNSAVD
NRRSG*

MTSP17
VRSYLLRIELADRPGSLGSLAVALGSVGADILSLDVVERGNGYAIDDLVVELPPGAMPDT
LITAAEALNGVRVDSVRPHTGLLEAHRELELLDHVAAAEGATARLQVLVNEAPRVLRVSW
CTVLRSSGGELHRLAGSPGAPETRANSAPWLPIERAAALDGGADWVPQAWRDMDTTMVAA
PLGDTHTAVVLGRPGPEFRPSEVARLGYLAGIVATMLR*

MTSP18
MPDGEQSQPPAQEDAEDDSRPDAAEAAAAEPKSSAGPMFSTYGIASTLLGVLSVAAVVLG
AMIWSAHRDDSGERTYLTRVMLTAAEWTAVLINMNADNIDASLQRLHDGTVGQLNTDFDA
VVQPYRQVVEKLRTHSSGRIEAVAIDTVHRELDTQSGAARPVVTTKLPPFATRTDSVLLV
ATSVSENAGAKPQTVHWNLRLDVSDVDGKLMISRLESIR*

MTSP19
MKMVKSIAAGLTAAAAIGAAAAGVTSIMAGGPVVYQMQPVVFGAPLPLDPASAPDVPTAA
QLTSLLNSLADPNVSFANKGSLVEGGIGGTEARIADHKLKKAAEHGDLPLSFSVTNIQPA
AAGSATADVSVSGPKLSSPVTQNVTFVNQGGWMLSRASAMELLQAAGN*

MTSP20
MNLRRHQTLTLRLLAASAGILSAAAFAAPAQANPVDDAFIAALNNAGVNYGDPVDAKALG
QSVCPILAEPGGSFNTAVASVVARAQGMSQDMAQTFTSIAISMYCPSVMADVASGNLPAL
PDMPGLPGS*

MTSP21
MRVVSTLLSIPLMIGLAVPAHAGPSGDDAVFLASLERAGITYSHPDQAIASGKAVCALVE
SGESGLQVVNELRTRNPGFSMDGCCKFAAISAHVYCPHQITKTSVSAK*

MTSP22
MARTLALRASAGLVAGMAMAAITLAPGARAETGEQFPGDGVFLVGTDIAPGTYRTEGPSN
PLILVFGRVSELSTCSWSTHSAPEVSNENIVDTNTSMGPMSVVIPPTVAAFQTHNCKLWM
RIS*

MTSP23
MLSPLSPRIIAAFTTAVGAAAIGLAVATAGTAGANTKDEAFIAQMESIGVTFSSPQVATQ
QAQLVCKKLASGETGTEIAEEVLSQTNLTTKQAAYFVVDATKAYCPQYASQLT*

FIG. 1 (continued)

MTSP24
MTTMITLRRRFAVAVAGVATAAATTVTLAPAPANAADVYGAIAYSGNGSWGRSWDYPTRA
AAEATAVKSCGYSDCKVLTSFTACGAVAANDRAYQGGVGPTLAAAMKDALTKLGGGYIDT
WACN*

MTSP25
MTPGLLTTAGAGRPRDRCARIVCTVFIETAVVATMFVALLGLSTISSKADDIDWDAIAQC
ESGGNWAANTGNGLYGGLQISQATWDSNGGVGSPAAASPQQQIEVADNIMKTQGPGAWPK
CSSCSQGDAPLGSLTHILTFLAAETGGCSGSRDD*

MTSP26
VQGAVAGLVFLAVLVIFAIIVVAKSVALIPQAEAAVIERLGRYSRTVSGQLTLLVPFIDR
VRARVDLRERVVSFPPQPVITEDNLTLNIDTVVYFQVTVPQAAVYEISNYIVGVEQLTTT
TLRNVVGGMTLEQTLTSRDQINAQLRGVLDEATGRWGLRVARVELRSIDPPPSIQASMEK
QMKADREKRAMILTAEGTREAAIKQAEGQKQAQILAAEGAKQAAILAAEADRQSRMLRAQ
GERAAAYLQAQGQAKAIEKTFAAIKAGRPTPEMLAYQYLQTLPEMARGDANKVWVVPSDF
NAALQGFTRLLGKPGEDGVFRFEPSPVEDQPKHAADGDDAEVAGWFSTDTDPSIARAVAT
AEAIARKPVEGSLGTPPRLTQ*

MTSP27
LQTAHRRFAAAFAAVLLAVVCLPANTAAADDKLPLGGGAGIVVNGDTMCTLTTIGHDKNG
DLIGFTSAHCGGPGAQIAAEGAENAGPVGIMVAGNDGLDYAVIKFDPAKVTPVAVFNGFA
INGIGPDPSFGQIACKQGRTTGNSCGVTWGPGESPGTLVMQVCGGPGDSGAPVTVDNLLV
GMIHGAFSDNLPSCITKYIPLHTPAVVMSINADLADINAKNRPGAGFVPVPA*

MTSP28
MLMPEMDRRRMMMMAGFGALAAALPAPTAWADPSRPAAPAGPTPAPAAPAAATGGLLFHD
EFDGPAGSVPDPSKWQVSNHRTPIKNPVGFDRPQFFGQYRDSRQNVFLDGNSNLVLRATR
EGNRYFGGLVHGLWRGGIGTTWEARIKFNCLAPGMWPAWWLSNDDPGRSGEIDLIEWYGN
GTWPSGTTVHANPDGTAFETCPIGVDGGWHNWRVTWNPSGMYFWLDYADGIEPYFSVPAT
GIEDLNEPIREWPFNDPGYKVFPVLNLAVGGSGGGDPATGSYPQEMLVDWVRVF*

MTSP29
VHRRTALKLPLLLAAGTVLGQAPRAAAEEPGRWSADRAHRWYQAHGWLVGANYITSNAIN
QLEMFQPGTYDPRRIDNELGLARFHGFNTVRVFLHDLLWAQDAPGFQTRLAQFVAIAARY
HIKPLFVLFDSCWDPLPRPGRQRAPRAGVHNSGWVQSPGAERLDDRRYASTLYNYVTGVL
GQFRNDDRVLGWDLWNEPDNPARVYRKVERKDKLERVAELLPQVFRWARTVDPVQPLTSG
VWQGNWGDPGRRSTISAIQLDNADVITFHSYAAPAEFEGRIAELAPLQRPILCTEYLARS
QGSTVEGILPIAKRHNVGAFNWGLVAGKTQTYLPWDSWDHPYRAPPKVWFHDLLHPNGRP
YRDGEVQTIRKLNGMPSQD*

MTSP30
VSTYGWRAYALPVLMVLTTVVVYQTVTGTSTPRPAAAQTVRDSPAIGVVGTAILDAPPRG
LAVFDANLPAGTLPDGGPFTEAGDKTWRVVPGTTPQVGQGTVKVFRYTVEIENGLDPTMY
GGDNAFAQMVDQTLTNPKGWTHNPQFAFVRIDSGKPDFRISLVSPTTVRGGCGYEFRLET
SCYNPSFGGMDRQSRVFINEARWVRGAVPFEGDVGSYRQYVINHEVGHAIGYLRHEPCDQ
QGGLAPVMMQQTFSTSNDDAAKFDPDFVKADGKTCRFNPWPYPIP*

FIG. 1 (continued)

MTSP31
MRPYYIAIVGSGPSAFFAAASLLKAADTTEDLDMAVDMLEMLPTPWGLVRSGVAPDHPKI
KSISKQFEKTAEDPRFRFFGNVVVGEHVQPGELSERYDAVIYAVGAQSDRMLNIPGEDLP
GSIAAVDFVGWYNAHPHFEQVSPDLSGARAVVIGNGNVALDVARILLTDPDVLARTDIAD
HALESLRPRGIQEVVIVGRRGPLQAAFTTLELRELADLDGVDVVIDPAELDGITDEDAAA
VGKVCKQNIKVLRGYADREPRPGHRRMVFRFLTSPIEIKGKRKVERIVLGRNELVSDGSG
RVAAKDTGEREELPAQLVVRSVGYRGVPTPGLPFDDQSGTIPNVGGRINGSPNEYVVGWI
KRGPTGVIGTNKKDAQDTVDTLIKNLGNAKEGAECKSFPEDHADQVADWLAARQPKLVTS
AHWQVIDAFERAAGEPHGRPRVKLASLAELLRIGLG*

MTSP32
VTNPPWTVDVVVVGAGFAGLAAARELTRQGHEVLVFEGRDRVGGRSLTGRVAGVPADMGG
SFIGPTQDAVLALATELGIPTTPTHRDGRNVIQWRGSARSYRGTIPKLSLTGLIDIGRLR
WQFERIARGVPVAAPWDARRARELDDVSLGEWLRLVRATSSSRNLMAIMTRVTWGCEPDD
VSMLHAARYVRAAGGLDRLLDVKNGAQQDRVPGGTQQIAQAAAAQLGARVLLNAAVRRID
RHGAGVTVTSDQGQAEAGFVIVAIPPAHRVAIEFDPPLPPEYQQLAHHWPQGRLSKAYAA
YSTPFWRASGYSGQALSDEAPVFITFDVSPHADGPGILMGFVDARGFDSLPIEERRRDAL
RCFASLFGDEALDPLDYVDYRWGTEEFAPGGPTAAVPPGSWTKYGHWLREPVGPIHWAST
ETADEWTGYFDGAVRSGQRAAAEVAALL*

MTSP33
MKGTKLAVVVGMTVAAVSLAAPAQADDYDAPFNNTIHRFGIYGPQDYNAWLAKISCERLS
RGVDGDAYKSATFLQRNLPRGTTQGQAFQFLGAAIDHYCPEHVGVLQRAGTR*

MTSP34
MKALVAVSAVAVVALLGVSSAQADPEADPGAGEANYGGPPSSPRLVDHTEWAQWGSLPSL
RVYPSQVGRTASRRLGMAAADAAWAEVLALSPEADTAGMRAQFICHWQYAEIRQPGKPSW
NLEPWRPVVDDSEMLASGCNPGSPEESF*

MTSP35
MSGRHRKPTTSNVSVAKIAFTGAVLGGGGIAMAAQATAATDGEWDQVARCESGGNWSINT
GNGYLGGLQFTQSTWAAHGGGEFAPSAQLASREQQIAVGERVLATQGRGAWPVCGRGLSN
ATPREVLPASAAMDAPLDAAAVNGEPAPLAPPPADPAPPVELAANDLPAPLGEPLPAAPA
DPAPPADLAPPAPADVAPPVELAVNDLPAPLGEPLPAAPADPAPPADLAPPAPADLAPPA
PADLAPPAPADLAPPVELAVNDLPAPLGEPLPAAPAELAPPADLAPASADLAPPAPADLA
PPAPAELAPPAPADLAPPAAVNEQTAPGDQPATAPGGPVGLATDLELPEPDPQPADAPPP
GDVTEAPAETPQVSNIAYTKKLWQAIRAQDVCGNDALDSLAQPYVIG*

MTSP36
MSGHRKKAMLALAAASLAATLAPNAVAAAEPSWNGQYLVTLSANAKTGTSMAANRPEYPH
KANYTFSSRCASDVCIATVVDAPPPKNEFIPRPIEYTWNGTQWVREISWQWDCLLPDGTI
EYAPAKSITAYTPGQYGILTGVFHTDIASGTCKGNVDMPVSAKPIVG*

FIG. 1 (continued)

MTSP37
MRYLIATAVLVAVVLVGWPAAGAPPSCAGLGGTVQAGQICHVHASGPKYMLDMTFPVDYP
DQQALTDYITQNRDGFVNVAQGSPLRDQPYQMDATSEQHSSGQPPQATRSVVLKFFQDLG
GAHPSTWYKAFNYNLATSQPITFDTLFVPGTTPLDSIYPIVQRELARQTGFGAAILPSTG
LDPAHYQNFAITDDSLIFYFAQGELLPSFVGACQAQVPRSAIPPLAI*

MTSP38
LKNARTTLIAAAIAGTLVTTSPAGIANADDAGLDPNAAAGPDAVGFDPNLPPAPDAAPVD
TPPAPEDAGFDPNLPPPLAPDFLSPPAEEAPPVPVAYSVNWDAIAQCESGGNWSINTGNG
YYGGLRFTAGTWRANGGSGSAANASREEQIRVAENVLRSQGIRAWPVCGRRG*

MTSP39
MSTIFDIRSLRLPKLSAKVVVVGGLVVVLAVVAAAAGARLYRKLTTTTVVAYFSEALALY
PGDKVQIMGVRVGSIDKIEPAGDKMRVTLHYSNKYQVPATATASILNPSLVASRTIQLSP
PYTGGPVLQDGAVIPIERTQVPVEWDQLRDSINGILRQLGPTERQPKGPFGDLIESAADN
LAGKGRQLNETLNSLSQALTALNEGRGDFVAITRSLALFVSALYQNDQQFVALNENLAEF
TDWFTKSDHDLADTVERIDDVLGTVRKFVSDNRSVLAADVNNLADATTTLVQPEPRDGLE
TALHVLPTYASNFNNLYYPLHSSLVGQFVFPNFANPIQLICSAIQAGSRLGYQESAELCA
QYLAPVLDALKFNYLPFGSNPFSSAATLPKEVAYSEERLRPPPGYKDTTVPGIFSRDTPF
SHGNHEPGWVVAPGMQGMQVQPFTANMLTPESLAELLGGPDIAPPPPGTNLPGPPNAYDE
SNPLPPPWYPQPASLPAAGATGQPGPGQ*

MTSP40
MKRSMKSGSFAIGLAMMLAPMVAAPGLAAADPATRPVDYQQITDVVIARGLSQRGVPFSW
AGGGISGPTRGTGTGINTVGFDASGLIQYAYAGAGLKLPRSSGQMYKVGQKVLPQQARKG
DLIFYGPEGTQSVALYLGKGQMLEVGDVVQVSPVRTNGMTPYLVRVLGTQPTPVQQAPVQ
PAPVQQAPVQQAPVQQAPVQQAPVQQAPVQQAPVQPPPFGTARSR*

MTSP41
MFTRRFAASMVGTTLTAATLGLAALGFAGTASASSTDEAFLAQLQADGITPPSAARAIKD
AHAVCDALDEGHSAKAVIKAVAKATGLSAKGAKTFAVDAASAYCPQYVTSS*

MTSP42
MAAMWRRRPLSSALLSFGLLLGGLPLAAPPLAGATEEPGAGQTPGAPVVAPQQSWNSCRE
FIADTSEIRTARCATVSVPVDYDQPGGTQAKLAVIRVPATGQRFGALLVNPGGPGASAVD
MVAAMAPAIADTDILRHFDLVGFDPRGVGHSTPALRCRTDAEFDAYRRDPMADYSPAGVT
HVEQVYRQLAQDCVDRMGFSFLANIGTASVARDMDMVRQALGDDQINYLGYSYGTELGTA
YLERFGTHVRAMVLDGAIDPAVSPIEESISQMAGFQTAFNDYAADCARSPACPLGTDSAQ
WVNRYHALVDPLVQKPGKTSDPRGLSYADATTGTINALYSPQRWKYLTSGLLGLQRGSDA
GDLLVLADDYDGRDADGHYSNDQDAFNAVRCVDAPTPADPAAWVAADQRIRQVAPFLSYG
QFTGSAPRDLCALWPVPATSTPHPAAPAGAGKVVVVSTTHDPATPYQSGVDLARQLGAPL
ITFDGTQHTAVFDGNQCVDSAVMHYFLDGTLPPTSLRCAP*

FIG. 1 (continued)

MTSP43
MKTGTATTRRRLLAVLIALALPGAAVALLAEPSATGASDPCAASEVARTVGSVAKSMGDY
LDSHPETNQVMTAVLQQQVGPGSVASLKAHFEANPKVASDLHALSQPLTDLSTRCSLPIS
GLQAIGLMQAVQGARR*

MTSP44
MSRLSSILRAGAAFLVLGIAAATFPQSAAADSTEDFPIPRRMIATTCDAEQYLAAVRDTS
PVYYQRYMIDFNNHANLQQATINKAHWFFSLSPAERRDYSEHFYNGDPLTFAWVNHMKIF
FNNKGVVAKGTEVCNGYPAGDMSVWNWA*

MTSP45
VTKRTITPMTSMGDLLGPEPILLPGDSDAEAELLANESPSIVAAAHPSASVAWAVLAEGA
LADDKTVTAYAYARTGYHRGLDQLRRHGWKGFGPVPYSHQPNRGFLRCVAALARAAAAIG
ETDEYGRCLDLLDDCDPAARPALGL*

MTSP46
VIIPDINLLLYAVITGFPQHRRAHAWWQDTVNGHTRIGLTYPALFGFLRIATSARVLAAP
LPTADAIAYVREWLSQPNVDLLTAGPRHLDIALGLLDKLGTASHLTTDVQLAAYGIEYDA
EIHSSDTDFARFADLKWTDPLRE*

MTSP47
LTDPRHTVRIAVGATALGVSALGATLPACSAHSGPGSPPSAPSAPAAATVMVEGHTHTIS
GVVECRTSPAVRTATPSESGTQTTRVNAHDDSASVTLSLSDSTPPDVNGFGISLKIGSVD
YQMPYQPVQSPTQVEATRQGKSYTLTGTGHAVIPGQTGMRELPFGVHVTCP*

FIG. 2 mtsp1
atgaatcgcatcgtgcagttcggagtttcgccgtggccgcggcggcgat
cggcatcggagccgggtcggggatcgcggcggcgttcgacggcgaggacg
aggtgaccggccccgacgccgaccgcgcgcgccgccgcggtgcaggcg
gtcccgggcggcaccgccggagaagtcgagaccgagaccggcgaaggcgc
cgccgcctacggcgtgctggtcacccggcccgacggcacccgtgtcgagg
tccacctggaccgggatttccgggttctggacaccgaaccggccgacggg
gacggcggttag mtsp2
atgaggctgtcgttgaccgcattgagcgccggtgtaggcgccgtggcaat
gtcgttgaccgtcggggccggggtcgcctccgcagatcccgtggacgcgg
tcattaacaccacctgcaattacgggcaggtagtagctgcgctcaacgcg
acggatccgggggctgccgcacagttcaacgcctcaccggtggcgcagtc
ctatttgcgcaatttcctcgccgcaccgccacctcagcgcgctgccatgg
ccgcgcaattgcaagctgtgccggggcggcacagtacatcggccttgtc
gagtcggttgccggctcctgcaacaactattaa mtsp3
atgttcaccggcatcgctagccatgccggcgccctgggtgccgccttagt
ggtgctgatcggcgccgcaattctgcacgacggcccagcagcggccgacc
caaaccaagacgatcggtttctggcgctgctcgagaaaaaggaaatcccc
gccgtcgcgaatgtgcctcgcgtcatcgacgcggcccacaaagtgtgtcg
caaactcgatggcggcatgccggtaacgacattgtggacgggttacgca
acgatgcctacaacatagacccggtcatgcgcctctaccctgtccgcctc
acgacgaccatgacccgatttatcagtgcggcagtggagatctactgccc
gaaccatcacagcaagatggcgttcgccatggccaatttcgagccgggat
cgaatgaaccgacgcatcgcgttgcggcgtccacgcgcagcgcggtcaac
tcgggaagcgacctgcgggcgtcggtgtcggacatgaccatcatgtcgcc
gggatggcgggaaccgacgggtgcgatgcttgcctcggtgctcggagcgg
ttcgcgcggggatcccctgataccgaatccgccgccgattccggtaccg
ccgccggcggcgcagaccctgattccaccccgccgatcgtggcaccgcc
gccaccgcgaccagcgccgccgcaacagccgccgccccgccgccagagg
ttgagccgcctgctggtgttccgcagtccgggggcgctgccggcagtggc
ggcgccggcagcggtggtggcggcggtggtgacggaccggtagagccgtc
gcctgcacgacccatgccgccgggctttatcaggctcgcgccgtga mtsp4
atgacgcggctgataccggggttgcacgctcgtcgggctgatgctgacgtt
actgccgcgcccacctcggcggccgggagcaacaccgccaccaccctgt
tcccggtcgacgaggtcacccagctggagacgcacaccttcctcgattgc
cacccaacggcagctgcgacttcgtcgctggagcaaatctgcgcacacc
cgacggcccgacgggctttccgcccgggctgtgggcgcgccaaaccaccg
agatccgttcgacgaaccggttggcctatctggacgcgcacgccaccagc
cagttcgaacgggtaatgaaggcgggcggatccgacgtgatcaccaccgt
ctacttcggcgagggtccgccggacaaataccagaccaccggggtcatcg
actcgaccaattggtcgaccggtcaaccgatgaccgacgtcaacgtcatc
gtgtgtacacacatgcaggtggtctacccgggggtcaacctcacctcgcc
cagcacctgcgcgcaagccaacttttcctag

FIG. 2 (continued)

mtsp5
atggttttaagaagtaggaaaagcacgctcggcgttgtcgtgtgcttagc
gctggtgctcggtgggccgctaacggttgcagcagcagcgcgagccacc
gcggtccactgaacgcaatgggaagtccggccataccgtcgacggcgcag
gagatacccaacccgttgcgcggtcagtacgaagacctcatggaaccgct
gtttccgcaggggaaccccgcgcagcaacgctatccgccttggcccgcgt
cctacgacgcgagtttgcgagtctcctggcggcagctgcagcctacggat
ccgcgcactctgccccggatgctccggacgaccgcaagtacgacttcag
cgtgatcgacaacgcgttgaccaggctcgccgaccgcggcatgcggctga
cgctgcgggtgtacgcctacagctcgtgctgcaaggcttcctatccggac
ggcactaacatcgcgattcccgactgggagcgcgctatcgccagcaccaa
caccagttatccagggccggcgaccgatccctcgaccggggtggtgcagg
tggtgccgaatttcaacgattcgacctatcttaacgattttgcgcagttg
ctcgccgcgcttggtcgccgctacgacggtgacgagcgcctcagcgtgtt
cgagttctccgggtacggggacttcagcgaaaatacgtcgcatacctgc
gcgacacgctcggtgcgccgggtccgggcccggatgaaagcgtggcgacc
ctgggctattacagccagttccgtgatcagaacatcaccaccgcgtccat
caaacagctaatcgcggcgaacgtcagcgcctcccgcatacccaactgg
tgaccagtcccgctaatccggaaatcgtgcgagaactgttcgccgacgag
gtcaccaacaagcttgccgcgccggtgggtgtccgctcggattgcctggg
cgtcgacgcgccgttgccggcctgggccgagtccagcacttcgcactatg
tgcagaccaaagacccggtggtcgccgcgctgcggcagcggctggcaacg
gcgccggtgatcaccgagtggtgcgagttgccgaccggcagttcgccgcg
ggcttactacgagaagggcctgcgcgacgtcatcaggtatcacgtgtcga
tgacgtcgagcgttaacttccccgaccagacggcgacctcgccgatggac
cccgcgttgtacctggtgtgggcgcaagctaacgccgccgcaggctatcg
gtactcggtcgaagcgcagccggggtcgcaagcgctagcgggcaaggtcg
cgacgatctcggtcacctggaccaactacggcgctgctgccgccaccgaa
aagtgggtgcccggctaccggctggtggattccaccggacaggtggttcg
gacgctgccggcagcggtggacctgaagacgctggtctccgaccagcgcg
gcgatcgcagcagcgaccagccgacaccggcgtcggtcgccgagacggtt
cgcgttgatctgtccggcttgcccgcgggccactacacgctgcgggccgc
gatcgactggcaacagcacaaaccgaacggctcccatgtggtgaactatc
cgcccatgctgttgtcccgcgacggccgcgacgattccgggttttatccc
gtcgccacgctcgacatcccacgcgacgcgcagaccgcggtcaacgcttc
gtag mtsp6
atgagccgactcctagctttgctgtgcgctgcggtatgcacgggctgcgt
tgctgtggttctcgcgccagtgagcctggccgtcgtcaacccgtggttcg
cgaactcggtcggcaatgccactcaggtggtttcggtggtgggaaccggc
ggttcgacggccaagatggatgtctaccaacgcaccgccgccggctggca
gccgctcaagaccggtatcaccacccatatcggttcggcgggcatggcgc
cggaagccaagagcggatatccggccactccgatggggtttacagcctg
gactccgcttttggcaccgcgccgaatcccggtggcgggttgccgtatac
ccaagtcggacccaatcactggtggagtggcgacgacaatagccccacct
taactccatgcaggtctgtcagaagtcccagtgccgttcagcacggcc
gacagcgagaacctgcaaatcccgcagtacaagcattcggtcgtgatggg
cgtcaacaaggccaaggtcccaggcaaggctccgcgttcttctttcaca
ccaccgacggcgggcccaccgcgggttgtgtggcgatcgacgatgccacg

FIG. 2 (continued)

ctggtgcagatcatccgttggctgcggcctggtgcggtgatcgcgatcgc
caagtaa mtsp7
atgattcgcgaactggtcaccaccgctgcgatcacgggtgccgcgatcgg
tggggcgccagtcgcgggcgcagaccgcagcgttatgacggcgatgtgc
cggggatgaactatgacgcttcgctgggcgcccatgctccagctgggag
cgcttcattttggacgaggcccctccggtcaggccgaagcctgtcattt
tccgcctcctaaccagttcccgccggccgaaaccggctactgggtgatct
cctacccgctatacggcgtccagcaggtcggtgcgccgtgtccgaagccg
caggcggccgcgcagtctccggatgggttgccgatgctgtgtctgggagc
ccgtggatggcagccgggatggtttaccggggccgggttcttccctccgg
agccataa mtsp8
atgggtgaattacggttggtgggcggtgtgctccgggtccttgtcgtggt
cggtgcggtgttcgatgtggcggtgctaaacgccggtgcggctagtgccg
acggcccggtccagctgaagagccgattgggcgatgtttgcctggacgcc
ccgagtgggagctggttcagcccgctggtgatcaaccctgcaatgggac
cgactttcagcgctggaatctcaccgatgaccggcaggtcgagagcgtgg
ccttccccggggaatgcgtgaatatcggaaatgctttgtgggcgcgcctg
cagccctgtgtgaactggatcagccagcactggactgtccagcccgacgg
cctggtcaagagtgatcttgatgcctgcctcacggttctcggcggtccgg
atcctgggacctgggtgtccaccgctggtgcgaccccaatgcacccgac
caacagtgggatagcgtgccgtaa mtsp9
atgccggccatgaccgcccgttcggtggtactcagcgtgctgctcggtgc
tcatcccgcgtgggccaccgcaagcgaattgatccagctgacagcggatt
tcggtatcaaggagacgacgttgcgggtcgcgctgacccgcatggtcggt
gccggggatctggtccggtccgcggacggctaccggctctcggatcggtt
gctggcccgccagcgccgacaagatgaggccatgcgcccacggacccgcg
cttggcacggaaactggcacatgctgattgtcaccagcatcggcaccgat
gctcgtacccgggccgcactgcgaacctgcatgcaccacaagcgtttcgg
tgaattgcgggaaggggtgtggatgcggccggacaatctcgacctcgact
tggagtccgacgttgcggcccgggttaggatgctgacggcccgcgacgag
gccccgccgacttggccgggcagctgtgggatctgtcggggtggaccga
ggccggccaccggttgctcggcgacatggcagcggccaccgacatgcccg
ggcgatttgtggtggctgcggcgatggtgcgccacctgctcaccgatccg
atgttgcccgctgaactgttgcccgccgactggccgggcgccgggttacg
ggcggcgtaccacgacttcgccactgcaatggcgaaacgacgcgatgcaa
ctcaactcctggaggtgacatga mtsp10
gtgccggccggcgtcggtaacgcatccggtagcgttttagatatgacgtc
cgtgcgcacagtgccaagcgccgtcgcgctggtgacgtttgccggagccg

FIG. 2 (continued)

cgctcagcggggtcatcccggcgattgcccgcgcggatccggtcgggcat
caggtgacctacaccgtcacgaccaccagcgacctgatggccaacattcg
gtacatgagcgccgatccgcccagcatggcggctttcaatgccgattcat
cgaagtacatgattaccttgcacactccgatcgctggcggtcagccgctg
gtctataccgccacgctggcaaacccgagccagtgggcgatcgtcaccgc
cagcggcggcctgcgggtcaatccggagttccactgcgagattgttgtag
acggccaggtggtggtgtcgcaggacggcggcagcggcgtgcagtgctcg
actcgtccctggtaa mtsp11
atgacgaccagcaaaatcgccaccgccttcaagaccgccaccttcgcgct
ggccgccggtgccgttgcactgggattggccagccccgccgacgcagcgg
cgggcaccatgtatggcgacccggcagccgccgccaagtactggcgccag
cagacatacgacgactgcgtcctgatgtcggccgcggacgtgatcggtca
agtgaccggcagggagccttccgagcgcgccatcatcaaagtggcccagt
cgacacccagcgtcgtgcaccccgggtccatctacacaaagccggccgac
gccgagcacccgaactcgggaatgggtaccagcgtggccgacataccgac
gctgctggcgcattacggcgtcgacgccgttatcaccgacgaggaccacg
ccacagccaccggagtcgccaccggcatggccgccctcgagcagtatctg
ggcagcgggcacgccgtgatcgtcagcatcaacgccgagtgatctgggg
ccagcccgtcgaggaaaccgacagtgccggcaacccgcggtctgaccacg
ccgtggtggtgaccggtgtcgataccgaaaacggcattgttcacctcaac
gacagcggtaccccacgggccgcgacgagcagatcccgatggaaacctt
cgtcgaggcgtgggccaccagccacgacttcatggccgtcaccacctga mtsp12
atgggagtcattgcccgcgttgtcggtgtcgccgcgtgcggtttgtccct
ggccgtgctggccgccgcgcccaccgcgggcgcggaacccaccggcgcgc
tgccccgatgacatccagcggcagcggaccggtcatcggcgacggtgac
gccgcgctgcgacagcggatctcacagcagctgtttagcttcggagatcc
caccgtccaggaggttgacggctcggacgcggctcaattcatcacggccg
cagccgctgtcgcggaccgcgatgtggcgtcggtgttcttgccgctgcag
cgggtgttgggctgccaacagaacacagccggctcggggccggcttcgg
ggcgcgcctaccggcgaaccgacgggcaatggggaggcgcgatgctgg
tcgtcgccaagagcaccgtttccgacgtcgacgccctcaaggcctgcgtc
aagtccggttggcgcaaggccacggcgggcacgccgacttcgatgtgcaa
caacggttggacctacccgccgttcgccgacacccgccgcggcgaagagg
gctatttcgtcttgctggccggcacggcctcggacttctgcagtgcgccc
aacgcgaactaccgaaccaccgcgagctcatggccgggctag mtsp13
atgcgcttgaagccagccccatctcctgctgcagcctttgccgtcgccgg
cctgatcctcgcaggctgggccggatccgtgggcctcgccggcgccgatc
cggagccggcaccgacaccgaagacggcaattgatagcgacggcacctat
gcggtggggattgacatcgctcccggcacgtacagctccgcgggacccgt
cggcgacggcacctgctattggaagcggatgggtaaccccgatggcgcgc
tcatcgataacgcactcagcaagaaaccacaggtagtgacgattgagccg
accgacaaggcgttcaagacgcacggctgccaaccctggcagaacacggg
cagcgaaggcgctgccctgccggagttcctggacctgaagcgggggccc

FIG. 2 (continued)

aactacaaaatcagctcggcatcctcaacggcttactcggaccgactgga
gggcgagtgcctcagccctaa mtsp14
atgatcacaaacctccgacgccgaaccgcgatggcagccgccggcctagg
ggctgctctcgggctgggcatcctgctggttccgacggtggacgcccatc
tcgccaacggttcgatgtcggaagtcatgatgtcggaaattgccgggttg
cctatccctccgattatccattacggggcgattgcctatgccccagcgg
cgcgtcgggcaaagcgtggcaccagcgcacaccggcgcgagcagagcaag
tcgcactagaaaagtgcggtgacaagacttgcaaagtggttagtcgcttc
accaggtgcggcgcggtcgcctacaacggctcgaataccaaggcggaac
cggactcacgcgccgcgcggcagaagacgacgccgtgaaccgactcgaag
gcgggcggatcgtcaactgggcgtgcaactaa mtsp15
gtgacggtgctgctcgacgccaacgtgctgatcgcattggtggtcgccga
gcatgtgcatcatgatgccgcagcggactggctcatggcgtccgacaccg
gatttgcgacctgcccgatgacacaaggaagcctggttcgattcctggtg
cgctcgggacagtccgcggcggcggctcgggatgtcgtcagtgcggtcca
gtgcacgagccgccacgaattctggcccgatgcactctctttcgccggtg
tcgaggtcgctggtgtggttgggcaccggcaggtgaccgatgcctacctt
gcccagctcgcgcgaagccacgacgggcagttggcgacgctcgacagcgg
cttagcacacctgcacggcgacgtcgcggtactcattccaacgaccacct
ga mtsp16
gtgcagcgccaatcattgatgccccagcagacccttgccgccggcgtttt
cgtgggtgcgctgctatgcggtgtcgtgacggcggcggtgccaccacacg
cacgcgccgacgtggtcgcctatctggtcaacgtgacggtacgcccgggc
tacaacttcgccaacgccgacgccgcgttgagttacggacatggcctctg
cgagaaggtgtctcggggccgcccttacgcacagatcatcgccgacgtca
aggctgatttcgacacccgcgaccaataccaggcctcgtatctgctcagc
caggctgtcaacgaactctgccccgcgctgatctggcagttgcgaaactc
cgcagtcgacaatcggcgctcgggctga mtsp17
gtgcgttcgtatctattgcgtatcgagctggccgaccggccgggcagcct
tgggtcgctggcggtcgcgctcggctcggtgggcgccgacatcctctcgc
tcgacgtggtcgagcgcggcaacggctatgcgatcgacgacctggtggtc
gaactgccccgggagcgatgcccgacacgctgatcactgctgccgaggc
gctgaacggcgtccgggtagacagcgtccgcccgcacaccggcctgttgg
aagcccaccgcgagctggaactgctcgatcatgtggccgcggctgagggc
gcgaccgcacggctccaggttctggtcaacgaggccccccgggtgctccg
ggtgagctggtgcacggtgttgcgcagttccggcggggagctgcaccgtc
tggccggcagccaggtgcgccggagacccgggccaattcggcgccctgg
ctgccgatcgagcgggccgcggcgctggacggcggcgccgactgggtgcc
gcaagcctggcgcgacatggataccaccatggtcgcggctccattgggtg
acacgcacaccgcggtggtgctgggcaggccaggcccggaatttcgcccg

FIG. 2 (continued)

tcggaggtggcgcggttgggttatctagccggcatcgtggcgacgatgct
gcgctga mtsp18
atgcctgacggggagcagagccagccaccggcccaagaagatgcggaaga
cgactcgcggcccgacgccgcggaggccgccgcggccgaacccaaatcat
cagccggtccgatgttctcgacctacgtatcgcctcgacactactcggc
gtgctatcggtcgccgcggtcgtgctgggtgcgatgatctggtccgcaca
ccgcgatgactccggcgagcgtacctacctgacccgggtcatgctgaccg
ccgctgaatggacggccgtgctgatcaacatgaacgccgacaacatcgat
gccagcctgcagcgactgcacgacggaacggtcggtcaactcaacaccga
cttcgacgctgtcgtgcagccctaccggcaggtggtggagaagttgcgga
cgcacagcagcggcaggatcgaggcggtagcgatcgatacggtgcaccgc
gagctggatacccagtccggtgccgcccgaccggtagtaaccacgaaatt
gccaccgtttgccactcgcaccgactcggtgctgctggtcgcgacgtcgg
tcagtgagaacgccggcgccaaaccccagaccgtgcactggaacttgcgg
ctcgatgtctccgatgtggacggcaagctgatgatctcccggttggagtc
gattcgatga mtsp19
atgaagatggtgaaatcgatcgccgcaggtctgaccgccgcggctgcaat
cggcgccgctgcggccggtgtgacttcgatcatggctggcggccggtcg
tataccagatgcagccggtcgtcttcggcgcgccactgccgttggacccg
gcatccgcccctgacgtcccgaccgccgcccagttgaccagcctgctcaa
cagcctcgccgatcccaacgtgtcgtttgcgaacaagggcagtctggtcg
agggcggcatcgggggcaccgaggcgcgcatcgccgaccacaagctgaag
aaggccgccgagcacggggatctgccgctgtcgttcagcgtgacgaacat
ccagccggcggccgccggttcggccaccgccgacgtttccgtctcgggtc
cgaagctctcgtcgccggtcacgcagaacgtcacgttcgtgaatcaaggc
ggctggatgctgtcacgcgcatcggcgatggagttgctgcaggccgcagg
gaactga mtsp20
atgaacctacggcgccatcagaccctgacgctgcgactgctggcggcatc
cgcgggcattctcagcgccgcggccttcgccgcgccagcacaggcaaacc
ccgtcgacgacgcgttcatcgccgcgctgaacaatgccggcgtcaactac
ggcgatccggtcgacgccaaagcgctgggtcagtccgtctgcccgatcct
ggccgagcccggcgggtcgtttaacaccgcggtagccagcgttgtggcgc
gcgcccaaggcatgtcccaggacatggcgcaaaccttcaccagtatcgcg
atttcgatgtactgcccctcggtgatggcagacgtcgccagcggcaacct
gccggccctgccagacatgccggggctgcccgggtcctag mtsp21
atgagagttgtgtcaacgctactcagcattccgttgatgatcggcttggc
ggttccggcccacgcggggcccagcggtgacgacgcggtctttcttgcct
cgctagagcgggcaggcattacctacagccacccggatcaagccatagca
tcgggcaaggccgtatgcgcgttagtcgaaagcggcgaatcgggtcttca
ggtcgtcaacgagctgcggacccgcaatcccgggttttcgatggacggtt
gttgcaagttcgctgcgatctccgcgcatgtctattgcccccaccagatc
actaaaaccagcgtcagcgcgaaatag

FIG. 2 (continued)

mtsp22
atggcccgcacgcttgcgttgcgcgcatcggcgggactcgtcgcgggtat
ggcaatggccgcgatcacgctcgcacctggggcccgcgccgaaaccggtg
agcaattccccggggatggggtgtttctcgtgggaactgacattgcgcca
ggcacctaccgcacggaggggccgtcgaatccccttatttggtgttcgg
cagggtgtccgagctctcaacctgctcatggtcgacacacagcgcaccg
aggtgagcaatgagaacattgtcgacaccaacacctctatgggcccgatg
tcagtggtgatcccgccgaccgtggcagccttccagacgcataactgcaa
gctttggatgcggatctcatag mtsp23
atgttatcgccgttatcgcctcgcattatcgcagcgttcaccactgcagt
cggcgccgccgccatcggacttgccgtcgccaccgccggcaccgccggcg
ccaacaccaaagacgaagccttcattgctcagatggagtccattggcgtc
accttctcctcaccgcaggtggccacccagcaagcccagctggtctgcaa
gaagctggccagcggcgaaaccggcaccgagatcgccgaggaggtcctca
gccaaaccaacctgaccactaagcaggcagcctacttcgtcgtcgacgca
accaaggcctactgcccgcaatacgccagccagctcacctag mtsp24
atgacgacgatgattactcttcggcgacggttcgcggtggccgtcgccgg
cgtcgccactgccgccgcgacgaccgtcacctggctcccgcaccagcaa
atgccgccgatgtctatggcgcaattgcctactccggcaacggctcgtgg
ggccgatcgtgggactacccaacccgggcggctgccgaagccaccgccgt
caagtcgtgtggctactccgactgcaaggtgctcaccagtttcaccgcct
gcggcgccgtcgccgccaacgatagggcataccagggaggagttggaccc
accttggccgccgccatgaaggacgccctgaccaagctcggcggcggcta
catcgacacctgggcctgcaactaa mtsp25
atgacaccgggtttgcttactactgcgggtgctggccgaccacgtgacag
gtgcgccaggatcgtatgcacggtgttcatcgaaaccgccgttgtcgcga
ccatgtttgtcgcgttgttgggtctgtccaccatcagctcgaaagccgac
gacatcgattgggacgccatcgcgcaatgcgaatccggcggcaattgggc
ggccaacaccggtaacgggttatacggtggtctgcagatcagccaggcga
cgtgggattccaacggtggtgtcgggtcgccggcggccgcgagtccccag
caacagatcgaggtcgcagacaacattatgaaaacccaaggcccgggtgc
gtggccgaaatgtagttcttgtagtcagggagacgcaccgctgggctcgc
tcacccacatcctgacgttcctcgcggccgagactggaggttgttcgggg
agcagggacgattga mtsp26
gtgcaaggagccgttgctggtctggtgtttctggccgtcctggtgattt
cgccatcatcgtggtggccaagtcggtggcgctgatcccgcaggcggagg
ccgcggtgatcgagcggctgggtcgctatagtcgtacggtcagtgggcag
ttgacgctgttggtgccgttcatcgaccgcgtccgggctcgggtggacct
gcgcgagcgggtggtgtcgtttccgccgcaaccggtgatcaccgaggaca
acttgacgctgaacatcgacaccgtcgtctacttccaggtgaccgttccg

FIG. 2 (continued)

```
caggcggcggtgtacgagatcagcaattacatcgtcggggtcgaacagct
caccaccaccaccctgcgcaacgttgtcggcgggatgacgctggagcaga
cgttgacctcgcgtgaccagatcaacgcccagctgcgcggcgttctcgat
gaggcgaccggccgctggggtctgcgggtggcgcgggtggagctgcgcag
catcgatccgccgcgtcgattcaggcgtcgatggaaaagcagatgaagg
ccgaccgggagaagcgagcgatgattctgaccgccgaaggtacccgggag
gcggcgataaaacaggccgaggggcaaaagcaggcgcagatcctggccgc
cgagggcgccaagcaggccgcgatcttggctgctgaggccgatcggcagt
ctcggatgctgcgcgctcagggtgagcgcgccgcggcctacctgcaggcg
caagggcaggccaaggccatcgagaagacgttcgccgcgatcaaggctgg
ccggcccaccccggagatgctggcctaccaatacctgcagacgctgccgg
agatggcgcgtggggacgccaacaaggtatgggtggtgcccagcgacttc
aacgccgcactgcaggggttcaccaggctgctgggcaagccgggtgagga
cggggtgttccggttcgagccgtccccggtcgaagaccagcccaagcacg
cggccgacggtgacgacgccgaggtcgccggctggttctccaccgatacc
gacccgtcgatcgctcgggcggtggctacagccgaggcgatagcccgcaa
gccggtcgagggttcgctggggacgcccccaggttgactcaatag
``` mtsp27

```
ttgcagacggcgcacaggcgctttgccgcggcattcgcggccgtgctttt
ggccgttgtgtgcctacctgcgaacaccgcggcagccgacgacaagctac
cgctgggcggtggtgcgggcatcgtcgtcaacggggacaccatgtgcacc
ctaaccaccatcggccatgacaagaacggtgacctcatcggcttcacttc
cgcccactgtggggcccgggcgcgcagatcgccgctgagggtgccgaga
acgcgggcccggtaggcatcatggtcgccggcaacgacggcctggactac
gcggtgatcaagttcgaccgccaaggtgaccccggtggccgtcttcaa
cgggtttgcgatcaacggcattggcccggaccgtcgttcggccagatcg
cctgcaagcagggccgcaccaccggtaactcgtgcggggttacctggggg
ccaggggagagtccgggcaccttgtgatgcaggtctgcggcggaccggg
cgactccggtgcgccggtgaccgtcgacaatctgctggtcgggatgatcc
acggcgcattcagcgacaatctgccgagttgcatcaccaaatacatcccg
ctgcacaccccggcggtggtgatgtcgatcaacgccgacctggccgacat
caacgccaagaaccggccgggcgcgggattcgtcccggtaccggcctga
``` mtsp28

```
atgcttatgcctgagatggatcgtcgccgaatgatgatgatggcggggtt
cggcgccctggctgccgcgcttccgccccgacagcctgggccgacccgt
cccggccggccgcgccggctggtccgacaccggcgcccgccgcgccggct
gcggcaaccggtgggcttttgttccacgacgagttcgacgggccggccgg
ttcggtcccggacccgtccaagtggcaggtgtcgaaccaccggacgccca
tcaagaacccggtgggctttgaccggccccagttttttgggcagtaccgc
gacagtcgacagaacgtgttcctcgacggcaactccaatctcgtgctgcg
cgctacccgagagggcaacaggtatttcggtggcctggtccacggcctgt
ggcggggtggcatcgggaccacctgggaggcccggatcaagttcaactgc
ctggctccgggcatgtggcccgcctggtggttgtccaatgacgatcctgg
tcgcagcggcgaaatcgacctgatcgagtggtatggcaacgggacttgc
cgtcgggaaccaccgtgcacgccaacccggacggcaccgcattcgagacc
tgcccgatcggtgtggacggtggttggcacaactggcgcgtcacgtggaa
tccgagcggcatgtacttctggctggattacgccgacggcattgagccct
acttctcggttccggcgaccggaatcgaagacctcaacgagcccatccgc
```

FIG. 2 (continued)

gagtggccgttcaacgaccccggctacaaggtgtttccggtgttgaacct
tgcggttggcggttctggtggcggcgatcccgcgacgggttcctatccac
aggagatgctcgtcgactgggtgcgcgtcttttaa mtsp29
gtgcaccgtcgaacggccctgaagctcccgctgctgctggcggcaggcac
ggtgctgggccaagcgccgcgggccgccgccgaagaaccaggccggtggt
cggccgaccgcgcacatcgctggtatcaagcgcacggctggctcgtcggt
gcaaactacatcacctcgaacgccatcaaccagctcgagatgttccagcc
aggcacatacgatccccggcgcatcgacaacgagctgggccttgcgcggt
ttcacgggttcaacaccgtgcgagtcttcctccacgacctgctgtgggcc
caagacgcgcccggtttccaaacccggctcgcgcagttcgtcgccatcgc
ggcgcgataccacatcaaaccgctctttgtcctgttcgactcctgctggg
acccgctccccagaccgggtcggcagcgggcgccaagggctggggtgcac
aactccgggtgggtgcaaagtccgggtgctgaacgcctcgatgaccgccg
ctatgccagcacgctgtacaactacgtcacgggtgtgttgggccaattcc
gcaacgacgatcgcgtgttgggttgggacctgtggaatgaacccgacaat
cccgcgcgcgtgtatcgcaaggtggaaaggaaagacaagctcgagcgcgt
cgcggagctcctcccccaagtgttccgatgggcccgcacggtcgatccgg
ttcaaccgctgaccagtggtgtctggcaagggaattggggagatcccgga
cgccgcagcaccatcagcgccattcaactcgacaacgccgacgtgatcac
cttccacagttacgccgcgccggccgaattcgagggccgcatcgctgagc
tcgctccgttgcagcggccaatcctgtgcaccgagtacctggcgcggtcc
caaggcagcactgtcgagggaatcctgccgattgctaagcggcacaacgt
tggtgcgttcaattggggtttggtggcgggaaagactcagacctatttgc
cgtgggattcgtgggatcacccctaccgcgcgccccgaaggtgtggttt
cacgacctgctacaccccaacggccggccgtatcgggacggcgaagttca
aacgattcggaagctgaacgggatgccgagccaggactag mtsp30
gtgtccacgtacggctggcgcgcctacgccctgccggttctgatggtgct
gaccacggtggtggtgtaccagacggtgaccgggacgagcacgccaaggc
ccgcggcggcccagaccgtccgggactcgccggccattggtgtggtgggg
accgcgatcctcgacgcaccgcctcgcggtcttgcagtgttcgatgccaa
tctgccggccgggacgctgccggatggcggcccgttcaccgaggctggtg
acaagacctggcgtgtcgttccgggcactactccccaggtcggtcaaggc
accgtcaaagtgttcaggtataccgtcgagatcgagaacggtcttgatcc
cacaatgtacggcggtgacaacgcattcgcccagatggtcgaccagacgt
tgaccaatcccaagggctggacccacaatccgcaattcgcgttcgtgcgg
atcgacagcggaaaacccgacttccggatttcgctggtgtcgccgacgac
agtgcgcggggggtgtggctacgaattccggctcgagacgtcctgctaca
acccgtcgttcggcggcatggatcgccaatcgcgggtgttcatcaacgag
gcgcgctgggtacgcggagccgttccattcgaaggtgacgtaggttccta
tcggcaatatgtgatcaaccacgaggtcggtcatgccatcggttacctgc
gccacgagccgtgcgaccaacaaggcggtctggctccggtaatgatgcag
cagacgttttccacctccaatgacgacgcggccaagtttgaccccgactt
cgttaaggcggatggaaagacctgccgattcaatccctggccctacccga
ttccctaa

FIG. 2 (continued)

mtsp31
atgcgtccctattacatcgccatcgtgggctccgggccgtcggcgttctt
cgccgcggcatccttgctgaaggccgccgacacgaccgaggacctcgaca
tggccgtcgacatgctggagatgttgccgactccctgggggctggtgcgc
tccggggtcgcgccggatcacccaagatcaagtcgatcagcaagcaatt
cgaaaagacggccgaggaccccgcttccgcttcttcggcaatgtggtcg
tcggcgaacacgtccagcccggcgagctctccgagcgctacgacgccgtg
atctacgccgtcggcgcgcagtccgatcgcatgttgaacatccccggtga
ggacctgccgggcagtatcgccgccgtcgatttcgtcggctggtacaacg
cacatccacacttcgagcaggtatcacccgatctgtcgggcgcccgggcc
gtagttatcggcaatggaaacgtcgcgctagacgtggcacggattctgct
caccgatcccgacgtgttggcacgcaccgatatcgccgatcacgctttgg
aatcgctacgcccacgcggtatccaggaggtggtgatcgtcgggcgccga
ggtccgctgcaggccgcgttcaccacgttggagttgcgcgagctggccga
cctcgacggggttgacgtggtgatcgatccggcggagctggacggcatta
ccgacgaggacgcggccgcggtgggcaaggtctgcaagcagaacatcaag
gtgctgcgtggctatgcggaccgcgaaccccgcccgggacaccgccgcat
ggtgttccggttcttgacctctccgatcgagatcaagggcaagcgcaaag
tggagcggatcgtgctgggccgcaacgagctggtctccgacggcagcggg
cgagtggcggccaaggacaccggcgagcgcgaggagctgccagctcagct
ggtcgtgcggtcggtcggctaccgcggggtgcccacgcccgggctgccgt
tcgacgaccagagcgggaccatccccaacgtcggcggccgaatcaacggc
agccccaacgaatacgtcgtcgggtggatcaagcgcgggccgaccggggt
gatcgggaccaacaagaaggacgcccaagacaccgtcgacaccttgatca
agaatcttggcaacgccaaggagggcgccgagtgcaagagctttccggaa
gatcatgccgaccaggtggccgactggctagcagcacgccagccgaagct
ggtcacgtcggcccactggcaggtgatcgacgctttcgagcgggccgccg
gcgagccgcacgggcgtccccgggtcaagttggccagcctggccgagctg
ttgcggattgggctcggctga mtsp32
gtgacaaacccaccgtggactgtcgatgttgtcgtggtgggcgcgggctt
cgccgggctggccgcggcccgcgagctgacgcgacagggtcacgaggtgc
tggtgttcgaaggccgcgatcgggtgggcggccgctcgttaaccggtcgc
gtggcaggggtgcccgcggatatgggcggctcgttcatcggcccgaccca
agacgccgtgctggcgttggccaccgagctggggatcccgacaaccccga
cccaccgcgacggccgaaacgtcatccagtggcggggatcggcacgcagc
tatcgtggcaccatccccaagctgtcgctgaccgggctcatcgacatcgg
ccggttgcgttggcaattcgagcgaattgcccgcggcgttccggtggccg
ccccctgggatgcgcggcgcgcgcgtgaactcgacgacgtgtcgctcggg
gagtggttgcgcttggtgcgcgccacatcgtcctcgcggaacctgatggc
catcatgacccgggtgacctggggttgtgagcccgacgatgtctcgatgc
tgcacgccgcccgctacgtacgcgcggccggcggcctggaccggctgctc
gacgtcaaaaatggtgcccagcaggaccgtgtgccgggggggacacagca
gatcgcccaggcggccgccgcccaactcggcgcacgcgtcctgctcaacg
ccgcggtgcgtcgcatcgaccggcacggagcgggtgtgacggtcacgtcc
gatcagggtcaggccgaggccgggttcgtcatcgtcgccattccaccggc
ccatcgcgtggccatcgagttcgatccccgctgccgccggaatatcagc
agctcgcccaccattggccgcagggccggctgagcaaggcctacgcggcc
tattcgacgccgttctggcgggccagcgggtattccggccaggcgctgtc
cgatgaggcgccggtgttcatcaccttcgacgtcagtccgcacgccgacg

FIG. 2 (continued)

ggccaggcattctgatggggttcgtcgatgctcgcgggttcgactcgcta
cccatcgaagagcgccgccgcgatgcattgcgctgctttgcgtcgctgtt
cggcgacgaagcgctcgaccccttgattatgttgactatcgttggggta
cagaggaattcgcgccgggtggtccgaccgcggcggtaccgccggggtcg
tggacgaaatacggtcactggttacgtgagccggtcggtccgattcactg
ggcgagcactgagaccgcggacgaatggaccgggtatttcgacggcgccg
tcagatccggtcagcgtgccgccgccgaggtcgccgccctgctatga mtsp33
atgaagggaacaaagctggctgttgtcgtcggcatgacggtggctgccgt
tagtttggcagcgccggcgcaggccgacgactacgacgccccttcaaca
acacgatccatcgcttcgggatctacggcccgcaggactacaacgcttgg
cttgccaagatcagctgcgaacggctgagcagaggcgttgacggcgatgc
gtacaagtcggccactttcctgcaacgcaacctgccgcgcggaaccaccc
agggccaagcgtttcagttcctgggcgccgcgatcgatcactactgccct
gagcatgtgggcgtcctgcaacgggctggcacccgctaa mtsp34
atgaaagccctggtggccgtgtcggcggtggccgtcgtcgcactgctcgg
tgtatcttccgcccaagctgatcccgaggcggatcccggcgcaggtgagg
ccaactatggtggcccccaagttccccacgtcttgtcgatcacaccgaa
tgggcgcagtggggaagtctgcccagcctccgggtctacccgtcccaagt
tgggcgtacagcctcccgccgcctcgggatggccgctgccgacgcggcct
gggccgaggttctcgcgctgtcaccggaggccgacactgccggcatgcgc
gcgcagttcatctgccactggcagtacgccgaaatcagacaacccggcaa
acccagctggaacctcgagccgtggcggccggtcgtcgacgactcggaga
tgttggcttccggctgcaatccgggcagccctgaagagtcgttttag mtsp35
atgagtggacgccaccgtaagcccaccacatccaacgtcagcgtcgccaa
gatcgcctttaccggcgcagtactcggtggcggcggcatcgccatggccg
ctcaggcgaccgcggccaccgacggggaatgggatcaggtggcccgctgc
gagtcgggcggcaactggtcgatcaacaccggcaacggttacctcggtgg
cttgcagttcactcaaagcacctgggccgcacatggtggcggcgagttcg
ccccgtcggctcagctggccagccgggagcagcagattgccgtcggtgag
cgggtgctggccacccagggtcgcggcgcctggccggtgtgcggccgcgg
gttatcgaacgcaacaccccgcgaagtgcttccgcttcggcagcgatgg
acgctccgttggacgcggccgcggtcaacggcgaaccagcaccgctggcc
ccgccgcccgccgacccggcgccaccgtggaacttgccgctaacgacct
gcccgcaccgctgggtgaaccctccggcagctcccgccgacccggcac
cacccgccgacctggcaccacccgcgcccgccgacgtcgcgccacccgtg
gaacttgccgtaaacgacctgcccgcaccgctgggtgaaccctcccggc
agctcccgccgacccggcaccacccgccgacctggcaccacccgcgcccg
ccgacctggcgccacccgcgcccgccgacctggcgccacccgcgcccgcc
gacctggcaccacccgtggaacttgccgtaaacgacctgcccgcgccgct
gggtgaaccctcccggcagctcccgccgaactggcgccacccgccgatc
tggcacccgcgtccgccgacctggcgccacccgcgcccgccgacctggcg
ccacccgcgcccgccgaactggcgccacccgcgcccgccgacctggcacc
acccgctgcggtgaacgagcaaaccgcgccgggcgatcagcccgccacag

FIG. 2 (continued)

ctccaggcggcccggttggccttgccaccgatttggaactccccgagccc
gaccccaaccagctgacgcaccgccgcccggcgacgtcaccgaggcgcc
cgccgaaacgccccaagtctcgaacatcgcctatacgaagaagctgtggc
aggcgattcgggcccaggacgtctgcggcaacgatgcgctggactcgctc
gcacagccgtacgtcatcggctga mtsp36
atgtccggacaccgcaagaaggcaatgctcgccttggcggctgcgtcgct
ggcagcgacgctggccccgaacgcagtcgcggccgcagaaccgtcgtgga
acgggcagtacctcgtgacgttgtctgccaacgcgaaaaccggcaccagc
atggcggccaaccggccagagtatccacacaaagcgaactacacgttcag
ctcgcgctgcgcgtccgatgtctgcattgccaccgtggtcgacgctccgc
caccaaaaaacgagttcatcccgcggccaatcgaatacacctggaatggg
actcaatgggtacgggagatcagctggcaatgggactgcctgctacccga
cggcacaatcgaatatgccccagccaaatcgatcacggcctacacgcccg
gtcagtacggaatcctcaccggcgtctttcataccgatatcgccagcggc
acgtgtaaaggcaatgtcgacatgccagtgtcggccaaaccgatcgttgg
ctga mtsp37
atgcgttatctgatagcgaccgcagtgctcgttgctgtggtcctggtggg
ctggccggcggctggtgcgccgccgtcatgcgccggcctgggcggcactg
tgcaggccggccagatctgccatgtgcacgcctcgggccctaagtacatg
ctggatatgacatttcctgtcgactatcccgaccagcaggcgctgaccga
ctacatcacgcaaaaccgcgacgggttcgtcaacgtcgcgcaggggtccc
cgctgcgagaccagccctaccaaatggacgccaccagcgaacagcacagc
tccggccagccgccgcaggccacccgcagcgtagtgctcaaattcttcca
ggacctcggtggggcacatccgtccacctggtacaaggccttcaactaca
acctcgcgacctcgcagcccatccttcgacacgttgttcgtgcccggc
accacgccactggacagcatctacccatcgttcagcgcgagctggcacg
tcagaccggtttcggtgccgcgatattgccttcgaccggcctcgacccgg
ctcactaccagaactttgctatcaccgacgacagtctgattttctacttc
gcccagggtgagctgctgccgtcgtttgtcggcgcttgccaagcccaggt
gccgcgcagcgccattccgccgctggcaatctaa mtsp38
ttgaagaacgcccgtacgacgctcatcgccgccgcgattgccgggacgtt
ggtgaccacgtcaccagccggtatcgccaatgccgacgacgcgggcttgg
acccaaacgccgcagccggcccggatgccgtgggctttgacccgaacctg
ccgccggccccggacgctgcaccgtcgatactccgccggctccggagga
cgcgggctttgatcccaacctcccccgcgctggccccggacttcctgt
ccccgcctgcggaggaagcgcctccgtgcccgtggcctacagcgtgaac
tgggacgcgatcgcgcagtgcgagtccggtggaaactggtcgatcaacac
cggtaacggttactacggcggcctgcggttcaccgccggcacctggcgtg
ccaacggtggctcggggtccgcggccaacgcgagccgggaggagcagatc
cgggtggctgagaacgtgctgcgttcgcagggtatccgcgcctggccggt
ctgcggccgccgcggctga mtsp39
atgagcaccatcttcgacatccgcagcctgcgactgccgaaactgtctgc
aaaggtagtggtcgtcggcgggttggtggtggtcttggcggtcgtggccg

FIG. 2 (continued)

ctgcggccggcgcgcggctctaccggaaactgactaccactaccgtggtc
gcgtatttctctgaggcgctcgcgctgtacccaggagacaaagtccagat
catgggtgtgcgggtcggttctatcgacaagatcgagccggccggcgaca
agatgcgagtcacgttgcactacagcaacaaataccaggtgccggccacg
gctaccgcgtcgatcctcaaccccagcctggtggcctcgcgcaccatcca
gctgtcaccgccgtacaccggcggcccggtcttgcaagacggcgcggtga
tcccaatcgagcgcacccaggtgcccgtcgagtgggatcagttgcgcgat
tccatcaatgggatcctccgccagctcggcccgacggagcggcagccgaa
ggggccgttcggcgacctcatcgaatcggccgcggacaacctggccggca
agggcaggcagctcaacgaaacgctgaacagtttgtcgcaggcgttgacc
gcgctgaacgagggccggggagacttcgttgcgatcacgcgaagcctggc
gctatttgtcagcgcgctctaccagaatgatcaacagttcgttgcgctca
acgaaaaccttgccgagttcaccgactggttcaccaaatccgaccatgac
ttggccgacacggtggaacggatcgacgacgttctcggcaccgtccgaaa
gttcgtgagcgacaacagatccgtgctggctgccgatgtcaacaacctcg
ccgacgcgaccactacactagtgcaacccgagccgcgggacggtctggaa
accgcgttgcacgtgttgccgacctacgcagcaacttcaacaaccttta
ctatccactgcacagctctctggtgggccagttcgtgttccccaacttcg
cgaacccaattcagctcatttgcagcgctattcaggccggcagccgactc
ggctatcaggaatccgccgagctgtgcgcgcagtacttggcaccggttct
ggacgctctcaagttcaattacttgccgttcggctcaaacccgttcagtt
cggcggccactttgcccaaggaggtggcttactccgaggagcggctccgc
ccgccgcccgggtacaaggacaccactgtcccagggatcttctcgcggga
cacaccgttttcacacggcaaccatgaaccgggctgggtcgttgcgccg
ggatgcagggtatgcaggttcagccgtttaccgcgaacatgctcaccccg
gaatcgctggcagagctgctgggtggtccggatattgccccccgccgcc
gggaaccaacttgcccggaccgccgaatgcgtatgacgagtccaatccgt
tgccgccgccgtggtacccgcagcccgcgtccctcccggctgcgggcgcc
acaggacagccaggcccgggccagtga mtsp40
atgaaacgcagcatgaaaagcggctccttcgcgatcggtctggcaatgat
gctcgccccgatggtggccgcgcccggtcttgcggccgcagacccggcca
cgcggccggtggattatcaacagatcaccgacgtcgtgatcgcgcgcggg
ctgtcgcagcgcggcgtgccgttctcctgggccggcggcggcatcagcgg
ccccacgcgcggcaccggtaccggcatcaacaccgtcgggttcgacgcct
ccggtttgatccagtacgcctatgccggtgccgggctaaagctgccgcgt
tcttccggccagatgtacaaggttgggcaaaaggtcctgccgcagcaagc
gcgcaagggcgacctgatcttctacggccccgaaggcacgcaaagcgtcg
cgttatacctcgggaagggccagatgctggaggtgggcgacgtcgtccag
gtttcgccggtgcgcaccaacggcatgacgccttacctggtccgggttct
cgggacccagccgacgcccgtccaacaggcgccggtccagccagcgccgg
tccagcaagcgcccgtccagcaagcgcccgtccaacaggcgcccgtccaa
caggcgccggtccaacaggcgccggtccagcaagcgcccgtccagcaagc
gcccgtccagccgcctcccttcggcaccgcgcgctcacgctaa mtsp41
atgttcactcgccgtttcgccgcctccatggttggcaccaccttgactgc
cgctactttgggcctggccgcactcggcttcgccgggaccgccagcgcaa
gctcgaccgacgaagcgttcctcgcgcagctgcaggcggacgggatcact

FIG. 2 (continued)

ccgccgagcgcagcgcgcgccatcaaggacgcgcacgccgtctgcgacgc
cctcgacgagggtcactcggccaaagcggtcatcaaggcggtggccaagg
cgaccggtctgagcgccaagggcgccaagacgttcgccgttgacgccgcg
tcggcctactgcccgcagtacgtgacctcgagctaa mtsp42
atggcggccatgtggcgccgcagaccgttgagctcggcgctgctgtccttc
cgggttgctgctcggcggactgccctagcagcgccccgttggccggcg
cgactgaagaacccggcgccggccaaaccccgggtgcgccggtcgtggcg
ccgcaacagagttggaacagctgccgcgagttcatcgccgacaccagcga
aattcgcactgcacgctgcgcgacggtgtccgtccccgtcgactacgacc
aacccggtgggacacaagcgaagttggcggtgatccgcgtccccgcgacg
ggacagcgattcggagcactgctggtcaatcctgggggacccggggcgtc
ggcggtcgacatggtcgccgctatggcacccgcgatcgccgacaccgaca
ttctccgccacttcgacctggtgggcttcgacccgagaggggtcggccac
tcgacccctgcgttgcggtgtcgcaccgacgccgagttcgacgcgtaccg
gcgcgatccgatggccgactacagtccggccggtgtcacccacgtcgaac
aggtctaccggcagttggcccaggactgtgttgaccggatgggcttcagc
ttcttggccaatatcggtaccgcgtccgtcgcacgggacatggacatggt
tcgccaagcgttaggtgacgatcagatcaactacctcggatacagctacg
gcaccgagttgggcaccgcttacctggaacggttcggtactcatgtgcgg
gcgatggtcctcgacggcgctatcgatccagccgttagcccaatcgagga
aagcatcagccaaatggcgggatttcagaccgctttcaatgactacgccg
ccgactgcgcccgctcgccggcctgccctctgggcaccgactcggcccag
tgggtcaaccgctaccacgccctggttgacccgctggtgcagaagccggg
taagacgtcggatccacgtggcctgagctacgccgacgcgacgacgggca
ccatcaacgcgctgtacagccctcagcgctggaagtacctgaccagtggt
ctgctggggctgcagcgcggcagcgacgccggcgacttgctggtgcttgc
cgacgactatgacggccgggatgcagacgggcactacagcaacgaccagg
acgcgttcaacgcggtccggtgcgtcgatgcgcccacaccggccgatcca
gcggcctgggtggccgccgaccaacggatccgtcaggtcgccccgttcct
tagctacgggcagttcaccggatccgcccccgcgatctgtgcgcgctgt
ggccggtgccggcaacgtcgacgccgcaccccgcggcgccggccggggct
ggcaaggtcgtcgtggtgtccaccacccacgacccggccactccgtatca
gtccggggtagacctggcccgccagctgggcgcaccgctgatcaccttcg
acggcacccaacacactgcggtgttcgatggcaaccagtgtgtggactct
gcggtgatgcactattttctcgacgggaccttgccgccgacgagtctgcg
gtgcgcgccctga mtsp43
atgaagacaggcaccgcgacgacgcggcgcaggctgttggcagtactgat
cgccctcgcgttgccgggggccgccgttgcgctgctggccgaaccatcag
cgaccggcgcgtcggacccgtgcgcggccagcgaagtggcgaggacggtc
ggttcggtcgccaagtcgatgggcgactacctggattcacacccagagac
caaccaggtgatgaccgcggtcttgcagcagcaggtagggccggggtcgg
tcgcatcgctgaaggccatttcgaggcgaatcccaaggtcgcatcggat
ctgcacgcgctttcgcaaccgctgaccgatctttcgactcggtgctcgct
gccgatcagcggcctgcaggcgatcggtttgatgcaggcggtgcagggcg
cccgccggtag

FIG. 2 (continued)

mtsp44
atgtctcggctgagttccatcctgcgtgccggcgcggcatttctggttct
cggcatcgccgctgcgacatttccacaaagcgcggcagccgactccacgg
aagactttccaatacctcgccggatgatcgcaaccacctgcgacgccgaa
caatatctggcggcggtgcgggataccagtccggtgtactaccagcggta
catgatcgacttcaacaaccatgcaaaccttcagcaagcgacgatcaaca
aggcgcactggttcttctcgctgtcaccggcggagcgccgagactactcc
gaacacttttacaatggcgatccgctgacgtttgcctgggtcaatcacat
gaaaatcttcttcaacaacaagggcgtcgtcgctaaagggaccgaggtgt
gcaatggatacccagccggcgacatgtcggtgtggaactgggcctaa mtsp45
gtgaccaagcgcacaataactcccatgacgtcgatgggtgatctcttgggacctgagcca
atcctgttgcctggcgacagcgacgccgaagcggagctgcttgccaacgaaagtccgagc
atcgtcgcggccgcgcatccgtcggcgtcggtcgcctgggcggtgctcgccgaaggggcg
ctggccgacgacaagaccgtcacggcctacgcatacgcgcgtaccgggtaccaccgcggc
ctggaccagctgcgccgccatggctggaagggcttcggcccggtgccgtattccaccag
cccaaccggggtttcctacggtgtgtggcggcgctggcgcgcgccgcagccgctatcggc
gagaccgacgagtatggacgctgcctggatctgcttgacgactgtgacccgcggcccgt
ccggcgcttgggctc mtsp46
gtgatcatccctgacatcaatctgctgctctacgcggtcatcaccggattcccgcagcac
cggcgcgcgcatgcgtggtggcaagacaccgtcaacggccacacccgtatcgggctgacg
tatccggcgttgttcgggttcctacggatcgccaccagtgcccgcgtgctcgccgcgcca
ctgccaaccgcggatgcgatcgcctatgtgcgcgagtggctttcgcagccgaacgtggac
ctactcacggcgggtccgcgccacctggacatcgcgttgggcctgctcgacaagctcggc
acagccagccacctaaccaccgatgtgcaactggccgcctacggcatcgaatacgacgcc
gagatccattccagtgacaccgactttgcccgattcgccgatctgaagtggaccgacccg
ttgcgcgaa mtsp47
ttgactgatccgcgccacaccgttcgaatcgctgtcggagctaccgcgctcggcgtgtcg
gcactcggggcaactctgccggcctgctccgcacacagcgggccgggttctcccccagt
gcgccgtcagctcccgcggccgcgaccgtcatggtagagggacatacgcacacaatttcc
ggagtggtcgagtgccgcacctcgccagcggtaaggacggcgacgccgtcggagtcgggg
actcaaactacacgggttaacgcacacgacgattcggcctcggtgacactgtccctgtcc
gactccacgccccagacgtcaatggttttggtatctcccttaaaatcggaagcgtcgac
taccagatgccctaccagccggttcagtccccaactcaggtcgaagcgaccaggcagggc
aagagttacacactgaccgggacgggtcacgcggtgatcccgggccaaaccggcatgcgt
gagctgccgttcggggtacatgtaacctgtccg

SECRETED PROTEINS OF *MYCOBACTERIUM TUBERCULOSIS* AND THEIR USE AS VACCINES AND DIAGNOSTIC REAGENTS

BACKGROUND OF THE INVENTION

The invention is in the field of tuberculosis and, specifically, reagents useful for generating immune responses to *Mycobacterium tuberculosis* and for diagnosing infection and disease in a subject that has been exposed to *M. tuberculosis*.

Tuberculosis infection continues to be a world-wide health problem. This situation has recently been greatly exacerbated by the emergence of multi-drug resistant strains of *M. tuberculosis* and the international AIDS epidemic. It has thus become increasingly important that effective vaccines against and reliable diagnostic reagents for *M. tuberculosis* be produced.

U.S. Pat. No. 6,087,163 is incorporated herein by reference in it entirety.

SUMMARY OF THE INVENTION

The invention is based on the discovery of a novel group of open reading frames (ORFs) encoding polypeptides that are secreted by *M. tuberculosis*. The invention features these polypeptides, functional segments thereof, DNA molecules encoding either the polypeptides or the functional segments, vectors containing the DNA molecules, cells transformed by the vectors, compositions containing one or more of any of the above polypeptides, functional segments, or DNA molecules, and a variety of diagnostic, therapeutic, and prophylactic (vaccine) methodologies utilizing the foregoing.

Specifically, the invention features an isolated DNA molecule containing a DNA sequence encoding a polypeptide with a first amino acid sequence that can be the amino acid sequence of the polypeptide MTSP1, MTSP2, MTSP3, MTSP4, MTSP5, MTSP6, MTSP7, MTSP8, MTSP9, MTSP10, MTSP11, MTSP12, MTSP13, MTSP14, MTSP15, MTSP16, MTSP17, MTSP18, MTSP19, MTSP20, MTSP21, MTSP22, MTSP23, MTSP24, MTSP25, MTSP26, MTSP27, MTSP28, MTSP29, MTSP30, MTSP31, MTSP32, MTSP33, MTSP34, MTSP35, MTSP36, MTSP37, MTSP38, MTSP39, MTSP40, MTSP41, MTSP42, MTSP43, MTSP44, MTSP45, MTSP46, or MTSP47, as depicted in FIG. 1, or a second amino acid sequence identical to the first amino acid sequence with conservative substitutions; the polypeptide has *Mycobacterium tuberculosis* specific antigenic and immunogenic properties. Also included in the invention is an isolated portion of the above DNA molecule. The portion of the DNA molecule encodes a segment of the polypeptide shorter than the full-length polypeptide, and the segment has *Mycobacterium tuberculosis* specific antigenic and immunogenic properties. Other embodiments of the invention are vectors containing the above DNA molecules and transcriptional and translational regulatory sequences operationally linked to the DNA sequence, the regulatory sequences allow for the expression of the polypeptide or functional segment encoded by the DNA sequence in a cell. The invention encompasses cells (e.g., eukaryotic and prokaryotic cells) transformed with the above vectors.

The invention encompasses compositions containing any of the above vectors and a pharmaceutically acceptable diluent or filler. Other compositions to be used as DNA vaccines can contain at least two (e.g., three, four, five, six, seven, eight, nine, then, twelve, fifteen or twenty) DNA sequences, each encoding a polypeptide of the *Mycobacterium tuberculosis* complex or a functional segment thereof, with the DNA sequences being operationally linked to transcriptional and translational regulatory sequences which allow for expression of each of the polypeptides in a cell of a vertebrate. In such compositions, at least one of the DNA sequences contains the sequence of the above DNA molecules of the invention.

The invention also features an isolated polypeptide with a first amino acid sequence that can be the sequence of the polypeptide MTSP1, MTSP2, MTSP3, MTSP4, MTSP5, MTSP6, MTSP7, MTSP8, MTSP9, MTSP10, MTSP11, MTSP12, MTSP13, MTSP14, MTSP15, MTSP16, MTSP17, MTSP18, MTSP19, MTSP20, MTSP21, MTSP22, MTSP23, MTSP24, MTSP25, MTSP26, MTSP27, MTSP28, MTSP29, MTSP30, MTSP31, MTSP32, MTSP33, MTSP34, MTSP35, MTSP36, MTSP37, MTSP38, MTSP39, MTSP40, MTSP41, MTSP42, MTSP43, MTSP44, MTSP45, MTSP46, or MTSP47, as depicted in FIG. 1, or a second amino acid sequence identical to the first amino acid sequence with conservative substitutions. The polypeptide has *Mycobacterium tuberculosis* specific antigenic and immunogenic properties. Also included in the invention is an isolated segment of this polypeptide, the segment being shorter than the full-length polypeptide and having *Mycobacterium tuberculosis* specific antigenic and immunogenic properties. Other embodiments are compositions containing the polypeptide, or functional segment, and a pharmaceutically acceptable diluent or filler. Compositions of the invention can also contain at least two (e.g., three four, five, six, seven, eight, nine, ten, twelve, fifteen, or twenty) polypeptides of the *Mycobacterium tuberculosis* complex, or functional segments thereof, with at least one of the at least two polypeptides having the sequence of one of the above described polypeptides of the invention.

The invention also features methods of diagnosis. One embodiment is a method involving: (a) administration of one of the above polypeptide compositions to a subject suspected of having or being susceptible to *Mycobacterium tuberculosis* infection; and (b) detecting an immune response in the subject to the composition, as an indication that the subject has or is susceptible to *Mycobacterium tuberculosis* infection. Another embodiment is a method that involves: (a) providing a population of cells containing CD4 T lymphocytes from a subject; (b) providing a population of cells containing antigen presenting cells (APC) expressing a major histocompatibility complex (MHC) class II molecule expressed by the subject; (c) contacting the CD4 lymphocytes of (a) with the APC of (b) in the presence of one or more of the polypeptides, functional segments, and or polypeptide compositions of the invention; and (d) determining the ability of the CD4 lymphocytes to respond to the polypeptide, as an indication that the subject has or is susceptible to *Mycobacterium tuberculosis* infection. Another diagnostic method of the invention involves: (a) contacting a polypeptide, a functional segment, or a polypeptide/functional segment composition of the invention with a bodily fluid of a subject; (b) detecting the presence of binding of antibody to the polypeptide, functional segment, or polypeptide/functional segment composition, as an indication that the subject has or is susceptible to *Mycobacterium tuberculosis* infection.

Also encompassed by the invention are methods of vaccination. These methods involve administration of any of the above polypeptides, functional segments, or DNA compositions to a subject. The compositions can be administered alone or with one or more of the other compositions.

As used herein, an "isolated DNA molecule" is a DNA which is one or both of: not immediately contiguous with one or both of the coding sequences with which it is immediately contiguous (i.e., one at the 5' end and one at the 3' end) in the naturally-occurring genome of the organism from which the DNA is derived; or which is substantially free of DNA sequence with which it occurs in the organism from which the DNA is derived. The term includes, for example, a recombinant DNA which incorporated into a vector, e.g., into an autonomously replicating plasmid or virus, or into the genomic DNA of a prokaryote or eukaryote, or which exists as a separate molecule (e.g., a cDNA or a genomic fragment produced by PCR or restriction endonuclease treatment) independent of other DNA sequences. Isolated DNA also includes a recombinant DNA which is part of a hybrid DNA encoding additional *M. tuberculosis* polypeptide sequences.

"DNA molecules" include cDNA, genomic DNA, and synthetic (e.g., chemically synthesized) DNA. Where single-stranded, the DNA molecule may be a sense strand or an antisense strand.

An "isolated polypeptide" of the invention is a polypeptide which either has no naturally-occurring counterpart, or has been separated or purified from components which naturally accompany it, e.g., in *M. tuberculosis* bacteria. Typically, the polypeptide is considered "isolated" when it is at least 70%, by dry weight, free from the proteins and naturally-occurring organic molecules with which it is naturally associated. Preferably, a preparation of a polypeptide of the invention is at least 80%, more preferably at least 90%, and most preferably at least 99%, by dry weight, the peptide of the invention. Since a polypeptide that is chemically synthesized is, by its nature, separated from the components that naturally accompany it, the synthetic polypeptide is "isolated."

An isolated polypeptide of the invention can be obtained, for example, by extraction from a natural source (e.g., *M. tuberculosis* bacteria); by expression of a recombinant nucleic acid encoding the polypeptide; or by chemical synthesis. A polypeptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

The polypeptides may contain a primary amino acid sequence that has been modified from those disclosed herein. Preferably these modifications consist of conservative amino acid substitutions. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

The terms "protein" and "polypeptide" are used herein to describe any chain of amino acids, regardless of length or post-translational modification (for example, glycosylation or phosphorylation). Thus, the term "Mycobacterium tuberculosis polypeptide" includes full-length, naturally occurring *Mycobacterium tuberculosis* protein, as well a recombinantly or synthetically produced polypeptide that corresponds to a full-length naturally occurring *Mycobacterium tuberculosis* protein or to particular domains or portions of a naturally occurring protein. The term also encompasses a mature *Mycobacterium tuberculosis* polypeptide which has an added amino-terminal methionine (useful for expression in prokaryotic cells).

As used herein, "immunogenic" means capable of activating a primary or memory immune response. Immune responses include responses of CD4+ and CD8+ T lymphocytes and B-lymphocytes. In the case of T lymphocytes, such responses can be proliferative, and/or cytokine (e.g., interleukin(IL)-2, IL-3, IL-4, IL-5, IL-6, IL-12, IL-13, IL-15, tumor necrosis factor-α (TNF-α), or interferon-γ (IFN-γ))-producing, or they can result in generation of cytotoxic T-lymphocytes (CTL). B-lymphocyte responses can be those resulting in antibody production by the responding B lymphocytes.

As used herein, "antigenic" means capable of being recognized by either antibody molecules or antigen-specific T cell receptors (TCR) on activated effector T cells (e.g., cytokine-producing T cells or CTL).

Thus, polypeptides that have "*Mycobacterium tuberculosis* specific antigenic properties" are polypeptides that: (a) can be recognized by and bind to antibodies elicited in response to *Mycobacterium tuberculosis* organisms or wild-type *Mycobacterium tuberculosis* molecules (e.g., polypeptides); or (b) contain subsequences which, subsequent to processing of the polypeptide by appropriate antigen presenting cells (APC) and bound to appropriate major histocompatibility complex (MHC) molecules, are recognized by and bind to TCR on effector T cells elicited in response to *Mycobacterium tuberculosis* organisms or wild-type *Mycobacterium tuberculosis* molecules (e.g., polypeptides).

As used herein, polypeptides that have "*Mycobacterium tuberculosis* specific immunogenic properties" are polypeptides that: (a) can elicit the production of antibodies that recognize and bind to *Mycobacterium tuberculosis* organisms or wild-type *Mycobacterium tuberculosis* molecules (e.g., polypeptides); or (b) contain subsequences which, subsequent to processing of the polypeptide by appropriate antigen presenting cells (APC) and bound to appropriate major histocompatibility complex (MHC) molecules on the surface of the APC, activate T cells with TCR that recognize and bind to peptide fragments derived by processing by APC of *Mycobacterium tuberculosis* organisms or wild-type *Mycobacterium tuberculosis* molecules (e.g., polypeptides) and bound to MHC molecules on the surface of the APC. The immune responses elicited in response to the immunogenic polypeptides are preferably protective. As used herein, "protective" means preventing establishment of an infection or onset of a disease or lessening the severity of a disease existing in a subject. "Preventing" can include delaying onset, as well as partially or completely blocking progress of the disease.

As used herein, a "functional segment of a *Mycobacterium tuberculosis* polypeptide" is a segment of the polypeptide that has *Mycobacterium tuberculosis* specific antigenic and immunogenic properties.

Where a polypeptide, functional segment of a polypeptide, or a mixture of polypeptides and/or functional segments have been administered (e.g., by intradermal injection) to a subject for the purpose of testing for a *M. tuberculosis* infection or susceptibility to such an infection, "detecting an immune response" means examining the subject for signs of a immunological reaction to the administered material, e.g., reddening or swelling of the skin at the site of an intradermal injection. Where the subject has antibodies to the administered material, the response will generally be rapid, e.g., 1 minute to 24 hours. On the other hand, a memory or activated T cell reaction of pre-immunized T lymphocytes in the subject is generally slower, appearing only after 24 hours and being maximal at 24-96 hours.

As used herein, a "subject" can be a human subject or a non-human mammal such as a non-human primate, a horse, a bovine animal, a pig, a sheep, a goat, a dog, a cat, a rabbit, a guinea pig, a hamster, a rat, or a mouse.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. Unless otherwise indicated, these materials and methods are illustrative only and are not intended to be limiting. All publications, patent applications, patents and other references mentioned herein are illustrative only and not intended to be limiting.

Other features and advantages of the invention, e.g., methods of diagnosing or vaccinating against *M. tuberculosis* infection, will be apparent from the following description, from the drawings and from the claims.

BRIEF DESCRIPTION OF THE DRAWINGS

FIG. 1 is a depiction of the amino acid sequences of *M. tuberculosis* polypeptides MTSP1-MTSP47 (SEQ ID NOs: 1-47, respectively).

FIG. 2 is a depiction of the nucleotide sequences of the coding regions (mtsp 1-mtsp47) encoding MTSP1-MTSP47 (SEQ ID NOs:48-94, respectively).

DETAILED DESCRIPTION

Figure 3:
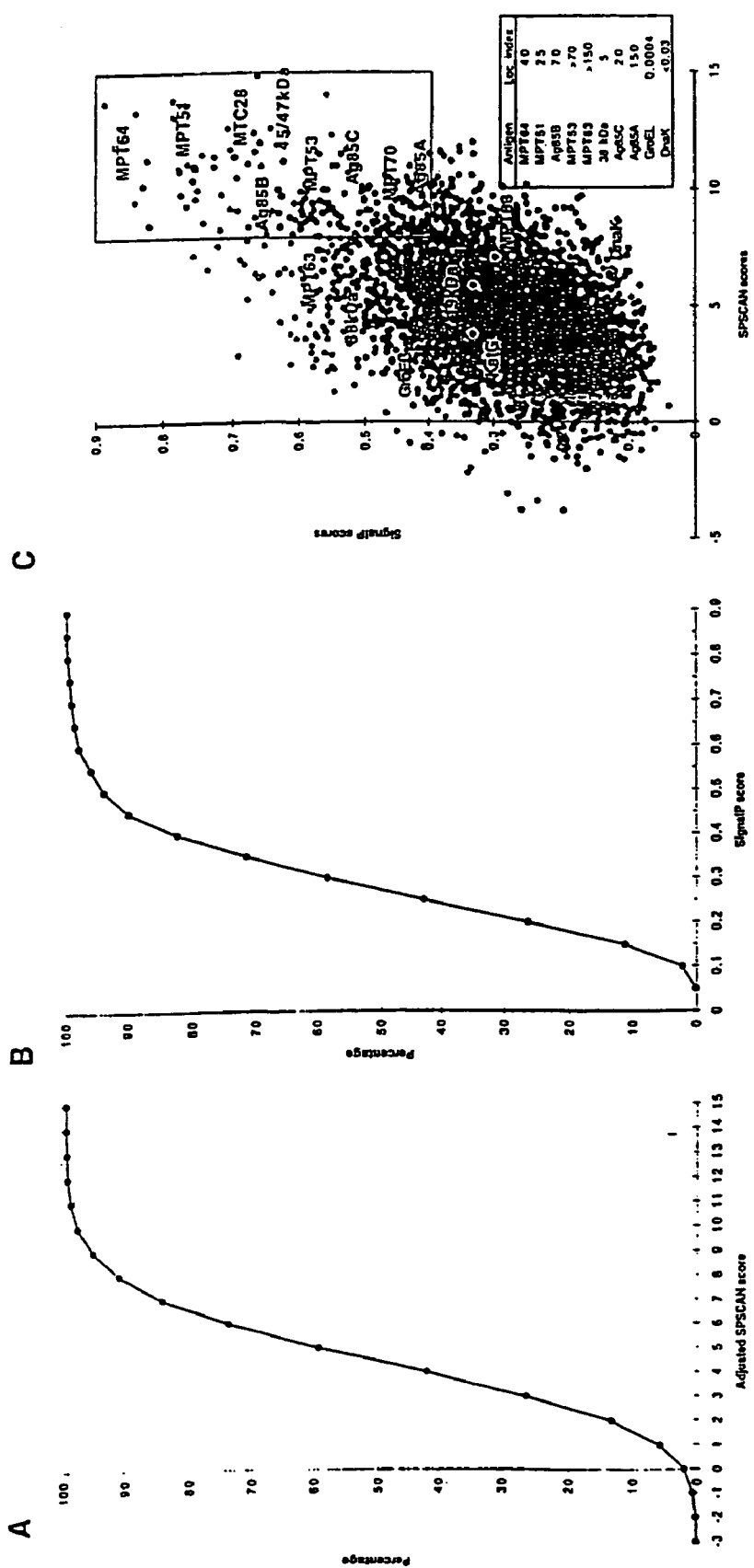
FIG. 3A is a line graph showing the distribution of SPSCAN scores for the 3924 *M. tuberculosis* protein sequences obtained from the Sanger Center website.
FIG. 3B is a line graph showing the distribution of SignalP scores for the 3924 protein sequences obtained from the Sanger Center website.
FIG. 3C is a "dot plot" of SignalP scores versus SPSCAN scores for the individual 3924 protein sequences obtained from the Sanger Centre website.

It is generally believed that proteins that are actively secreted by bacteria, especially intracellular bacteria (e.g., *Salmonella typhi* and *M. tuberculosis*), are effective as antigens that are capable of inducing protective immunity to the organism. A number of open reading frames (ORF), (i.e., DNA sequences that encode a protein) were predicted from the genomic sequence of *M. tuberculosis* [Cole et al. (1998) Nature 393:537-544]. The instant invention is based on the identification of a number of ORFs of this group that encode secreted polypeptides (see Example 1). The polypeptides encoded by the ORFs thus identified are designated *M. tuberculosis* Secreted Polypeptides (MTSP) and the DNA sequences encoding them are designated mtsp. Because they are secreted, we believe that the MTSP are both immunogenic and antigenic. The immune responses that they induce in subjects exposed to them are preferably also protective against *M. tuberculosis* infection in the subjects. The amino acid sequences of MTSP1-MTSP44 are shown in FIG. 1 and the nucleotide sequences of mtsp1-mtsp44 are shown in FIG. 2.

The invention encompasses: (a) isolated DNA molecules containing sequences (e.g., mtsp1-mtsp47) encoding polypeptides (e.g., MTSP1-MTSP47) secreted by *M. tuberculosis* and isolated portions of such DNA molecules that encode polypeptide segments having antigenic and immunogenic properties (i.e., functional segments); (b) the secreted polypeptides themselves (e.g., MTSP1-MTSP47) and functional segments of them; (c) antibodies (including antigen binding fragments, e.g., F(ab')$_2$, Fab, Fv, and single chain Fv fragments of such antibodies) that bind to the MTSP1-MTSP47 polypeptides and functional segments; (d) nucleic acid molecules (e.g., vectors) containing and capable of expressing one or more of the DNA molecules containing the mtsp1-mtsp47 sequences and portions of DNA molecules; (e) cells (e.g., bacterial, yeast, insect, or mammalian cells) transformed by such vectors; (f) compositions containing vectors encoding one or more *M. tuberculosis* polypeptides (or functional segments) including both the MTSP1-MTSP47 polypeptides (or functional segments thereof) and previously described *M. tuberculosis* polypeptides such as ESAT-6, 14 kDa antigen, MPT63, 19 kDa antigen, MPT64, MPT51, MTC28, 38 kDa antigen, 45/47 kDa antigen, MPB70, Ag85 complex, MPT53, and KatG (see also U.S. application Ser. No. 08/796,792); (g) compositions containing one or more *M. tuberculosis* polypeptides (or functional segments), including both the polypeptides of the invention and previously described *M. tuberculosis* polypeptides such as those described above; (h) compositions containing one or more of antibodies described in (c); (i) methods of diagnosis involving either (1) administration (e.g., intradermal injection) of the MTSP1-MTSP44 polypeptides of the invention, functional segments thereof, or mixtures of one more such polypeptides and/or functional segments to a subject suspected of having or being susceptible to *M. tuberculosis* infection, (2) in vitro testing of lymphocytes from such a subject for responsiveness to the MTSP1-MTSP47 polypeptides, functional segments thereof, or the above mixtures, or (3) testing of a bodily fluid (e.g., blood, saliva, plasma, serum, urine, or semen or a lavage such as a bronchoalveolar lavage, a vaginal lavage, or lower gastrointestinal lavage) for antibodies to the MTSP1-MTSP47 polypeptides or functional segments thereof, or the above-described mixtures; (j) methods of vaccination involving administration to a subject of the compositions of either (f), (g), (h) or a combination of any two or even all 3 compositions.

With respect to diagnosis, purified *M. tuberculosis* proteins, functional segments of such proteins, or mixtures of proteins and/or the functional fragments have the advantage of discriminating infection by *M. tuberculosis* from infection by other bacteria, and in particular, non-pathogenic mycobacteria. Of particular benefit in such assays are proteins encoded by genes present in *M. tuberculosis*, and possibly other members of the *M. tuberculosis* complex (e.g., *M. tuberculosis, M. bovis, M. microti,* and *M. africanum*), but absent from the Bacille Calmette-Guerin (BCG) attenuated strain of *M. bovis* which has been commonly used for vaccination. Use of such proteins (e.g., the MTSP16 protein whose sequence is shown in FIG. 1) for diagnosis allows for discrimination between infection by *M. tuberculosis* and vaccination with BCG. Furthermore, compositions containing the *M. tuberculosis* proteins, functional segments of them, or mixtures of the proteins and/or the functional segments allows for improved quality control since "batch-to-batch" variability is greatly reduced in comparison to complex mixtures such as purified protein derivative (PPD) of tuberculin.

Where vaccination is performed with nucleic acids both in vivo and ex vivo methods can be used. In vivo methods involve administration of the nucleic acids themselves to the subject and ex vivo methods involve obtaining cells (e.g., bone marrow cells or fibroblasts) from the subject, transducing the cells with the nucleic acids, preferably selecting or enriching for successfully transduced cells, and administering the transduced cells to the subject. Alternatively, the cells that are transduced and administered to the subject can be derived from another subject.

Methods of vaccination and diagnosis are described in greater detail in U.S. application Ser. No. 08/796,792 now U.S. Pat. No. 6,087,163 which is incorporated herein by reference in its entirety.

The following example is meant to illustrate, not limit the invention.

EXAMPLE 1

Computer Aided Identification of *M. tuberculosis* Secreted Proteins

Software.

The software used to manipulate and analyze protein sequences was available from public web servers or was part of the Genetics Computer Group (GCG) package [Wisconsin Package Version 9.1, Genetics Computer Group (GCG), Madison, Wis.]. Customized C-Shell scripts were used to automate some of the tasks or to extract selected information from the output of some of the programs. Signal peptides were predicted with SPSCAN, which is part of the GCG package, and SignalP, a program originating from the Center for Biological Sequence Analysis at the Technical University of Denmark, Lyngby, Denmark and currently available on the Internet. Putative transmembrane segments were identified with the program TMpred and prokaryotic membrane lipoprotein lipid attachment sites with the program PrositeScan, both programs originating from the Bioinformatics Group at the Swiss Institute for Experimental Cancer Research in Epalinges, Switzerland, and currently available on the Internet. Protein similarity and relatedness was established with GAP and PILEUP, both in the GCG package, Blast originating from the National Center for Biotechnology Information of the National Institutes for Health, Bethesda, Md., and AllAll originating from the Swiss Institute of Technology, Zurich, Switzerland, and currently available on the Internet.

Prediction of *M. tuberculosis* Proteins with Signal Peptides

The amino acid sequences of the 3924 proteins predicted by the analysis of the *M. tuberculosis* genomic sequence have been made available by the Sanger Centre, Cambridge, England, and were downloaded from the current Sanger Center website. Segments containing the first 70 amino acids of each predicted protein were analyzed by a system of our own design utilizing two different computer programs (SPSCAN and SignalP) designed to predict the occurrence of signal peptides. We concluded that combining the output from the two programs would increase the reliability of the selection. Both programs can detect signal peptides in polypeptides from eukaryotic and prokaryotic organisms, including gram-positive and gram-negative bacteria. To analyze the *M. tuberculosis* proteins the gram-positive mode was used. We performed an analysis with SPSCAN allowing only one prediction per protein, setting the minimum score threshold at −10, both in the standard and the adjusted modes. In the adjusted mode, signal peptides longer than a certain threshold value are penalized. We found that the correlation between the scores obtained with SPSCAN in the standard and adjusted modes increased with the value of the score, i.e., signal peptides that received high scores in standard mode also had high scores in the adjusted mode. We determined to use only the adjusted mode in subsequent steps.

To define cutoff values for the scores obtained with SPSCAN (in adjusted mode) and SignalP we took into account the following factors: (a) SignalP scores above 0.34 are generally considered significant; (b) the analysis of Haemophilus influenzae genome with SignalP yielded the prediction that about 10% of the encoded proteins contain a signal peptide; and (c) the average scores of thirteen known secreted or membrane-associated *M. tuberculosis* antigens was 9.11 (standard deviation (SD)=1.8) and 0.55 (SD=0.15), as calculated as above utilizing SPSCAN and SignalP, respectively (Table 1).

Figure 4:
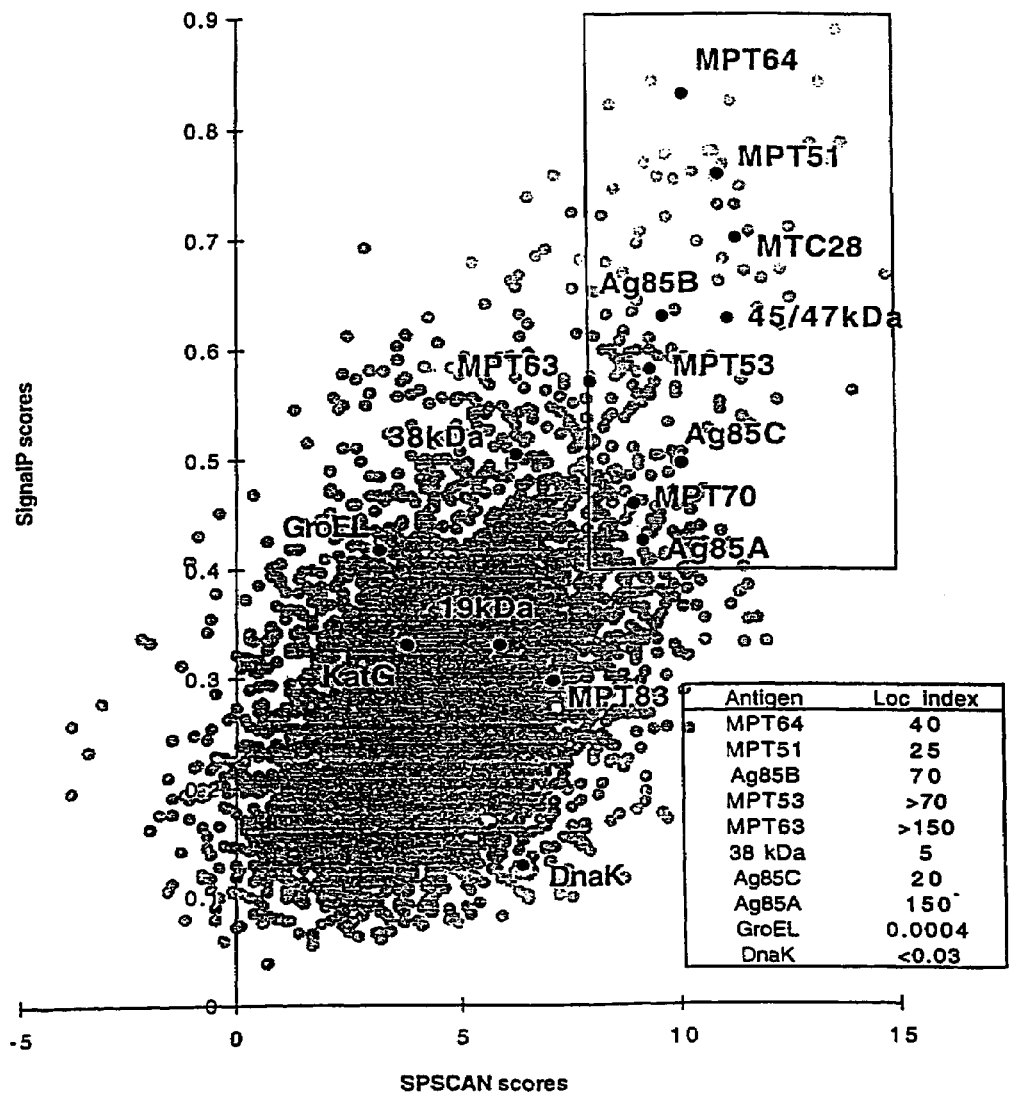
FIG. 4 is an enlargement of FIG. 3C.

Of the 3924 *M. tuberculosis* protein sequences downloaded from the Sanger Centre website, about 10% of the sequences had SPSCAN scores equal or higher than 8 (FIG. 3A) and about 10% of the sequences had SignalP scores equal or higher than 0.4 (FIG. 3B). We tentatively adopted these score values as "cutoffs" and we used the cutoffs to construct a list of proteins that were likely to be either secreted or exposed at the bacterial cell surface. This list included those proteins with SPSCAN scores higher than 8 and SignalP scores higher than 0.4. We refer to this group of proteins (208 entries, about 5% of the proteome) as the "Top208" group (FIG. 3C and FIG. 4).

TABLE 1

SPCAN and SignalP Scores of Known Secreted or Membrane Associated *M. tuberculosis* Polypeptide Antigens

| Polypeptide Antigens | Alternative Names | SPSCAN Score | SignalP Score |
|---|---|---|---|
| 19 kDa | | 5.9 | 0.331 |
| 38 kDa | PhoS, Ag78, antigen 5 | 6.3 | 0.505 |
| 45/47 kDa | | 11.2 | 0.627 |
| MPT44 | Ag85A, P32, FbpA | 9.2 | 0.425 |
| MPT45 | Ag85C, FbpC | 10.1 | 0.496 |
| MPT51 | | 11 | 0.758 |
| MPT53 | | 9.4 | 0.581 |
| MPT59 | Ag85B, á antigen, Ag 6, FbpB | 9.7 | 0.629 |
| MPT63 | | 8 | 0.57 |
| MPT64 | | 10.2 | 0.83 |
| MPT70 | | 9 | 0.459 |
| MPT83 | | 7.1 | 0.298 |
| MTC28 | | 11.4 | 0.7 |

Prediction of *M. tuberculosis* Secreted Proteins

A signal peptide may target a protein to the membrane but does not define a secreted protein, because additional transmembrane segments within the mature protein molecule can be present. In addition, lipoproteins are also targeted to the membrane by a signal peptide, but are not all secreted since cleavage of the signal peptide is coupled with the attachment of an acyl glycerol group that anchors the protein to the membrane. In light of these considerations and the fact that SignalP is not designed to differentiate lipoprotein signal peptides from secretory signal peptides, we believe that the Top208 group contains lipoproteins and proteins with multiple transmembrane segments, in addition to secreted proteins.

The number of putative transmembrane segments and the presence of lipoprotein lipid attachment sites were assessed by analyzing the Top208 proteins with TMpred and PrositeScan. TMpred identifies putative transmembrane segments by comparing a query amino acid sequence with a database of amino acid sequences of experimentally defined transmembrane segments. Scores higher than 500 are considered significant. PrositeScan compares query amino acid sequences against the Prosite database of protein motifs. The prokaryotic lipoprotein lipid attachment site motif is entry number PS00013. Our methodology identified a class of secreted proteins (the "Top208-TM1" group that included MTSP1-MTSP44) which were characterized by a single transmembrane segment (with score higher than 500) in the position predicted for the signal peptide and in which no lipoprotein motifs were identified. Other proteins had additional transmembrane segments with scores higher than 500, had lipoprotein motifs, or were excluded from the analysis because they belonged to the PE/PPE/PGRS families of proteins [Cole et al., 1998] and their biased amino acid composition made it difficult to obtain reliable results with SPSCAN, SignalP, or TMpred. A summary of the characteristics of the proteins we assigned to the Top208-TM1 group is presented in Table 2 and data regarding proteins MTSP1-MTSP47 are presented in Table 3. The amino acid sequences of the proteins are listed in FIG. 1 and the nucleotide sequences of ORF encoding them (mtsp1-mtsp47) are listed in FIG. 2.

TABLE 2

Features defining the *M. tuberculosis* proteins included in the Top208-TM1 group.

1. A signal peptide with score higher than 0.4 was predicted with SignalP in the first 70 amino acids.
2. A signal peptide with score higher than 8 was predicted with SPSCAN in the first 70 amino acids.
3. A single transmembrane segment, with a score greater than 500 and coinciding approximately with the putative signal peptide, was predicted with TMpred.
4. No lipoprotein lipid attachment sites were identified with PrositeScan.

TABLE 3

Proteins included in the Top208-TM1 group.

| Protein | No. of Amino Acids | SPSCAN Score | SPSCAN Sequence | SignalP Score | SignalP Sequence |
|---|---|---|---|---|---|
| MTSP20 | 130 | 12.4 | 1-32 | 0.672 | 1-32 |
| MTSP21 | 109 | 8.4 | 1-22 | 0.631 | 1-22 |
| MTSP23 | 114 | 10.2 | 1-34 | 0.592 | 1-34 |
| MTSP16 | 126 | 9.2 | 1-28 | 0.557 | 1-36 |
| MTSP24 | 125 | 11.4 | 1-35 | 0.73 | 1-35 |
| MTSP14 | 144 | 8.9 | 1-34 | 0.584 | 1-34 |
| MTSP13 | 157 | 10 | 1-32 | 0.753 | 1-32 |
| MTSP22 | 124 | 8.6 | 1-30 | 0.592 | 1-30 |
| MTSP25 | 155 | 9.5 | 35-49 | 0.842 | 1-49 |
| MTSP27 | 233 | 13.8 | 1-29 | 0.787 | 1-29 |
| MTSP11 | 233 | 10.9 | 1-32 | 0.779 | 1-32 |
| MTSP26 | 382 | 8.3 | 1-34 | 0.721 | 1-34 |
| MTSP12 | 214 | 12.6 | 1-28 | 0.71 | 1-28 |
| MTSP8 | 158 | 9.1 | 1-33 | 0.695 | 1-30 |
| MTSP10 | 155 | 8.8 | 15-45 | 0.669 | 1-45 |
| MTSP28 | 295 | 14.8 | 1-31 | 0.667 | 1-31 |
| MTSP9 | 241 | 10 | 1-22 | 0.635 | 1-22 |
| MTSP29 | 380 | 12.4 | 1-27 | 0.621 | 1-27 |
| MTSP2 | 111 | 10.6 | 1-28 | 0.579 | 1-28 |
| MTSP4 | 177 | 8.7 | 1-25 | 0.578 | 1-24 |
| MTSP17 | 219 | 8.9 | 1-29 | 0.543 | 1-29 |
| MTSP3 | 282 | 11.5 | 1-32 | 0.538 | 1-32 |
| MTSP18 | 220 | 8.8 | 38-68 | 0.537 | 1-68 |
| MTSP6 | 219 | 8.4 | 1-34 | 0.537 | 1-34 |
| MTSP7 | 136 | 11.7 | 1-24 | 0.53 | 1-24 |
| MTSP31 | 457 | 9.1 | 1-18 | 0.494 | 1-25 |
| MTSP30 | 286 | 8.3 | 15-37 | 0.469 | 1-37 |
| MTSP1 | 104 | 8.2 | 1-28 | 0.466 | 1-28 |
| MTSP15 | 134 | 10 | 1-21 | 0.458 | 1-56 |
| MTSP32 | 449 | 8.8 | 1-23 | 0.444 | 1-23 |
| MTSP19 | 169 | 10.5 | 28-53 | 0.438 | 1-53 |
| MTSP5 | 568 | 9.9 | 1-31 | 0.432 | 1-31 |
| MTSP33 | 113 | 11.9 | 1-25 | 0.873 | 1-25 |
| MTSP41 | 112 | 12 | 1-33 | 0.663 | 1-3 |
| MTSP38 | 173 | 10.5 | 1-28 | 0.697 | 1-28 |
| MTSP35 | 408 | 8.8 | 1-33 | 0.616 | 1-33 |
| MTSP34 | 149 | 13.7 | 1-23 | 0.888 | 1-23 |
| MTSP36 | 168 | 11.3 | 1-28 | 0.824 | 1-27 |
| MTSP42 | 521 | 8.4 | 1-34 | 0.679 | 1-34 |
| MTSP44 | 149 | 11 | 1-30 | 0.661 | 1-30 |
| MTSP37 | 228 | 9.4 | 1-23 | 0.598 | 1-23 |
| MTSP40 | 231 | 9.2 | 1-30 | 0.55 | 1-30 |
| MTSP43 | 137 | 8.2 | 1-36 | 0.485 | 1-37 |
| MTSP39 | 509 | 8.6 | 1-35 | 0.413 | 1-38 |
| MTSP45 | 145 | 8.4 | 1-46 | 0.412 | 1-62 |
| MTSP46 | 143 | 8.5 | 1-27 | 0.555 | 1-66 |
| MTSP47 | 171 | 8.3 | 1-35 | 0.424 | 1-30 |

SPSCAN sequence and SignalP sequence show the sequence, in terms of amino acid residue numbers, included in the signal peptide predicted by SPSCAN and SignalP, respectively.

TABLE 4

Presence mtsp coding regions in various strains of *Mycobacterium tuberculosis*.

| Coding Region | M. tuberculosis | M. bovis BCG | M. bovis | M. kansaii | M. africanum | M. scrofulaceum | M. fortuitum | M. marinum | M. malmoense | M. avium | M. gastri | M. chelonae | M. ulcerans |
|---|---|---|---|---|---|---|---|---|---|---|---|---|---|
| MTSP6 | + | + | + | + | + | + | + | + | + | + | + | + | + |
| MTSP28 | + | + | + | + | + | + | + | + | + | + | + | + | + |
| MTSP44 | + | + | + | + | + | + | + | + | + | + | + | + | +/− |
| MTSP34 | + | + | + | +/− | + | + | + | + | + | + | + | + | + |
| MTSP39 | + | + | + | + | + | + | + | + | + | + | + | + | + |
| MTSP1 | + | + | + | + | + | + | + | + | + | + | + | + | + |
| MTSP15 | + | + | + | + | + | + | + | + | + | + | + | + | + |
| MTSP35 | + | + | + | + | + | + | + | + | + | + | + | + | + |
| MTSP5 | + | + | + | + | + | + | + | + | + | + | + | + | + |
| MTSP46 | + | + | + | + | + | − | − | + | − | − | + | − | − |
| MTSP11 | + | + | + | + | + | − | − | − | + | − | + | − | − |
| MTSP24 | + | + | + | + | + | + | − | + | + | − | + | + | + |
| MTSP23 | + | + | + | + | + | + | − | + | + | + | + | + | − |
| MTSP41 | + | + | + | + | + | − | − | + | − | − | + | − | − |
| MTSP22 | + | + | + | − | + | − | + | − | − | − | + | − | − |
| MTSP26 | + | + | + | + | + | + | + | + | + | + | + | + | + |
| MTSP40 | + | + | + | + | + | + | + | + | + | + | + | + | + |
| MTSP13 | + | + | + | + | + | + | + | + | + | + | − | − | + |
| MTSP16 | + | − | − | − | + | − | − | − | − | − | − | − | − |

TABLE 4-continued

Presence mtsp coding regions in various strains of *Mycobacterium tuberculosis*.

| Coding Region | M. tuberculosis | M. bovis BCG | M. bovis | M. kansaii | M. africanum | M. scrofulaceum | M. fortuitum | M. marinum | M. malmoense | M. avium | M. gastri | M. chelonae | M. ulcerans |
|---|---|---|---|---|---|---|---|---|---|---|---|---|---|
| MTSP42 | + | + | + | + | + | + | − | + | + | − | + | + | + |
| MTSP36 | + | + | + | + | + |   |   |   |   |   |   |   |   |
| MTSP47 | + | + | + | − | + | − | − | − | − | − | − | − | − |
| MTSP38 | + | + | + | + | + | + | + | + | + | + | + | + | + |
| MTSP10 | + | + | + | + | + | + | + | + | + | + | + | + | + |
| MTSP37 | + | + | + | + | + |   |   |   |   |   |   |   |   |
| MTSP29 | + | + | + | + | + | + | + | + | + | + | + | +/− | +/− |
| MTSP31 | + | + | + | + | + | + | + | + | + | + | + | + | + |
| MTSP32 | + | + | + | + | + | + | + | + | + | + | + | + | + |
| MTSP30 | + | + | + | + | + | + | + | + | + | + | +/− | +/− | + |
| MTSP3 | + | + | + | + | + | + | + | + | + | + | + | + | + |
| MTSP20 | + | + | + | − | + |   |   |   |   |   |   |   |   |
| MTSP4 | + | + | + | + | + | + | + | + | + | + | + | + | + |
| MTSP27 | + | + | + | + | + | + | + | + | + | + | + | +/− | +/− |

The inventors have found, by standard DNA hybridization. Southern blotting techniques using the indicated coding regions as probes and DNA isolated from the indicated strains of *Mycobacteria*, that some of the coding regions are specific for the *M. tuberculosis* complex. (Table 4)

Although the invention has been described with reference to the presently preferred embodiment, it should be understood that various modifications can be made without departing from the spirit of the invention. Accordingly, the invention is limited only by the following claims.

---

What is claimed is:

1. An isolated DNA molecule consisting of a DNA sequence encoding a polypeptide with an amino acid sequence selected from the group consisting of the amino acid sequences of the polypeptides MTSP15 (SEQ. ID NO. 15), MTSP21 (SEQ. ID NO. 21), MTSP25 (SEQ. ID NO. 25), MTSP36 (SEQ. ID NO. 36), and MTSP47 (SEQ. ID NO. 47).

2. An isolated portion of the DNA molecule of claim 1, said portion encoding a segment of said polypeptide shorter than the full-length polypeptide, wherein said segment retains *Mycobacterium tuberculosis*-specific antigenic properties.

3. A vector comprising:
   a. The DNA molecule of claim 1; and
   b. Transcriptional and translational regulatory sequences operationally linked to said DNA sequence, said regulatory sequences allowing for expression of the polypeptide encoded by said DNA sequence in a cell.

4. A vector comprising:
   a. The DNA molecule of claim 2; and
   b. Transcriptional and translational regulatory sequences operationally linked to said DNA sequences, said regulatory sequences allowing for expression of the polypeptide encoded by said DNA sequence in a cell.

5. A cell transformed with the vector of claim 3.

6. A cell transformed with the vector of claim 4.

7. A composition comprising the vector of claim 3 and a pharmaceutically acceptable diluent or filler.

8. A composition comprising the vector of claim 4 and a pharmaceutically acceptable diluent or filler.

* * * * *

SEQUENCE LISTING

<160> NUMBER OF SEQ ID NOS: 94

<210> SEQ ID NO 1
<211> LENGTH: 103
<212> TYPE: PRT
<213> ORGANISM: Mycobacterium tuberculosis

<400> SEQUENCE: 1

```
Met Asn Arg Ile Val Gln Phe Gly Val Ser Ala Val Ala Ala Ala
 1               5                  10                  15

Ile Gly Ile Gly Ala Gly Ser Gly Ile Ala Ala Ala Phe Asp Gly Glu
            20                  25                  30

Asp Glu Val Thr Gly Pro Asp Ala Asp Arg Ala Arg Ala Ala Ala Val
            35                  40                  45

Gln Ala Val Pro Gly Gly Thr Ala Gly Glu Val Glu Thr Glu Thr Gly
        50                  55                  60

Glu Gly Ala Ala Ala Tyr Gly Val Leu Val Thr Arg Pro Asp Gly Thr
65                  70                  75                  80

Arg Val Glu Val His Leu Asp Arg Asp Phe Arg Val Leu Asp Thr Glu
                85                  90                  95

Pro Ala Asp Gly Asp Gly Gly
            100
```

<210> SEQ ID NO 2
<211> LENGTH: 110
<212> TYPE: PRT
<213> ORGANISM: Mycobacterium tuberculosis

<400> SEQUENCE: 2

```
Met Arg Leu Ser Leu Thr Ala Leu Ser Ala Gly Val Gly Ala Val Ala
 1               5                  10                  15
```

```
Met Ser Leu Thr Val Gly Ala Gly Val Ala Ser Ala Asp Pro Val Asp
            20                  25                  30

Ala Val Ile Asn Thr Thr Cys Asn Tyr Gly Gln Val Ala Ala Leu
            35                  40                  45

Asn Ala Thr Asp Pro Gly Ala Ala Gln Phe Asn Ala Ser Pro Val
 50                      55                  60

Ala Gln Ser Tyr Leu Arg Asn Phe Leu Ala Pro Pro Gln Arg
 65                  70                  75                  80

Ala Ala Met Ala Ala Gln Leu Gln Ala Val Pro Gly Ala Ala Gln Tyr
                85                  90                  95

Ile Gly Leu Val Glu Ser Val Ala Gly Ser Cys Asn Asn Tyr
            100                 105                 110
```

<210> SEQ ID NO 3
<211> LENGTH: 281
<212> TYPE: PRT
<213> ORGANISM: Mycobacterium tuberculosis

<400> SEQUENCE: 3

```
Met Phe Thr Gly Ile Ala Ser His Ala Gly Ala Leu Gly Ala Ala Leu
 1               5                  10                  15

Val Val Leu Ile Gly Ala Ala Ile Leu His Asp Gly Pro Ala Ala Ala
            20                  25                  30

Asp Pro Asn Gln Asp Asp Arg Phe Leu Ala Leu Leu Glu Lys Lys Glu
            35                  40                  45

Ile Pro Ala Val Ala Asn Val Pro Arg Val Ile Asp Ala Ala His Lys
 50                      55                  60

Val Cys Arg Lys Leu Asp Gly Gly Met Pro Val Asn Asp Ile Val Asp
 65                  70                  75                  80

Gly Leu Arg Asn Asp Ala Tyr Asn Ile Asp Pro Val Met Arg Leu Tyr
                85                  90                  95

Pro Val Arg Leu Thr Thr Thr Met Thr Arg Phe Ile Ser Ala Ala Val
            100                 105                 110

Glu Ile Tyr Cys Pro Asn His His Ser Lys Met Ala Phe Ala Met Ala
            115                 120                 125

Asn Phe Glu Pro Gly Ser Asn Glu Pro Thr His Arg Val Ala Ala Ser
 130                     135                 140

Thr Arg Ser Ala Val Asn Ser Gly Ser Asp Leu Arg Ala Ser Val Ser
145                  150                 155                 160

Asp Met Thr Ile Met Ser Pro Gly Trp Arg Glu Pro Thr Gly Ala Met
                165                 170                 175

Leu Ala Ser Val Leu Gly Ala Val Arg Ala Gly Asp Pro Leu Ile Pro
            180                 185                 190

Asn Pro Pro Pro Ile Pro Val Pro Pro Ala Ala Gln Thr Leu Ile
            195                 200                 205

Pro Pro Pro Pro Ile Val Ala Pro Pro Pro Arg Pro Ala Pro Pro
            210                 215                 220

Gln Gln Pro Pro Pro Pro Pro Glu Val Glu Pro Ala Gly Val
225                  230                 235                 240

Pro Gln Ser Gly Gly Ala Ala Gly Ser Gly Ala Gly Ser Gly Gly
                245                 250                 255

Gly Gly Gly Gly Asp Gly Pro Val Glu Pro Ser Pro Ala Arg Pro Met
            260                 265                 270

Pro Pro Gly Phe Ile Arg Leu Ala Pro
            275                 280
```

<210> SEQ ID NO 4
<211> LENGTH: 176
<212> TYPE: PRT
<213> ORGANISM: Mycobacterium tuberculosis

<400> SEQUENCE: 4

```
Met Thr Arg Leu Ile Pro Gly Cys Thr Leu Val Gly Leu Met Leu Thr
 1               5                  10                  15

Leu Leu Pro Ala Pro Thr Ser Ala Ala Gly Ser Asn Thr Ala Thr Thr
            20                  25                  30

Leu Phe Pro Val Asp Glu Val Thr Gln Leu Glu Thr His Thr Phe Leu
        35                  40                  45

Asp Cys His Pro Asn Gly Ser Cys Asp Phe Val Ala Gly Ala Asn Leu
 50                  55                  60

Arg Thr Pro Asp Gly Pro Thr Gly Phe Pro Pro Gly Leu Trp Ala Arg
 65                  70                  75                  80

Gln Thr Thr Glu Ile Arg Ser Thr Asn Arg Leu Ala Tyr Leu Asp Ala
                85                  90                  95

His Ala Thr Ser Gln Phe Glu Arg Val Met Lys Ala Gly Gly Ser Asp
            100                 105                 110

Val Ile Thr Thr Val Tyr Phe Gly Glu Gly Pro Pro Asp Lys Tyr Gln
        115                 120                 125

Thr Thr Gly Val Ile Asp Ser Thr Asn Trp Ser Thr Gly Gln Pro Met
130                 135                 140

Thr Asp Val Asn Val Ile Val Cys Thr His Met Gln Val Val Tyr Pro
145                 150                 155                 160

Gly Val Asn Leu Thr Ser Pro Ser Thr Cys Ala Gln Ala Asn Phe Ser
                165                 170                 175
```

<210> SEQ ID NO 5
<211> LENGTH: 567
<212> TYPE: PRT
<213> ORGANISM: Mycobacterium tuberculosis

<400> SEQUENCE: 5

```
Met Val Leu Arg Ser Arg Lys Ser Thr Leu Gly Val Val Cys Leu
 1               5                  10                  15

Ala Leu Val Leu Gly Gly Pro Leu Asn Gly Cys Ser Ser Ser Ala Ser
            20                  25                  30

His Arg Gly Pro Leu Asn Ala Met Gly Ser Pro Ala Ile Pro Ser Thr
        35                  40                  45

Ala Gln Glu Ile Pro Asn Pro Leu Arg Gly Gln Tyr Glu Asp Leu Met
 50                  55                  60

Glu Pro Leu Phe Pro Gln Gly Asn Pro Ala Gln Gln Arg Tyr Pro Pro
 65                  70                  75                  80

Trp Pro Ala Ser Tyr Asp Ala Ser Leu Arg Val Ser Trp Arg Gln Leu
                85                  90                  95

Gln Pro Thr Asp Pro Arg Thr Leu Pro Pro Asp Ala Pro Asp Asp Arg
            100                 105                 110

Lys Tyr Asp Phe Ser Val Ile Asp Asn Ala Leu Thr Arg Leu Ala Asp
        115                 120                 125

Arg Gly Met Arg Leu Thr Leu Arg Val Tyr Ala Tyr Ser Ser Cys Cys
130                 135                 140

Lys Ala Ser Tyr Pro Asp Gly Thr Asn Ile Ala Ile Pro Asp Trp Glu
145                 150                 155                 160
```

```
Arg Ala Ile Ala Ser Thr Asn Thr Ser Tyr Pro Gly Pro Ala Thr Asp
                165                 170                 175

Pro Ser Thr Gly Val Val Gln Val Val Pro Asn Phe Asn Asp Ser Thr
            180                 185                 190

Tyr Leu Asn Asp Phe Ala Gln Leu Leu Ala Ala Leu Gly Arg Arg Tyr
        195                 200                 205

Asp Gly Asp Glu Arg Leu Ser Val Phe Glu Phe Ser Gly Tyr Gly Asp
    210                 215                 220

Phe Ser Glu Asn His Val Ala Tyr Leu Arg Asp Thr Leu Gly Ala Pro
225                 230                 235                 240

Gly Pro Gly Pro Asp Glu Ser Val Ala Thr Leu Gly Tyr Tyr Ser Gln
                245                 250                 255

Phe Arg Asp Gln Asn Ile Thr Thr Ala Ser Ile Lys Gln Leu Ile Ala
            260                 265                 270

Ala Asn Val Ser Ala Phe Pro His Thr Gln Leu Val Thr Ser Pro Ala
        275                 280                 285

Asn Pro Glu Ile Val Arg Glu Leu Phe Ala Asp Glu Val Thr Asn Lys
    290                 295                 300

Leu Ala Ala Pro Val Gly Val Arg Ser Asp Cys Leu Gly Val Asp Ala
305                 310                 315                 320

Pro Leu Pro Ala Trp Ala Glu Ser Ser Thr Ser His Tyr Val Gln Thr
                325                 330                 335

Lys Asp Pro Val Val Ala Ala Leu Arg Gln Arg Leu Ala Thr Ala Pro
            340                 345                 350

Val Ile Thr Glu Trp Cys Glu Leu Pro Thr Gly Ser Ser Pro Arg Ala
        355                 360                 365

Tyr Tyr Glu Lys Gly Leu Arg Asp Val Ile Arg Tyr His Val Ser Met
    370                 375                 380

Thr Ser Ser Val Asn Phe Pro Asp Gln Thr Ala Thr Ser Pro Met Asp
385                 390                 395                 400

Pro Ala Leu Tyr Leu Val Trp Ala Gln Ala Asn Ala Ala Ala Gly Tyr
                405                 410                 415

Arg Tyr Ser Val Glu Ala Gln Pro Gly Ser Gln Ala Leu Ala Gly Lys
            420                 425                 430

Val Ala Thr Ile Ser Val Thr Trp Thr Asn Tyr Gly Ala Ala Ala Ala
        435                 440                 445

Thr Glu Lys Trp Val Pro Gly Tyr Arg Leu Val Asp Ser Thr Gly Gln
    450                 455                 460

Val Val Arg Thr Leu Pro Ala Ala Val Asp Leu Lys Thr Leu Val Ser
465                 470                 475                 480

Asp Gln Arg Gly Asp Arg Ser Ser Asp Gln Pro Thr Pro Ala Ser Val
                485                 490                 495

Ala Glu Thr Val Arg Val Asp Leu Ser Gly Leu Pro Ala Gly His Tyr
            500                 505                 510

Thr Leu Arg Ala Ala Ile Asp Trp Gln Gln His Lys Pro Asn Gly Ser
        515                 520                 525

His Val Val Asn Tyr Pro Pro Met Leu Leu Ser Arg Asp Gly Arg Asp
    530                 535                 540

Asp Ser Gly Phe Tyr Pro Val Ala Thr Leu Asp Ile Pro Arg Asp Ala
545                 550                 555                 560

Gln Thr Ala Val Asn Ala Ser
                565
```

<210> SEQ ID NO 6
<211> LENGTH: 218
<212> TYPE: PRT
<213> ORGANISM: Mycobacterium tuberculosis

<400> SEQUENCE: 6

Met Ser Arg Leu Leu Ala Leu Leu Cys Ala Ala Val Cys Thr Gly Cys
1               5                   10                  15

Val Ala Val Val Leu Ala Pro Val Ser Leu Ala Val Val Asn Pro Trp
                20                  25                  30

Phe Ala Asn Ser Val Gly Asn Ala Thr Gln Val Val Ser Val Val Gly
            35                  40                  45

Thr Gly Gly Ser Thr Ala Lys Met Asp Val Tyr Gln Arg Thr Ala Ala
        50                  55                  60

Gly Trp Gln Pro Leu Lys Thr Gly Ile Thr Thr His Ile Gly Ser Ala
65                  70                  75                  80

Gly Met Ala Pro Glu Ala Lys Ser Gly Tyr Pro Ala Thr Pro Met Gly
                85                  90                  95

Val Tyr Ser Leu Asp Ser Ala Phe Gly Thr Ala Pro Asn Pro Gly Gly
            100                 105                 110

Gly Leu Pro Tyr Thr Gln Val Gly Pro Asn His Trp Trp Ser Gly Asp
        115                 120                 125

Asp Asn Ser Pro Thr Phe Asn Ser Met Gln Val Cys Gln Lys Ser Gln
130                 135                 140

Cys Pro Phe Ser Thr Ala Asp Ser Glu Asn Leu Gln Ile Pro Gln Tyr
145                 150                 155                 160

Lys His Ser Val Val Met Gly Val Asn Lys Ala Lys Val Pro Gly Lys
                165                 170                 175

Gly Ser Ala Phe Phe Phe His Thr Thr Asp Gly Gly Pro Thr Ala Gly
            180                 185                 190

Cys Val Ala Ile Asp Asp Ala Thr Leu Val Gln Ile Ile Arg Trp Leu
        195                 200                 205

Arg Pro Gly Ala Val Ile Ala Ile Ala Lys
210                 215

<210> SEQ ID NO 7
<211> LENGTH: 135
<212> TYPE: PRT
<213> ORGANISM: Mycobacterium tuberculosis

<400> SEQUENCE: 7

Met Ile Arg Glu Leu Val Thr Thr Ala Ala Ile Thr Gly Ala Ala Ile
1               5                   10                  15

Gly Gly Ala Pro Val Ala Gly Ala Asp Pro Gln Arg Tyr Asp Gly Asp
                20                  25                  30

Val Pro Gly Met Asn Tyr Asp Ala Ser Leu Gly Ala Pro Cys Ser Ser
            35                  40                  45

Trp Glu Arg Phe Ile Phe Gly Arg Gly Pro Ser Gly Gln Ala Glu Ala
        50                  55                  60

Cys His Phe Pro Pro Pro Asn Gln Phe Pro Ala Glu Thr Gly Tyr
65                  70                  75                  80

Trp Val Ile Ser Tyr Pro Leu Tyr Gly Val Gln Gln Val Gly Ala Pro
                85                  90                  95

Cys Pro Lys Pro Gln Ala Ala Gln Ser Pro Asp Gly Leu Pro Met
            100                 105                 110

```
Leu Cys Leu Gly Ala Arg Gly Trp Gln Pro Gly Trp Phe Thr Gly Ala
        115                 120                 125

Gly Phe Phe Pro Pro Glu Pro
    130             135

<210> SEQ ID NO 8
<211> LENGTH: 157
<212> TYPE: PRT
<213> ORGANISM: Mycobacterium tuberculosis

<400> SEQUENCE: 8

Met Gly Glu Leu Arg Leu Val Gly Gly Val Leu Arg Val Leu Val Val
  1               5                  10                  15

Val Gly Ala Val Phe Asp Val Ala Val Leu Asn Ala Gly Ala Ala Ser
             20                  25                  30

Ala Asp Gly Pro Val Gln Leu Lys Ser Arg Leu Gly Asp Val Cys Leu
         35                  40                  45

Asp Ala Pro Ser Gly Ser Trp Phe Ser Pro Leu Val Ile Asn Pro Cys
     50                  55                  60

Asn Gly Thr Asp Phe Gln Arg Trp Asn Leu Thr Asp Asp Arg Gln Val
 65                  70                  75                  80

Glu Ser Val Ala Phe Pro Gly Glu Cys Val Asn Ile Gly Asn Ala Leu
                 85                  90                  95

Trp Ala Arg Leu Gln Pro Cys Val Asn Trp Ile Ser Gln His Trp Thr
            100                 105                 110

Val Gln Pro Asp Gly Leu Val Lys Ser Asp Leu Asp Ala Cys Leu Thr
        115                 120                 125

Val Leu Gly Gly Pro Asp Pro Gly Thr Trp Val Ser Thr Arg Trp Cys
    130                 135                 140

Asp Pro Asn Ala Pro Asp Gln Gln Trp Asp Ser Val Pro
145                 150                 155

<210> SEQ ID NO 9
<211> LENGTH: 240
<212> TYPE: PRT
<213> ORGANISM: Mycobacterium tuberculosis

<400> SEQUENCE: 9

Met Pro Ala Met Thr Ala Arg Ser Val Val Leu Ser Val Leu Leu Gly
  1               5                  10                  15

Ala His Pro Ala Trp Ala Thr Ala Ser Glu Leu Ile Gln Leu Thr Ala
             20                  25                  30

Asp Phe Gly Ile Lys Glu Thr Thr Leu Arg Val Ala Leu Thr Arg Met
         35                  40                  45

Val Gly Ala Gly Asp Leu Val Arg Ser Ala Asp Gly Tyr Arg Leu Ser
     50                  55                  60

Asp Arg Leu Leu Ala Arg Gln Arg Gln Asp Glu Ala Met Arg Pro
 65                  70                  75                  80

Arg Thr Arg Ala Trp His Gly Asn Trp His Met Leu Ile Val Thr Ser
                 85                  90                  95

Ile Gly Thr Asp Ala Arg Thr Arg Ala Ala Leu Arg Thr Cys Met His
            100                 105                 110

His Lys Arg Phe Gly Glu Leu Arg Glu Gly Val Trp Met Arg Pro Asp
        115                 120                 125

Asn Leu Asp Leu Asp Leu Glu Ser Asp Val Ala Ala Arg Val Arg Met
    130                 135                 140
```

```
Leu Thr Ala Arg Asp Glu Ala Pro Ala Asp Leu Ala Gly Gln Leu Trp
145                 150                 155                 160

Asp Leu Ser Gly Trp Thr Glu Ala Gly His Arg Leu Leu Gly Asp Met
                165                 170                 175

Ala Ala Ala Thr Asp Met Pro Gly Arg Phe Val Val Ala Ala Ala Met
            180                 185                 190

Val Arg His Leu Leu Thr Asp Pro Met Leu Pro Ala Glu Leu Leu Pro
        195                 200                 205

Ala Asp Trp Pro Gly Ala Gly Leu Arg Ala Ala Tyr His Asp Phe Ala
    210                 215                 220

Thr Ala Met Ala Lys Arg Arg Asp Ala Thr Gln Leu Leu Glu Val Thr
225                 230                 235                 240

<210> SEQ ID NO 10
<211> LENGTH: 154
<212> TYPE: PRT
<213> ORGANISM: Mycobacterium tuberculosis

<400> SEQUENCE: 10

Val Pro Ala Gly Val Gly Asn Ala Ser Gly Ser Val Leu Asp Met Thr
1               5                   10                  15

Ser Val Arg Thr Val Pro Ser Ala Val Ala Leu Val Thr Phe Ala Gly
            20                  25                  30

Ala Ala Leu Ser Gly Val Ile Pro Ala Ile Ala Arg Ala Asp Pro Val
        35                  40                  45

Gly His Gln Val Thr Tyr Thr Val Thr Thr Ser Asp Leu Met Ala
    50                  55                  60

Asn Ile Arg Tyr Met Ser Ala Asp Pro Pro Ser Met Ala Ala Phe Asn
65                  70                  75                  80

Ala Asp Ser Ser Lys Tyr Met Ile Thr Leu His Thr Pro Ile Ala Gly
                85                  90                  95

Gly Gln Pro Leu Val Tyr Thr Ala Thr Leu Ala Asn Pro Ser Gln Trp
            100                 105                 110

Ala Ile Val Thr Ala Ser Gly Gly Leu Arg Val Asn Pro Glu Phe His
        115                 120                 125

Cys Glu Ile Val Val Asp Gly Gln Val Val Ser Gln Asp Gly Gly
    130                 135                 140

Ser Gly Val Gln Cys Ser Thr Arg Pro Trp
145                 150

<210> SEQ ID NO 11
<211> LENGTH: 232
<212> TYPE: PRT
<213> ORGANISM: Mycobacterium tuberculosis

<400> SEQUENCE: 11

Met Thr Thr Ser Lys Ile Ala Thr Ala Phe Lys Thr Ala Thr Phe Ala
1               5                   10                  15

Leu Ala Ala Gly Ala Val Ala Leu Gly Leu Ala Ser Pro Ala Asp Ala
            20                  25                  30

Ala Ala Gly Thr Met Tyr Gly Asp Pro Ala Ala Ala Lys Tyr Trp
        35                  40                  45

Arg Gln Gln Thr Tyr Asp Asp Cys Val Leu Met Ser Ala Ala Asp Val
    50                  55                  60

Ile Gly Gln Val Thr Gly Arg Glu Pro Ser Glu Arg Ala Ile Ile Lys
65                  70                  75                  80
```

```
Val Ala Gln Ser Thr Pro Ser Val Val His Pro Gly Ser Ile Tyr Thr
                85                  90                  95

Lys Pro Ala Asp Ala Glu His Pro Asn Ser Gly Met Gly Thr Ser Val
            100                 105                 110

Ala Asp Ile Pro Thr Leu Leu Ala His Tyr Gly Val Asp Ala Val Ile
        115                 120                 125

Thr Asp Glu Asp His Ala Thr Ala Thr Gly Val Ala Thr Gly Met Ala
130                 135                 140

Ala Leu Glu Gln Tyr Leu Gly Ser Gly His Ala Val Ile Val Ser Ile
145                 150                 155                 160

Asn Ala Glu Met Ile Trp Gly Gln Pro Val Glu Thr Asp Ser Ala
                165                 170                 175

Gly Asn Pro Arg Ser Asp His Ala Val Val Thr Gly Val Asp Thr
            180                 185                 190

Glu Asn Gly Ile Val His Leu Asn Asp Ser Gly Thr Pro Thr Gly Arg
        195                 200                 205

Asp Glu Gln Ile Pro Met Glu Thr Phe Val Glu Ala Trp Ala Thr Ser
210                 215                 220

His Asp Phe Met Ala Val Thr Thr
225                 230

<210> SEQ ID NO 12
<211> LENGTH: 213
<212> TYPE: PRT
<213> ORGANISM: Mycobacterium tuberculosis

<400> SEQUENCE: 12

Met Gly Val Ile Ala Arg Val Val Gly Val Ala Ala Cys Gly Leu Ser
1               5                   10                  15

Leu Ala Val Leu Ala Ala Pro Thr Ala Gly Ala Glu Pro Thr Gly
            20                  25                  30

Ala Leu Pro Pro Met Thr Ser Ser Gly Ser Gly Pro Val Ile Gly Asp
        35                  40                  45

Gly Asp Ala Ala Leu Arg Gln Arg Ile Ser Gln Gln Leu Phe Ser Phe
50                  55                  60

Gly Asp Pro Thr Val Gln Glu Val Asp Gly Ser Asp Ala Ala Gln Phe
65                  70                  75                  80

Ile Thr Ala Ala Ala Val Ala Asp Arg Asp Val Ala Ser Val Phe
                85                  90                  95

Leu Pro Leu Gln Arg Val Leu Gly Cys Gln Gln Asn Thr Ala Gly Ser
            100                 105                 110

Gly Ala Gly Phe Gly Ala Arg Ala Tyr Arg Arg Thr Asp Gly Gln Trp
        115                 120                 125

Gly Gly Ala Met Leu Val Val Ala Lys Ser Thr Val Ser Asp Val Asp
130                 135                 140

Ala Leu Lys Ala Cys Val Lys Ser Gly Trp Arg Lys Ala Thr Ala Gly
145                 150                 155                 160

Thr Pro Thr Ser Met Cys Asn Asn Gly Trp Thr Tyr Pro Pro Phe Ala
                165                 170                 175

Asp Thr Arg Arg Gly Glu Glu Gly Tyr Phe Val Leu Leu Ala Gly Thr
            180                 185                 190

Ala Ser Asp Phe Cys Ser Ala Pro Asn Ala Asn Tyr Arg Thr Thr Ala
        195                 200                 205

Ser Ser Trp Pro Gly
    210
```

<210> SEQ ID NO 13
<211> LENGTH: 156
<212> TYPE: PRT
<213> ORGANISM: Mycobacterium tuberculosis

<400> SEQUENCE: 13

Met Arg Leu Lys Pro Ala Pro Ser Pro Ala Ala Phe Ala Val Ala
1               5                  10                  15

Gly Leu Ile Leu Ala Gly Trp Ala Gly Ser Val Gly Leu Ala Gly Ala
            20                  25                  30

Asp Pro Glu Pro Ala Pro Thr Pro Lys Thr Ala Ile Asp Ser Asp Gly
        35                  40                  45

Thr Tyr Ala Val Gly Ile Asp Ile Ala Pro Gly Thr Tyr Ser Ser Ala
    50                  55                  60

Gly Pro Val Gly Asp Gly Thr Cys Tyr Trp Lys Arg Met Gly Asn Pro
65                  70                  75                  80

Asp Gly Ala Leu Ile Asp Asn Ala Leu Ser Lys Lys Pro Gln Val Val
                85                  90                  95

Thr Ile Glu Pro Thr Asp Lys Ala Phe Lys Thr His Gly Cys Gln Pro
            100                 105                 110

Trp Gln Asn Thr Gly Ser Glu Gly Ala Ala Pro Ala Gly Val Pro Gly
        115                 120                 125

Pro Glu Ala Gly Ala Gln Leu Gln Asn Gln Leu Gly Ile Leu Asn Gly
    130                 135                 140

Leu Leu Gly Pro Thr Gly Gly Arg Val Pro Gln Pro
145                 150                 155

<210> SEQ ID NO 14
<211> LENGTH: 143
<212> TYPE: PRT
<213> ORGANISM: Mycobacterium tuberculosis

<400> SEQUENCE: 14

Met Ile Thr Asn Leu Arg Arg Arg Thr Ala Met Ala Ala Ala Gly Leu
1               5                  10                  15

Gly Ala Ala Leu Gly Leu Gly Ile Leu Leu Val Pro Thr Val Asp Ala
            20                  25                  30

His Leu Ala Asn Gly Ser Met Ser Glu Val Met Met Ser Glu Ile Ala
        35                  40                  45

Gly Leu Pro Ile Pro Pro Ile Ile His Tyr Gly Ala Ile Ala Tyr Ala
    50                  55                  60

Pro Ser Gly Ala Ser Gly Lys Ala Trp His Gln Arg Thr Pro Ala Arg
65                  70                  75                  80

Ala Glu Gln Val Ala Leu Glu Lys Cys Gly Asp Lys Thr Cys Lys Val
                85                  90                  95

Val Ser Arg Phe Thr Arg Cys Gly Ala Val Ala Tyr Asn Gly Ser Lys
            100                 105                 110

Tyr Gln Gly Gly Thr Gly Leu Thr Arg Arg Ala Ala Glu Asp Asp Ala
        115                 120                 125

Val Asn Arg Leu Glu Gly Gly Arg Ile Val Asn Trp Ala Cys Asn
    130                 135                 140

<210> SEQ ID NO 15
<211> LENGTH: 133
<212> TYPE: PRT
<213> ORGANISM: Mycobacterium tuberculosis

<400> SEQUENCE: 15

Val Thr Val Leu Leu Asp Ala Asn Val Leu Ile Ala Leu Val Ala
1               5                   10                  15

Glu His Val His His Asp Ala Ala Ala Asp Trp Leu Met Ala Ser Asp
                20                  25                  30

Thr Gly Phe Ala Thr Cys Pro Met Thr Gln Gly Ser Leu Val Arg Phe
            35                  40                  45

Leu Val Arg Ser Gly Gln Ser Ala Ala Ala Arg Asp Val Val Ser
    50                  55                  60

Ala Val Gln Cys Thr Ser Arg His Glu Phe Trp Pro Asp Ala Leu Ser
65                  70                  75                  80

Phe Ala Gly Val Glu Val Ala Gly Val Val Gly His Arg Gln Val Thr
                85                  90                  95

Asp Ala Tyr Leu Ala Gln Leu Ala Arg Ser His Asp Gly Gln Leu Ala
            100                 105                 110

Thr Leu Asp Ser Gly Leu Ala His Leu His Gly Asp Val Ala Val Leu
        115                 120                 125

Ile Pro Thr Thr Thr
        130

<210> SEQ ID NO 16
<211> LENGTH: 125
<212> TYPE: PRT
<213> ORGANISM: Mycobacterium tuberculosis

<400> SEQUENCE: 16

Val Gln Arg Gln Ser Leu Met Pro Gln Gln Thr Leu Ala Ala Gly Val
1               5                   10                  15

Phe Val Gly Ala Leu Leu Cys Gly Val Val Thr Ala Ala Val Pro Pro
                20                  25                  30

His Ala Arg Ala Asp Val Val Ala Tyr Leu Val Asn Val Thr Val Arg
            35                  40                  45

Pro Gly Tyr Asn Phe Ala Asn Ala Asp Ala Ala Leu Ser Tyr Gly His
        50                  55                  60

Gly Leu Cys Glu Lys Val Ser Arg Gly Arg Pro Tyr Ala Gln Ile Ile
65                  70                  75                  80

Ala Asp Val Lys Ala Asp Phe Asp Thr Arg Asp Gln Tyr Gln Ala Ser
                85                  90                  95

Tyr Leu Leu Ser Gln Ala Val Asn Glu Leu Cys Pro Ala Leu Ile Trp
            100                 105                 110

Gln Leu Arg Asn Ser Ala Val Asp Asn Arg Arg Ser Gly
        115                 120                 125

<210> SEQ ID NO 17
<211> LENGTH: 218
<212> TYPE: PRT
<213> ORGANISM: Mycobacterium tuberculosis

<400> SEQUENCE: 17

Val Arg Ser Tyr Leu Leu Arg Ile Glu Leu Ala Asp Arg Pro Gly Ser
1               5                   10                  15

Leu Gly Ser Leu Ala Val Ala Leu Gly Ser Val Gly Ala Asp Ile Leu
                20                  25                  30

Ser Leu Asp Val Val Glu Arg Gly Asn Gly Tyr Ala Ile Asp Asp Leu
            35                  40                  45

-continued

```
Val Val Glu Leu Pro Pro Gly Ala Met Pro Asp Thr Leu Ile Thr Ala
         50                  55                  60

Ala Glu Ala Leu Asn Gly Val Arg Val Asp Ser Val Arg Pro His Thr
 65                  70                  75                  80

Gly Leu Leu Glu Ala His Arg Glu Leu Glu Leu Leu Asp His Val Ala
                 85                  90                  95

Ala Ala Glu Gly Ala Thr Ala Arg Leu Gln Val Leu Val Asn Glu Ala
                100                 105                 110

Pro Arg Val Leu Arg Val Ser Trp Cys Thr Val Leu Arg Ser Ser Gly
                115                 120                 125

Gly Glu Leu His Arg Leu Ala Gly Ser Pro Gly Ala Pro Glu Thr Arg
        130                 135                 140

Ala Asn Ser Ala Pro Trp Leu Pro Ile Glu Arg Ala Ala Ala Leu Asp
145                 150                 155                 160

Gly Gly Ala Asp Trp Val Pro Gln Ala Trp Arg Asp Met Asp Thr Thr
                165                 170                 175

Met Val Ala Ala Pro Leu Gly Asp Thr His Thr Ala Val Val Leu Gly
                180                 185                 190

Arg Pro Gly Pro Glu Phe Arg Pro Ser Glu Val Ala Arg Leu Gly Tyr
                195                 200                 205

Leu Ala Gly Ile Val Ala Thr Met Leu Arg
        210                 215

<210> SEQ ID NO 18
<211> LENGTH: 219
<212> TYPE: PRT
<213> ORGANISM: Mycobacterium tuberculosis

<400> SEQUENCE: 18

Met Pro Asp Gly Glu Gln Ser Gln Pro Pro Ala Gln Glu Asp Ala Glu
 1               5                  10                  15

Asp Asp Ser Arg Pro Asp Ala Ala Glu Ala Ala Ala Glu Pro Lys
                 20                  25                  30

Ser Ser Ala Gly Pro Met Phe Ser Thr Tyr Gly Ile Ala Ser Thr Leu
         35                  40                  45

Leu Gly Val Leu Ser Val Ala Ala Val Val Leu Gly Ala Met Ile Trp
         50                  55                  60

Ser Ala His Arg Asp Asp Ser Gly Glu Arg Thr Tyr Leu Thr Arg Val
 65                  70                  75                  80

Met Leu Thr Ala Ala Glu Trp Thr Ala Val Leu Ile Asn Met Asn Ala
                 85                  90                  95

Asp Asn Ile Asp Ala Ser Leu Gln Arg Leu His Asp Gly Thr Val Gly
                100                 105                 110

Gln Leu Asn Thr Asp Phe Asp Ala Val Val Gln Pro Tyr Arg Gln Val
        115                 120                 125

Val Glu Lys Leu Arg Thr His Ser Ser Gly Arg Ile Glu Ala Val Ala
        130                 135                 140

Ile Asp Thr Val His Arg Glu Leu Asp Thr Gln Ser Gly Ala Ala Arg
145                 150                 155                 160

Pro Val Val Thr Thr Lys Leu Pro Pro Phe Ala Thr Arg Thr Asp Ser
                165                 170                 175

Val Leu Leu Val Ala Thr Ser Val Ser Glu Asn Ala Gly Ala Lys Pro
                180                 185                 190

Gln Thr Val His Trp Asn Leu Arg Leu Asp Val Ser Asp Val Asp Gly
        195                 200                 205
```

```
Lys Leu Met Ile Ser Arg Leu Glu Ser Ile Arg
    210                 215

<210> SEQ ID NO 19
<211> LENGTH: 168
<212> TYPE: PRT
<213> ORGANISM: Mycobacterium tuberculosis

<400> SEQUENCE: 19

Met Lys Met Val Lys Ser Ile Ala Ala Gly Leu Thr Ala Ala Ala Ala
 1               5                  10                  15

Ile Gly Ala Ala Ala Gly Val Thr Ser Ile Met Ala Gly Gly Pro
                20                  25                  30

Val Val Tyr Gln Met Gln Pro Val Val Phe Gly Ala Pro Leu Pro Leu
                35                  40                  45

Asp Pro Ala Ser Ala Pro Asp Val Pro Thr Ala Ala Gln Leu Thr Ser
         50                  55                  60

Leu Leu Asn Ser Leu Ala Asp Pro Asn Val Ser Phe Ala Asn Lys Gly
 65                  70                  75                  80

Ser Leu Val Glu Gly Gly Ile Gly Gly Thr Glu Ala Arg Ile Ala Asp
                 85                  90                  95

His Lys Leu Lys Lys Ala Ala Glu His Gly Asp Leu Pro Leu Ser Phe
            100                 105                 110

Ser Val Thr Asn Ile Gln Pro Ala Ala Ala Gly Ser Ala Thr Ala Asp
            115                 120                 125

Val Ser Val Ser Gly Pro Lys Leu Ser Ser Pro Val Thr Gln Asn Val
        130                 135                 140

Thr Phe Val Asn Gln Gly Gly Trp Met Leu Ser Arg Ala Ser Ala Met
145                 150                 155                 160

Glu Leu Leu Gln Ala Ala Gly Asn
                165

<210> SEQ ID NO 20
<211> LENGTH: 129
<212> TYPE: PRT
<213> ORGANISM: Mycobacterium tuberculosis

<400> SEQUENCE: 20

Met Asn Leu Arg Arg His Gln Thr Leu Thr Leu Arg Leu Leu Ala Ala
 1               5                  10                  15

Ser Ala Gly Ile Leu Ser Ala Ala Ala Phe Ala Ala Pro Ala Gln Ala
                20                  25                  30

Asn Pro Val Asp Asp Ala Phe Ile Ala Ala Leu Asn Asn Ala Gly Val
                35                  40                  45

Asn Tyr Gly Asp Pro Val Asp Ala Lys Ala Leu Gly Gln Ser Val Cys
         50                  55                  60

Pro Ile Leu Ala Glu Pro Gly Gly Ser Phe Asn Thr Ala Val Ala Ser
 65                  70                  75                  80

Val Val Ala Arg Ala Gln Gly Met Ser Gln Asp Met Ala Gln Thr Phe
                 85                  90                  95

Thr Ser Ile Ala Ile Ser Met Tyr Cys Pro Ser Val Met Ala Asp Val
            100                 105                 110

Ala Ser Gly Asn Leu Pro Ala Leu Pro Asp Met Pro Gly Leu Pro Gly
        115                 120                 125

Ser
```

```
<210> SEQ ID NO 21
<211> LENGTH: 108
<212> TYPE: PRT
<213> ORGANISM: Mycobacterium tuberculosis

<400> SEQUENCE: 21

Met Arg Val Val Ser Thr Leu Leu Ser Ile Pro Leu Met Ile Gly Leu
 1               5                  10                  15

Ala Val Pro Ala His Ala Gly Pro Ser Gly Asp Asp Ala Val Phe Leu
            20                  25                  30

Ala Ser Leu Glu Arg Ala Gly Ile Thr Tyr Ser His Pro Asp Gln Ala
        35                  40                  45

Ile Ala Ser Gly Lys Ala Val Cys Ala Leu Val Glu Ser Gly Glu Ser
    50                  55                  60

Gly Leu Gln Val Val Asn Glu Leu Arg Thr Arg Asn Pro Gly Phe Ser
65                  70                  75                  80

Met Asp Gly Cys Cys Lys Phe Ala Ala Ile Ser Ala His Val Tyr Cys
                85                  90                  95

Pro His Gln Ile Thr Lys Thr Ser Val Ser Ala Lys
            100                 105

<210> SEQ ID NO 22
<211> LENGTH: 123
<212> TYPE: PRT
<213> ORGANISM: Mycobacterium tuberculosis

<400> SEQUENCE: 22

Met Ala Arg Thr Leu Ala Leu Arg Ala Ser Ala Gly Leu Val Ala Gly
 1               5                  10                  15

Met Ala Met Ala Ala Ile Thr Leu Ala Pro Gly Ala Arg Ala Glu Thr
            20                  25                  30

Gly Glu Gln Phe Pro Gly Asp Gly Val Phe Leu Val Gly Thr Asp Ile
        35                  40                  45

Ala Pro Gly Thr Tyr Arg Thr Glu Gly Pro Ser Asn Pro Leu Ile Leu
    50                  55                  60

Val Phe Gly Arg Val Ser Glu Leu Ser Thr Cys Ser Trp Ser Thr His
65                  70                  75                  80

Ser Ala Pro Glu Val Ser Asn Glu Asn Ile Val Asp Thr Asn Thr Ser
                85                  90                  95

Met Gly Pro Met Ser Val Val Ile Pro Pro Thr Val Ala Ala Phe Gln
            100                 105                 110

Thr His Asn Cys Lys Leu Trp Met Arg Ile Ser
        115                 120

<210> SEQ ID NO 23
<211> LENGTH: 113
<212> TYPE: PRT
<213> ORGANISM: Mycobacterium tuberculosis

<400> SEQUENCE: 23

Met Leu Ser Pro Leu Ser Pro Arg Ile Ile Ala Ala Phe Thr Thr Ala
 1               5                  10                  15

Val Gly Ala Ala Ala Ile Gly Leu Ala Val Ala Thr Gly Thr Ala
            20                  25                  30

Gly Ala Asn Thr Lys Asp Glu Ala Phe Ile Ala Gln Met Glu Ser Ile
        35                  40                  45

Gly Val Thr Phe Ser Ser Pro Gln Val Ala Thr Gln Gln Ala Gln Leu
```

```
                50                  55                  60
Val Cys Lys Lys Leu Ala Ser Gly Glu Thr Gly Thr Glu Ile Ala Glu
 65                  70                  75                  80

Glu Val Leu Ser Gln Thr Asn Leu Thr Thr Lys Gln Ala Ala Tyr Phe
                 85                  90                  95

Val Val Asp Ala Thr Lys Ala Tyr Cys Pro Gln Tyr Ala Ser Gln Leu
                100                 105                 110

Thr

<210> SEQ ID NO 24
<211> LENGTH: 124
<212> TYPE: PRT
<213> ORGANISM: Mycobacterium tuberculosis

<400> SEQUENCE: 24

Met Thr Thr Met Ile Thr Leu Arg Arg Arg Phe Ala Val Ala Val Ala
  1               5                  10                  15

Gly Val Ala Thr Ala Ala Ala Thr Thr Val Thr Leu Ala Pro Ala Pro
                 20                  25                  30

Ala Asn Ala Ala Asp Val Tyr Gly Ala Ile Ala Tyr Ser Gly Asn Gly
                 35                  40                  45

Ser Trp Gly Arg Ser Trp Asp Tyr Pro Thr Arg Ala Ala Ala Glu Ala
 50                  55                  60

Thr Ala Val Lys Ser Cys Gly Tyr Ser Asp Cys Lys Val Leu Thr Ser
 65                  70                  75                  80

Phe Thr Ala Cys Gly Ala Val Ala Ala Asn Asp Arg Ala Tyr Gln Gly
                 85                  90                  95

Gly Val Gly Pro Thr Leu Ala Ala Met Lys Asp Ala Leu Thr Lys
                100                 105                 110

Leu Gly Gly Gly Tyr Ile Asp Thr Trp Ala Cys Asn
                115                 120

<210> SEQ ID NO 25
<211> LENGTH: 154
<212> TYPE: PRT
<213> ORGANISM: Mycobacterium tuberculosis

<400> SEQUENCE: 25

Met Thr Pro Gly Leu Leu Thr Thr Ala Gly Ala Gly Arg Pro Arg Asp
  1               5                  10                  15

Arg Cys Ala Arg Ile Val Cys Thr Val Phe Ile Glu Thr Ala Val Val
                 20                  25                  30

Ala Thr Met Phe Val Ala Leu Leu Gly Leu Ser Thr Ile Ser Ser Lys
                 35                  40                  45

Ala Asp Asp Ile Asp Trp Asp Ala Ile Ala Gln Cys Glu Ser Gly Gly
 50                  55                  60

Asn Trp Ala Ala Asn Thr Gly Asn Gly Leu Tyr Gly Gly Leu Gln Ile
 65                  70                  75                  80

Ser Gln Ala Thr Trp Asp Ser Asn Gly Gly Val Gly Ser Pro Ala Ala
                 85                  90                  95

Ala Ser Pro Gln Gln Gln Ile Glu Val Ala Asp Asn Ile Met Lys Thr
                100                 105                 110

Gln Gly Pro Gly Ala Trp Pro Lys Cys Ser Ser Cys Ser Gln Gly Asp
                115                 120                 125

Ala Pro Leu Gly Ser Leu Thr His Ile Leu Thr Phe Leu Ala Ala Glu
                130                 135                 140
```

Thr Gly Gly Cys Ser Gly Ser Arg Asp Asp
145                 150

<210> SEQ ID NO 26
<211> LENGTH: 381
<212> TYPE: PRT
<213> ORGANISM: Mycobacterium tuberculosis

<400> SEQUENCE: 26

Val Gln Gly Ala Val Ala Gly Leu Val Phe Leu Ala Val Leu Val Ile
1               5                   10                  15

Phe Ala Ile Ile Val Val Ala Lys Ser Val Ala Leu Ile Pro Gln Ala
            20                  25                  30

Glu Ala Ala Val Ile Glu Arg Leu Gly Arg Tyr Ser Arg Thr Val Ser
        35                  40                  45

Gly Gln Leu Thr Leu Leu Val Pro Phe Ile Asp Arg Val Arg Ala Arg
    50                  55                  60

Val Asp Leu Arg Glu Arg Val Val Ser Phe Pro Pro Gln Pro Val Ile
65                  70                  75                  80

Thr Glu Asp Asn Leu Thr Leu Asn Ile Asp Thr Val Val Tyr Phe Gln
                85                  90                  95

Val Thr Val Pro Gln Ala Ala Val Tyr Glu Ile Ser Asn Tyr Ile Val
            100                 105                 110

Gly Val Glu Gln Leu Thr Thr Thr Leu Arg Asn Val Val Gly Gly
        115                 120                 125

Met Thr Leu Glu Gln Thr Leu Thr Ser Arg Asp Gln Ile Asn Ala Gln
    130                 135                 140

Leu Arg Gly Val Leu Asp Glu Ala Thr Gly Arg Trp Gly Leu Arg Val
145                 150                 155                 160

Ala Arg Val Glu Leu Arg Ser Ile Asp Pro Pro Ser Ile Gln Ala
                165                 170                 175

Ser Met Glu Lys Gln Met Lys Ala Asp Arg Glu Lys Arg Ala Met Ile
            180                 185                 190

Leu Thr Ala Glu Gly Thr Arg Glu Ala Ile Lys Gln Ala Glu Gly
        195                 200                 205

Gln Lys Gln Ala Gln Ile Leu Ala Ala Glu Gly Ala Lys Gln Ala Ala
    210                 215                 220

Ile Leu Ala Ala Glu Ala Asp Arg Gln Ser Arg Met Leu Arg Ala Gln
225                 230                 235                 240

Gly Glu Arg Ala Ala Ala Tyr Leu Gln Ala Gln Gly Gln Ala Lys Ala
                245                 250                 255

Ile Glu Lys Thr Phe Ala Ala Ile Lys Ala Gly Arg Pro Thr Pro Glu
            260                 265                 270

Met Leu Ala Tyr Gln Tyr Leu Gln Thr Leu Pro Glu Met Ala Arg Gly
        275                 280                 285

Asp Ala Asn Lys Val Trp Val Val Pro Ser Asp Phe Asn Ala Ala Leu
    290                 295                 300

Gln Gly Phe Thr Arg Leu Leu Gly Lys Pro Gly Glu Asp Gly Val Phe
305                 310                 315                 320

Arg Phe Glu Pro Ser Pro Val Glu Asp Gln Pro Lys His Ala Ala Asp
                325                 330                 335

Gly Asp Asp Ala Glu Val Ala Gly Trp Phe Ser Thr Asp Thr Asp Pro
            340                 345                 350

Ser Ile Ala Arg Ala Val Ala Thr Ala Glu Ala Ile Ala Arg Lys Pro

```
                355                 360                 365
Val Glu Gly Ser Leu Gly Thr Pro Pro Arg Leu Thr Gln
    370                 375                 380

<210> SEQ ID NO 27
<211> LENGTH: 232
<212> TYPE: PRT
<213> ORGANISM: Mycobacterium tuberculosis

<400> SEQUENCE: 27

Leu Gln Thr Ala His Arg Arg Phe Ala Ala Phe Ala Ala Val Leu
1               5                  10                  15

Leu Ala Val Val Cys Leu Pro Ala Asn Thr Ala Ala Asp Asp Lys
                20                  25                  30

Leu Pro Leu Gly Gly Gly Ala Gly Ile Val Val Asn Gly Asp Thr Met
                35                  40                  45

Cys Thr Leu Thr Thr Ile Gly His Asp Lys Asn Gly Asp Leu Ile Gly
    50                  55                  60

Phe Thr Ser Ala His Cys Gly Gly Pro Gly Ala Gln Ile Ala Ala Glu
65                  70                  75                  80

Gly Ala Glu Asn Ala Gly Pro Val Gly Ile Met Val Ala Gly Asn Asp
                85                  90                  95

Gly Leu Asp Tyr Ala Val Ile Lys Phe Asp Pro Ala Lys Val Thr Pro
                100                 105                 110

Val Ala Val Phe Asn Gly Phe Ala Ile Asn Gly Ile Gly Pro Asp Pro
                115                 120                 125

Ser Phe Gly Gln Ile Ala Cys Lys Gln Gly Arg Thr Thr Gly Asn Ser
    130                 135                 140

Cys Gly Val Thr Trp Gly Pro Gly Glu Ser Pro Gly Thr Leu Val Met
145                 150                 155                 160

Gln Val Cys Gly Gly Pro Gly Asp Ser Gly Ala Pro Val Thr Val Asp
                165                 170                 175

Asn Leu Leu Val Gly Met Ile His Gly Ala Phe Ser Asp Asn Leu Pro
                180                 185                 190

Ser Cys Ile Thr Lys Tyr Ile Pro Leu His Thr Pro Ala Val Val Met
    195                 200                 205

Ser Ile Asn Ala Asp Leu Ala Asp Ile Asn Ala Lys Asn Arg Pro Gly
    210                 215                 220

Ala Gly Phe Val Pro Val Pro Ala
225                 230

<210> SEQ ID NO 28
<211> LENGTH: 294
<212> TYPE: PRT
<213> ORGANISM: Mycobacterium tuberculosis

<400> SEQUENCE: 28

Met Leu Met Pro Glu Met Asp Arg Arg Met Met Met Ala Gly
1               5                  10                  15

Phe Gly Ala Leu Ala Ala Ala Leu Pro Ala Thr Ala Trp Ala Asp
                20                  25                  30

Pro Ser Arg Pro Ala Ala Pro Ala Gly Pro Thr Pro Ala Pro Ala Ala
                35                  40                  45

Pro Ala Ala Ala Thr Gly Gly Leu Leu Phe His Asp Glu Phe Asp Gly
    50                  55                  60

Pro Ala Gly Ser Val Pro Asp Pro Ser Lys Trp Gln Val Ser Asn His
```

```
                65                  70                  75                  80
Arg Thr Pro Ile Lys Asn Pro Val Gly Phe Asp Arg Pro Gln Phe Phe
                    85                  90                  95

Gly Gln Tyr Arg Asp Ser Arg Gln Asn Val Phe Leu Asp Gly Asn Ser
                    100                 105                 110

Asn Leu Val Leu Arg Ala Thr Arg Glu Gly Asn Arg Tyr Phe Gly Gly
                    115                 120                 125

Leu Val His Gly Leu Trp Arg Gly Ile Gly Thr Thr Trp Glu Ala
                    130                 135                 140

Arg Ile Lys Phe Asn Cys Leu Ala Pro Gly Met Trp Pro Ala Trp Trp
145                 150                 155                 160

Leu Ser Asn Asp Asp Pro Gly Arg Ser Gly Glu Ile Asp Leu Ile Glu
                    165                 170                 175

Trp Tyr Gly Asn Gly Thr Trp Pro Ser Gly Thr Thr Val His Ala Asn
                    180                 185                 190

Pro Asp Gly Thr Ala Phe Glu Thr Cys Pro Ile Gly Val Asp Gly Gly
                    195                 200                 205

Trp His Asn Trp Arg Val Thr Trp Asn Pro Ser Gly Met Tyr Phe Trp
                    210                 215                 220

Leu Asp Tyr Ala Asp Gly Ile Glu Pro Tyr Phe Ser Val Pro Ala Thr
225                 230                 235                 240

Gly Ile Glu Asp Leu Asn Glu Pro Ile Arg Glu Trp Pro Phe Asn Asp
                    245                 250                 255

Pro Gly Tyr Lys Val Phe Pro Val Leu Asn Leu Ala Val Gly Gly Ser
                    260                 265                 270

Gly Gly Gly Asp Pro Ala Thr Gly Ser Tyr Pro Gln Glu Met Leu Val
                    275                 280                 285

Asp Trp Val Arg Val Phe
                    290

<210> SEQ ID NO 29
<211> LENGTH: 379
<212> TYPE: PRT
<213> ORGANISM: Mycobacterium tuberculosis

<400> SEQUENCE: 29

Val His Arg Arg Thr Ala Leu Lys Leu Pro Leu Leu Leu Ala Ala Gly
1               5                   10                  15

Thr Val Leu Gly Gln Ala Pro Arg Ala Ala Glu Glu Pro Gly Arg
                    20                  25                  30

Trp Ser Ala Asp Arg Ala His Arg Trp Tyr Gln Ala His Gly Trp Leu
                    35                  40                  45

Val Gly Ala Asn Tyr Ile Thr Ser Asn Ala Ile Asn Gln Leu Glu Met
                    50                  55                  60

Phe Gln Pro Gly Thr Tyr Asp Pro Arg Arg Ile Asp Asn Glu Leu Gly
65                  70                  75                  80

Leu Ala Arg Phe His Gly Phe Asn Thr Val Arg Val Phe Leu His Asp
                    85                  90                  95

Leu Leu Trp Ala Gln Asp Ala Pro Gly Phe Gln Thr Arg Leu Ala Gln
                    100                 105                 110

Phe Val Ala Ile Ala Ala Arg Tyr His Ile Lys Pro Leu Phe Val Leu
                    115                 120                 125

Phe Asp Ser Cys Trp Asp Pro Leu Pro Arg Pro Gly Arg Gln Arg Ala
                    130                 135                 140
```

```
Pro Arg Ala Gly Val His Asn Ser Gly Trp Val Gln Ser Pro Gly Ala
145                 150                 155                 160

Glu Arg Leu Asp Asp Arg Arg Tyr Ala Ser Thr Leu Tyr Asn Tyr Val
                165                 170                 175

Thr Gly Val Leu Gly Gln Phe Arg Asn Asp Asp Arg Val Leu Gly Trp
            180                 185                 190

Asp Leu Trp Asn Glu Pro Asp Asn Pro Ala Arg Val Tyr Arg Lys Val
        195                 200                 205

Glu Arg Lys Asp Lys Leu Glu Arg Val Ala Glu Leu Leu Pro Gln Val
    210                 215                 220

Phe Arg Trp Ala Arg Thr Val Asp Pro Val Gln Pro Leu Thr Ser Gly
225                 230                 235                 240

Val Trp Gln Gly Asn Trp Gly Asp Pro Gly Arg Arg Ser Thr Ile Ser
                245                 250                 255

Ala Ile Gln Leu Asp Asn Ala Asp Val Ile Thr Phe His Ser Tyr Ala
            260                 265                 270

Ala Pro Ala Glu Phe Glu Gly Arg Ile Ala Glu Leu Ala Pro Leu Gln
        275                 280                 285

Arg Pro Ile Leu Cys Thr Glu Tyr Leu Ala Arg Ser Gln Gly Ser Thr
    290                 295                 300

Val Glu Gly Ile Leu Pro Ile Ala Lys Arg His Asn Val Gly Ala Phe
305                 310                 315                 320

Asn Trp Gly Leu Val Ala Gly Lys Thr Gln Thr Tyr Leu Pro Trp Asp
                325                 330                 335

Ser Trp Asp His Pro Tyr Arg Ala Pro Pro Lys Val Trp Phe His Asp
            340                 345                 350

Leu Leu His Pro Asn Gly Arg Pro Tyr Arg Asp Gly Glu Val Gln Thr
        355                 360                 365

Ile Arg Lys Leu Asn Gly Met Pro Ser Gln Asp
    370                 375

<210> SEQ ID NO 30
<211> LENGTH: 285
<212> TYPE: PRT
<213> ORGANISM: Mycobacterium tuberculosis

<400> SEQUENCE: 30

Val Ser Thr Tyr Gly Trp Arg Ala Tyr Ala Leu Pro Val Leu Met Val
1               5                   10                  15

Leu Thr Thr Val Val Tyr Gln Thr Val Thr Gly Thr Ser Thr Pro
            20                  25                  30

Arg Pro Ala Ala Ala Gln Thr Val Arg Asp Ser Pro Ala Ile Gly Val
        35                  40                  45

Val Gly Thr Ala Ile Leu Asp Ala Pro Pro Arg Gly Leu Ala Val Phe
    50                  55                  60

Asp Ala Asn Leu Pro Ala Gly Thr Leu Pro Asp Gly Gly Pro Phe Thr
65                  70                  75                  80

Glu Ala Gly Asp Lys Thr Trp Arg Val Val Pro Gly Thr Thr Pro Gln
                85                  90                  95

Val Gly Gln Gly Thr Val Lys Val Phe Arg Tyr Thr Val Glu Ile Glu
            100                 105                 110

Asn Gly Leu Asp Pro Thr Met Tyr Gly Gly Asp Asn Ala Phe Ala Gln
        115                 120                 125

Met Val Asp Gln Thr Leu Thr Asn Pro Lys Gly Trp Thr His Asn Pro
    130                 135                 140
```

```
Gln Phe Ala Phe Val Arg Ile Asp Ser Gly Lys Pro Asp Phe Arg Ile
145                 150                 155                 160

Ser Leu Val Ser Pro Thr Thr Val Arg Gly Gly Cys Gly Tyr Glu Phe
            165                 170                 175

Arg Leu Glu Thr Ser Cys Tyr Asn Pro Ser Phe Gly Gly Met Asp Arg
            180                 185                 190

Gln Ser Arg Val Phe Ile Asn Glu Ala Arg Trp Val Arg Gly Ala Val
            195                 200                 205

Pro Phe Glu Gly Asp Val Gly Ser Tyr Arg Gln Tyr Val Ile Asn His
            210                 215                 220

Glu Val Gly His Ala Ile Gly Tyr Leu Arg His Glu Pro Cys Asp Gln
225                 230                 235                 240

Gln Gly Gly Leu Ala Pro Val Met Met Gln Gln Thr Phe Ser Thr Ser
            245                 250                 255

Asn Asp Asp Ala Ala Lys Phe Asp Pro Asp Phe Val Lys Ala Asp Gly
            260                 265                 270

Lys Thr Cys Arg Phe Asn Pro Trp Pro Tyr Pro Ile Pro
            275                 280                 285

<210> SEQ ID NO 31
<211> LENGTH: 456
<212> TYPE: PRT
<213> ORGANISM: Mycobacterium tuberculosis

<400> SEQUENCE: 31

Met Arg Pro Tyr Tyr Ile Ala Ile Val Gly Ser Gly Pro Ser Ala Phe
1               5                   10                  15

Phe Ala Ala Ser Leu Leu Lys Ala Ala Asp Thr Thr Glu Asp Leu
            20                  25                  30

Asp Met Ala Val Asp Met Leu Glu Met Leu Pro Thr Pro Trp Gly Leu
            35                  40                  45

Val Arg Ser Gly Val Ala Pro Asp His Pro Lys Ile Lys Ser Ile Ser
50                  55                  60

Lys Gln Phe Glu Lys Thr Ala Glu Asp Pro Arg Phe Arg Phe Phe Gly
65                  70                  75                  80

Asn Val Val Gly Glu His Val Gln Pro Gly Glu Leu Ser Glu Arg
            85                  90                  95

Tyr Asp Ala Val Ile Tyr Ala Val Gly Ala Gln Ser Asp Arg Met Leu
            100                 105                 110

Asn Ile Pro Gly Glu Asp Leu Pro Gly Ser Ile Ala Ala Val Asp Phe
            115                 120                 125

Val Gly Trp Tyr Asn Ala His Pro His Phe Glu Gln Val Ser Pro Asp
            130                 135                 140

Leu Ser Gly Ala Arg Ala Val Val Ile Gly Asn Gly Asn Val Ala Leu
145                 150                 155                 160

Asp Val Ala Arg Ile Leu Leu Thr Asp Pro Asp Val Leu Ala Arg Thr
            165                 170                 175

Asp Ile Ala Asp His Ala Leu Glu Ser Leu Arg Pro Arg Gly Ile Gln
            180                 185                 190

Glu Val Val Ile Val Gly Arg Arg Gly Pro Leu Gln Ala Ala Phe Thr
            195                 200                 205

Thr Leu Glu Leu Arg Glu Leu Ala Asp Leu Asp Gly Val Asp Val Val
            210                 215                 220

Ile Asp Pro Ala Glu Leu Asp Gly Ile Thr Asp Glu Asp Ala Ala Ala
```

```
                    225                 230                 235                 240
Val Gly Lys Val Cys Lys Gln Asn Ile Lys Val Leu Arg Gly Tyr Ala
                245                 250                 255

Asp Arg Glu Pro Arg Pro Gly His Arg Arg Met Val Phe Arg Phe Leu
            260                 265                 270

Thr Ser Pro Ile Glu Ile Lys Gly Lys Arg Lys Val Glu Arg Ile Val
        275                 280                 285

Leu Gly Arg Asn Glu Leu Val Ser Asp Gly Ser Gly Arg Val Ala Ala
    290                 295                 300

Lys Asp Thr Gly Glu Arg Glu Leu Pro Ala Gln Leu Val Val Arg
305                 310                 315                 320

Ser Val Gly Tyr Arg Gly Val Pro Thr Pro Gly Leu Pro Phe Asp Asp
                325                 330                 335

Gln Ser Gly Thr Ile Pro Asn Val Gly Arg Ile Asn Gly Ser Pro
            340                 345                 350

Asn Glu Tyr Val Val Gly Trp Ile Lys Arg Gly Pro Thr Gly Val Ile
        355                 360                 365

Gly Thr Asn Lys Lys Asp Ala Gln Asp Thr Val Asp Thr Leu Ile Lys
    370                 375                 380

Asn Leu Gly Asn Ala Lys Glu Gly Ala Glu Cys Lys Ser Phe Pro Glu
385                 390                 395                 400

Asp His Ala Asp Gln Val Ala Asp Trp Leu Ala Ala Arg Gln Pro Lys
                405                 410                 415

Leu Val Thr Ser Ala His Trp Gln Val Ile Asp Ala Phe Glu Arg Ala
            420                 425                 430

Ala Gly Glu Pro His Gly Arg Pro Arg Val Lys Leu Ala Ser Leu Ala
        435                 440                 445

Glu Leu Leu Arg Ile Gly Leu Gly
    450                 455

<210> SEQ ID NO 32
<211> LENGTH: 448
<212> TYPE: PRT
<213> ORGANISM: Mycobacterium tuberculosis

<400> SEQUENCE: 32

Val Thr Asn Pro Pro Trp Thr Val Asp Val Val Val Gly Ala Gly
  1               5                  10                  15

Phe Ala Gly Leu Ala Ala Ala Arg Glu Leu Thr Arg Gln Gly His Glu
                20                  25                  30

Val Leu Val Phe Glu Gly Arg Asp Arg Val Gly Gly Arg Ser Leu Thr
            35                  40                  45

Gly Arg Val Ala Gly Val Pro Ala Asp Met Gly Gly Ser Phe Ile Gly
    50                  55                  60

Pro Thr Gln Asp Ala Val Leu Ala Leu Ala Thr Glu Leu Gly Ile Pro
65                  70                  75                  80

Thr Thr Pro Thr His Arg Asp Gly Arg Asn Val Ile Gln Trp Arg Gly
                85                  90                  95

Ser Ala Arg Ser Tyr Arg Gly Thr Ile Pro Lys Leu Ser Leu Thr Gly
            100                 105                 110

Leu Ile Asp Ile Gly Arg Leu Arg Trp Gln Phe Glu Arg Ile Ala Arg
        115                 120                 125

Gly Val Pro Val Ala Ala Pro Trp Asp Ala Arg Arg Ala Arg Glu Leu
    130                 135                 140
```

-continued

Asp Asp Val Ser Leu Gly Glu Trp Leu Arg Leu Val Arg Ala Thr Ser
145                 150                 155                 160

Ser Ser Arg Asn Leu Met Ala Ile Met Thr Arg Val Thr Trp Gly Cys
                165                 170                 175

Glu Pro Asp Asp Val Ser Met Leu His Ala Ala Arg Tyr Val Arg Ala
            180                 185                 190

Ala Gly Gly Leu Asp Arg Leu Leu Asp Val Lys Asn Gly Ala Gln Gln
        195                 200                 205

Asp Arg Val Pro Gly Gly Thr Gln Gln Ile Ala Gln Ala Ala Ala Ala
210                 215                 220

Gln Leu Gly Ala Arg Val Leu Leu Asn Ala Ala Val Arg Arg Ile Asp
225                 230                 235                 240

Arg His Gly Ala Gly Val Thr Val Thr Ser Asp Gln Gly Gln Ala Glu
                245                 250                 255

Ala Gly Phe Val Ile Val Ala Ile Pro Pro Ala His Arg Val Ala Ile
            260                 265                 270

Glu Phe Asp Pro Pro Leu Pro Pro Glu Tyr Gln Gln Leu Ala His His
        275                 280                 285

Trp Pro Gln Gly Arg Leu Ser Lys Ala Tyr Ala Ala Tyr Ser Thr Pro
290                 295                 300

Phe Trp Arg Ala Ser Gly Tyr Ser Gly Gln Ala Leu Ser Asp Glu Ala
305                 310                 315                 320

Pro Val Phe Ile Thr Phe Asp Val Ser Pro His Ala Asp Gly Pro Gly
                325                 330                 335

Ile Leu Met Gly Phe Val Asp Ala Arg Gly Phe Asp Ser Leu Pro Ile
            340                 345                 350

Glu Glu Arg Arg Arg Asp Ala Leu Arg Cys Phe Ala Ser Leu Phe Gly
        355                 360                 365

Asp Glu Ala Leu Asp Pro Leu Asp Tyr Val Asp Tyr Arg Trp Gly Thr
370                 375                 380

Glu Glu Phe Ala Pro Gly Gly Pro Thr Ala Ala Val Pro Pro Gly Ser
385                 390                 395                 400

Trp Thr Lys Tyr Gly His Trp Leu Arg Glu Pro Val Gly Pro Ile His
                405                 410                 415

Trp Ala Ser Thr Glu Thr Ala Asp Glu Trp Thr Gly Tyr Phe Asp Gly
            420                 425                 430

Ala Val Arg Ser Gly Gln Arg Ala Ala Glu Val Ala Ala Leu Leu
        435                 440                 445

<210> SEQ ID NO 33
<211> LENGTH: 112
<212> TYPE: PRT
<213> ORGANISM: Mycobacterium tuberculosis

<400> SEQUENCE: 33

Met Lys Gly Thr Lys Leu Ala Val Val Gly Met Thr Val Ala Ala
1               5                   10                  15

Val Ser Leu Ala Ala Pro Ala Gln Ala Asp Asp Tyr Asp Ala Pro Phe
                20                  25                  30

Asn Asn Thr Ile His Arg Phe Gly Ile Tyr Gly Pro Gln Asp Tyr Asn
            35                  40                  45

Ala Trp Leu Ala Lys Ile Ser Cys Glu Arg Leu Ser Arg Gly Val Asp
        50                  55                  60

Gly Asp Ala Tyr Lys Ser Ala Thr Phe Leu Gln Arg Asn Leu Pro Arg
65                  70                  75                  80

-continued

Gly Thr Thr Gln Gly Gln Ala Phe Gln Phe Leu Gly Ala Ala Ile Asp
                85                  90                  95

His Tyr Cys Pro Glu His Val Gly Val Leu Gln Arg Ala Gly Thr Arg
            100                 105                 110

<210> SEQ ID NO 34
<211> LENGTH: 148
<212> TYPE: PRT
<213> ORGANISM: Mycobacterium tuberculosis

<400> SEQUENCE: 34

Met Lys Ala Leu Val Ala Val Ser Ala Val Ala Val Ala Leu Leu
1               5                   10                  15

Gly Val Ser Ser Ala Gln Ala Asp Pro Glu Ala Asp Pro Gly Ala Gly
                20                  25                  30

Glu Ala Asn Tyr Gly Gly Pro Pro Ser Ser Pro Arg Leu Val Asp His
            35                  40                  45

Thr Glu Trp Ala Gln Trp Gly Ser Leu Pro Ser Leu Arg Val Tyr Pro
        50                  55                  60

Ser Gln Val Gly Arg Thr Ala Ser Arg Arg Leu Gly Met Ala Ala Ala
65                  70                  75                  80

Asp Ala Ala Trp Ala Glu Val Leu Ala Leu Ser Pro Glu Ala Asp Thr
                85                  90                  95

Ala Gly Met Arg Ala Gln Phe Ile Cys His Trp Gln Tyr Ala Glu Ile
            100                 105                 110

Arg Gln Pro Gly Lys Pro Ser Trp Asn Leu Glu Pro Trp Arg Pro Val
        115                 120                 125

Val Asp Asp Ser Glu Met Leu Ala Ser Gly Cys Asn Pro Gly Ser Pro
    130                 135                 140

Glu Glu Ser Phe
145

<210> SEQ ID NO 35
<211> LENGTH: 407
<212> TYPE: PRT
<213> ORGANISM: Mycobacterium tuberculosis

<400> SEQUENCE: 35

Met Ser Gly Arg His Arg Lys Pro Thr Thr Ser Asn Val Ser Val Ala
1               5                   10                  15

Lys Ile Ala Phe Thr Gly Ala Val Leu Gly Gly Gly Ile Ala Met
                20                  25                  30

Ala Ala Gln Ala Thr Ala Ala Thr Asp Gly Glu Trp Asp Gln Val Ala
            35                  40                  45

Arg Cys Glu Ser Gly Gly Asn Trp Ser Ile Asn Thr Gly Asn Gly Tyr
        50                  55                  60

Leu Gly Gly Leu Gln Phe Thr Gln Ser Thr Trp Ala Ala His Gly Gly
65                  70                  75                  80

Gly Glu Phe Ala Pro Ser Ala Gln Leu Ala Ser Arg Glu Gln Gln Ile
                85                  90                  95

Ala Val Gly Glu Arg Val Leu Ala Thr Gln Gly Arg Gly Ala Trp Pro
            100                 105                 110

Val Cys Gly Arg Gly Leu Ser Asn Ala Thr Pro Arg Glu Val Leu Pro
        115                 120                 125

Ala Ser Ala Ala Met Asp Ala Pro Leu Asp Ala Ala Val Asn Gly
    130                 135                 140

```
Glu Pro Ala Pro Leu Ala Pro Pro Ala Asp Pro Ala Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Pro Ala Asp Leu Ala Pro Pro Ala
            180                 185                 190

Pro Ala Asp Val Ala Pro Val Glu Leu Ala Val Asn Asp Leu Pro
        195                 200                 205

Ala Pro Leu Gly Glu Pro Leu Pro Ala Ala Pro Ala Asp Pro Ala Pro
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Ala Pro Leu Gly Glu Pro Leu Pro
                260                 265                 270

Ala Ala Pro Ala Glu Leu Ala Pro Pro Ala Asp Leu Ala Pro Ala Ser
            275                 280                 285

Ala Asp Leu Ala Pro Pro Ala Pro Ala Asp Leu Ala Pro Pro Ala Pro
        290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335

Gly Pro Val Gly Leu Ala Thr Asp Leu Glu Leu Pro Glu Pro Asp Pro
            340                 345                 350

Gln Pro Ala Asp Ala Pro Pro Gly Asp Val Thr Glu Ala Pro Ala
        355                 360                 365

Glu Thr Pro Gln Val Ser Asn Ile Ala Tyr Thr Lys Lys Leu Trp Gln
    370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405

<210> SEQ ID NO 36
<211> LENGTH: 167
<212> TYPE: PRT
<213> ORGANISM: Mycobacterium tuberculosis

<400> SEQUENCE: 36

Met Ser Gly His Arg Lys Lys Ala Met Leu Ala Leu Ala Ala Ala Ser
1               5                   10                  15

Leu Ala Ala Thr Leu Ala Pro Asn Ala Val Ala Ala Glu Pro Ser
            20                  25                  30

Trp Asn Gly Gln Tyr Leu Val Thr Leu Ser Ala Asn Ala Lys Thr Gly
        35                  40                  45

Thr Ser Met Ala Ala Asn Arg Pro Glu Tyr Pro His Lys Ala Asn Tyr
    50                  55                  60

Thr Phe Ser Ser Arg Cys Ala Ser Asp Val Cys Ile Ala Thr Val Val
65                  70                  75                  80

Asp Ala Pro Pro Pro Lys Asn Glu Phe Ile Pro Arg Pro Ile Glu Tyr
                85                  90                  95

Thr Trp Asn Gly Thr Gln Trp Val Arg Glu Ile Ser Trp Gln Trp Asp
```

-continued

Cys Leu Leu Pro Asp Gly Thr Ile Glu Tyr Ala Pro Ala Lys Ser Ile
115                 120                 125

Thr Ala Tyr Thr Pro Gly Gln Tyr Gly Ile Leu Thr Gly Val Phe His
130                 135                 140

Thr Asp Ile Ala Ser Gly Thr Cys Lys Gly Asn Val Asp Met Pro Val
145                 150                 155                 160

Ser Ala Lys Pro Ile Val Gly
                165

<210> SEQ ID NO 37
<211> LENGTH: 227
<212> TYPE: PRT
<213> ORGANISM: Mycobacterium tuberculosis

<400> SEQUENCE: 37

Met Arg Tyr Leu Ile Ala Thr Ala Val Leu Val Ala Val Val Leu Val
1               5                   10                  15

Gly Trp Pro Ala Ala Gly Ala Pro Pro Ser Cys Ala Gly Leu Gly Gly
                20                  25                  30

Thr Val Gln Ala Gly Gln Ile Cys His Val His Ala Ser Gly Pro Lys
            35                  40                  45

Tyr Met Leu Asp Met Thr Phe Pro Val Asp Tyr Pro Asp Gln Gln Ala
    50                  55                  60

Leu Thr Asp Tyr Ile Thr Gln Asn Arg Asp Gly Phe Val Asn Val Ala
65                  70                  75                  80

Gln Gly Ser Pro Leu Arg Asp Gln Pro Tyr Gln Met Asp Ala Thr Ser
                85                  90                  95

Glu Gln His Ser Ser Gly Gln Pro Pro Gln Ala Thr Arg Ser Val Val
            100                 105                 110

Leu Lys Phe Phe Gln Asp Leu Gly Gly Ala His Pro Ser Thr Trp Tyr
        115                 120                 125

Lys Ala Phe Asn Tyr Asn Leu Ala Thr Ser Gln Pro Ile Thr Phe Asp
    130                 135                 140

Thr Leu Phe Val Pro Gly Thr Thr Pro Leu Asp Ser Ile Tyr Pro Ile
145                 150                 155                 160

Val Gln Arg Glu Leu Ala Arg Gln Thr Gly Phe Gly Ala Ala Ile Leu
                165                 170                 175

Pro Ser Thr Gly Leu Asp Pro Ala His Tyr Gln Asn Phe Ala Ile Thr
            180                 185                 190

Asp Asp Ser Leu Ile Phe Tyr Phe Ala Gln Gly Glu Leu Leu Pro Ser
        195                 200                 205

Phe Val Gly Ala Cys Gln Ala Gln Val Pro Arg Ser Ala Ile Pro Pro
    210                 215                 220

Leu Ala Ile
225

<210> SEQ ID NO 38
<211> LENGTH: 172
<212> TYPE: PRT
<213> ORGANISM: Mycobacterium tuberculosis

<400> SEQUENCE: 38

Leu Lys Asn Ala Arg Thr Thr Leu Ile Ala Ala Ala Ile Ala Gly Thr
1               5                   10                  15

Leu Val Thr Thr Ser Pro Ala Gly Ile Ala Asn Ala Asp Asp Ala Gly

-continued

```
                    20                  25                  30

Leu Asp Pro Asn Ala Ala Gly Pro Asp Ala Val Gly Phe Asp Pro
                35                  40                  45

Asn Leu Pro Pro Ala Pro Asp Ala Ala Pro Val Asp Thr Pro Pro Ala
 50                  55                  60

Pro Glu Asp Ala Gly Phe Asp Pro Asn Leu Pro Pro Pro Leu Ala Pro
 65                  70                  75                  80

Asp Phe Leu Ser Pro Pro Ala Glu Glu Ala Pro Pro Val Pro Val Ala
                85                  90                  95

Tyr Ser Val Asn Trp Asp Ala Ile Ala Gln Cys Glu Ser Gly Gly Asn
                100                 105                 110

Trp Ser Ile Asn Thr Gly Asn Gly Tyr Tyr Gly Gly Leu Arg Phe Thr
                115                 120                 125

Ala Gly Thr Trp Arg Ala Asn Gly Gly Ser Gly Ser Ala Ala Asn Ala
                130                 135                 140

Ser Arg Glu Glu Gln Ile Arg Val Ala Glu Asn Val Leu Arg Ser Gln
145                 150                 155                 160

Gly Ile Arg Ala Trp Pro Val Cys Gly Arg Arg Gly
                165                 170

<210> SEQ ID NO 39
<211> LENGTH: 508
<212> TYPE: PRT
<213> ORGANISM: Mycobacterium tuberculosis

<400> SEQUENCE: 39

Met Ser Thr Ile Phe Asp Ile Arg Ser Leu Arg Leu Pro Lys Leu Ser
 1               5                  10                  15

Ala Lys Val Val Val Gly Gly Leu Val Val Val Leu Ala Val Val
                20                  25                  30

Ala Ala Ala Ala Gly Ala Arg Leu Tyr Arg Lys Leu Thr Thr Thr Thr
                35                  40                  45

Val Val Ala Tyr Phe Ser Glu Ala Leu Ala Leu Tyr Pro Gly Asp Lys
 50                  55                  60

Val Gln Ile Met Gly Val Arg Val Gly Ser Ile Asp Lys Ile Glu Pro
 65                  70                  75                  80

Ala Gly Asp Lys Met Arg Val Thr Leu His Tyr Ser Asn Lys Tyr Gln
                85                  90                  95

Val Pro Ala Thr Ala Thr Ala Ser Ile Leu Asn Pro Ser Leu Val Ala
                100                 105                 110

Ser Arg Thr Ile Gln Leu Ser Pro Pro Tyr Thr Gly Gly Pro Val Leu
                115                 120                 125

Gln Asp Gly Ala Val Ile Pro Ile Glu Arg Thr Gln Val Pro Val Glu
130                 135                 140

Trp Asp Gln Leu Arg Asp Ser Ile Asn Gly Ile Leu Arg Gln Leu Gly
145                 150                 155                 160

Pro Thr Glu Arg Gln Pro Lys Gly Pro Phe Gly Asp Leu Ile Glu Ser
                165                 170                 175

Ala Ala Asp Asn Leu Ala Gly Lys Gly Arg Gln Leu Asn Glu Thr Leu
                180                 185                 190

Asn Ser Leu Ser Gln Ala Leu Thr Ala Leu Asn Glu Gly Arg Gly Asp
                195                 200                 205

Phe Val Ala Ile Thr Arg Ser Leu Ala Leu Phe Val Ser Ala Leu Tyr
                210                 215                 220
```

-continued

Gln Asn Asp Gln Gln Phe Val Ala Leu Asn Glu Asn Leu Ala Glu Phe
225                 230                 235                 240

Thr Asp Trp Phe Thr Lys Ser Asp His Asp Leu Ala Asp Thr Val Glu
            245                 250                 255

Arg Ile Asp Asp Val Leu Gly Thr Val Arg Lys Phe Val Ser Asp Asn
        260                 265                 270

Arg Ser Val Leu Ala Ala Asp Val Asn Asn Leu Ala Asp Ala Thr Thr
    275                 280                 285

Thr Leu Val Gln Pro Glu Pro Arg Asp Gly Leu Glu Thr Ala Leu His
290                 295                 300

Val Leu Pro Thr Tyr Ala Ser Asn Phe Asn Asn Leu Tyr Tyr Pro Leu
305                 310                 315                 320

His Ser Ser Leu Val Gly Gln Phe Val Phe Pro Asn Phe Ala Asn Pro
                325                 330                 335

Ile Gln Leu Ile Cys Ser Ala Ile Gln Ala Gly Ser Arg Leu Gly Tyr
            340                 345                 350

Gln Glu Ser Ala Glu Leu Cys Ala Gln Tyr Leu Ala Pro Val Leu Asp
        355                 360                 365

Ala Leu Lys Phe Asn Tyr Leu Pro Phe Gly Ser Asn Pro Phe Ser Ser
370                 375                 380

Ala Ala Thr Leu Pro Lys Glu Val Ala Tyr Ser Glu Glu Arg Leu Arg
385                 390                 395                 400

Pro Pro Pro Gly Tyr Lys Asp Thr Thr Val Pro Gly Ile Phe Ser Arg
                405                 410                 415

Asp Thr Pro Phe Ser His Gly Asn His Glu Pro Gly Trp Val Val Ala
            420                 425                 430

Pro Gly Met Gln Gly Met Gln Val Gln Pro Phe Thr Ala Asn Met Leu
        435                 440                 445

Thr Pro Glu Ser Leu Ala Glu Leu Leu Gly Gly Pro Asp Ile Ala Pro
450                 455                 460

Pro Pro Pro Gly Thr Asn Leu Pro Gly Pro Pro Asn Ala Tyr Asp Glu
465                 470                 475                 480

Ser Asn Pro Leu Pro Pro Trp Tyr Pro Gln Pro Ala Ser Leu Pro
                485                 490                 495

Ala Ala Gly Ala Thr Gly Gln Pro Gly Pro Gly Gln
            500                 505

<210> SEQ ID NO 40
<211> LENGTH: 230
<212> TYPE: PRT
<213> ORGANISM: Mycobacterium tuberculosis

<400> SEQUENCE: 40

Met Lys Arg Ser Met Lys Ser Gly Ser Phe Ala Ile Gly Leu Ala Met
1               5                   10                  15

Met Leu Ala Pro Met Val Ala Ala Pro Gly Leu Ala Ala Asp Pro
            20                  25                  30

Ala Thr Arg Pro Val Asp Tyr Gln Gln Ile Thr Asp Val Val Ile Ala
        35                  40                  45

Arg Gly Leu Ser Gln Arg Gly Val Pro Phe Ser Trp Ala Gly Gly Gly
    50                  55                  60

Ile Ser Gly Pro Thr Arg Gly Thr Gly Ile Asn Thr Val Gly
65                  70                  75                  80

Phe Asp Ala Ser Gly Leu Ile Gln Tyr Ala Tyr Ala Gly Ala Gly Leu
                85                  90                  95

```
Lys Leu Pro Arg Ser Ser Gly Gln Met Tyr Lys Val Gly Gln Lys Val
                100                 105                 110

Leu Pro Gln Gln Ala Arg Lys Gly Asp Leu Ile Phe Tyr Gly Pro Glu
            115                 120                 125

Gly Thr Gln Ser Val Ala Leu Tyr Leu Gly Lys Gly Gln Met Leu Glu
        130                 135                 140

Val Gly Asp Val Val Gln Val Ser Pro Val Arg Thr Asn Gly Met Thr
145                 150                 155                 160

Pro Tyr Leu Val Arg Val Leu Gly Thr Gln Pro Thr Pro Val Gln Gln
                165                 170                 175

Ala Pro Val Gln Pro Ala Pro Val Gln Gln Ala Pro Val Gln Gln Ala
            180                 185                 190

Pro Val Gln Gln Ala Pro Val Gln Gln Ala Pro Val Gln Gln Ala Pro
        195                 200                 205

Val Gln Gln Ala Pro Val Gln Gln Ala Pro Val Gln Pro Pro Pro Phe
    210                 215                 220

Gly Thr Ala Arg Ser Arg
225                 230

<210> SEQ ID NO 41
<211> LENGTH: 111
<212> TYPE: PRT
<213> ORGANISM: Mycobacterium tuberculosis

<400> SEQUENCE: 41

Met Phe Thr Arg Arg Phe Ala Ala Ser Met Val Gly Thr Thr Leu Thr
1               5                   10                  15

Ala Ala Thr Leu Gly Leu Ala Ala Leu Gly Phe Ala Gly Thr Ala Ser
            20                  25                  30

Ala Ser Ser Thr Asp Glu Ala Phe Leu Ala Gln Leu Gln Ala Asp Gly
        35                  40                  45

Ile Thr Pro Pro Ser Ala Ala Arg Ala Ile Lys Asp Ala His Ala Val
    50                  55                  60

Cys Asp Ala Leu Asp Glu Gly His Ser Ala Lys Ala Val Ile Lys Ala
65                  70                  75                  80

Val Ala Lys Ala Thr Gly Leu Ser Ala Lys Gly Ala Lys Thr Phe Ala
                85                  90                  95

Val Asp Ala Ala Ser Ala Tyr Cys Pro Gln Tyr Val Thr Ser Ser
            100                 105                 110

<210> SEQ ID NO 42
<211> LENGTH: 520
<212> TYPE: PRT
<213> ORGANISM: Mycobacterium tuberculosis

<400> SEQUENCE: 42

Met Ala Ala Met Trp Arg Arg Arg Pro Leu Ser Ser Ala Leu Leu Ser
1               5                   10                  15

Phe Gly Leu Leu Leu Gly Gly Leu Pro Leu Ala Ala Pro Pro Leu Ala
            20                  25                  30

Gly Ala Thr Glu Glu Pro Gly Ala Gly Gln Thr Pro Gly Ala Pro Val
        35                  40                  45

Val Ala Pro Gln Gln Ser Trp Asn Ser Cys Arg Glu Phe Ile Ala Asp
    50                  55                  60

Thr Ser Glu Ile Arg Thr Ala Arg Cys Ala Thr Val Ser Val Pro Val
65                  70                  75                  80
```

```
Asp Tyr Asp Gln Pro Gly Gly Thr Gln Ala Lys Leu Ala Val Ile Arg
                85                  90                  95

Val Pro Ala Thr Gly Gln Arg Phe Gly Ala Leu Leu Val Asn Pro Gly
            100                 105                 110

Gly Pro Gly Ala Ser Ala Val Asp Met Val Ala Ala Met Ala Pro Ala
        115                 120                 125

Ile Ala Asp Thr Asp Ile Leu Arg His Phe Asp Leu Val Gly Phe Asp
    130                 135                 140

Pro Arg Gly Val Gly His Ser Thr Pro Ala Leu Arg Cys Arg Thr Asp
145                 150                 155                 160

Ala Glu Phe Asp Ala Tyr Arg Arg Asp Pro Met Ala Asp Tyr Ser Pro
                165                 170                 175

Ala Gly Val Thr His Val Glu Gln Val Tyr Arg Gln Leu Ala Gln Asp
            180                 185                 190

Cys Val Asp Arg Met Gly Phe Ser Phe Leu Ala Asn Ile Gly Thr Ala
        195                 200                 205

Ser Val Ala Arg Asp Met Asp Met Val Arg Gln Ala Leu Gly Asp Asp
    210                 215                 220

Gln Ile Asn Tyr Leu Gly Tyr Ser Tyr Gly Thr Glu Leu Gly Thr Ala
225                 230                 235                 240

Tyr Leu Glu Arg Phe Gly Thr His Val Arg Ala Met Val Leu Asp Gly
                245                 250                 255

Ala Ile Asp Pro Ala Val Ser Pro Ile Glu Glu Ser Ile Ser Gln Met
            260                 265                 270

Ala Gly Phe Gln Thr Ala Phe Asn Asp Tyr Ala Ala Asp Cys Ala Arg
        275                 280                 285

Ser Pro Ala Cys Pro Leu Gly Thr Asp Ser Ala Gln Trp Val Asn Arg
    290                 295                 300

Tyr His Ala Leu Val Asp Pro Leu Val Gln Lys Pro Gly Lys Thr Ser
305                 310                 315                 320

Asp Pro Arg Gly Leu Ser Tyr Ala Asp Ala Thr Thr Gly Thr Ile Asn
                325                 330                 335

Ala Leu Tyr Ser Pro Gln Arg Trp Lys Tyr Leu Thr Ser Gly Leu Leu
            340                 345                 350

Gly Leu Gln Arg Gly Ser Asp Ala Gly Asp Leu Leu Val Leu Ala Asp
        355                 360                 365

Asp Tyr Asp Gly Arg Asp Ala Asp Gly His Tyr Ser Asn Asp Gln Asp
    370                 375                 380

Ala Phe Asn Ala Val Arg Cys Val Asp Ala Pro Thr Ala Asp Pro
385                 390                 395                 400

Ala Ala Trp Val Ala Ala Asp Gln Arg Ile Arg Gln Val Ala Pro Phe
                405                 410                 415

Leu Ser Tyr Gly Gln Phe Thr Gly Ser Ala Pro Arg Asp Leu Cys Ala
            420                 425                 430

Leu Trp Pro Val Pro Ala Thr Ser Thr Pro His Pro Ala Ala Pro Ala
        435                 440                 445

Gly Ala Gly Lys Val Val Val Ser Thr Thr His Asp Pro Ala Thr
    450                 455                 460

Pro Tyr Gln Ser Gly Val Asp Leu Ala Arg Gln Leu Gly Ala Pro Leu
465                 470                 475                 480

Ile Thr Phe Asp Gly Thr Gln His Thr Ala Val Phe Asp Gly Asn Gln
                485                 490                 495
```

```
Cys Val Asp Ser Ala Val Met His Tyr Phe Leu Asp Gly Thr Leu Pro
                500                 505                 510

Pro Thr Ser Leu Arg Cys Ala Pro
            515                 520

<210> SEQ ID NO 43
<211> LENGTH: 136
<212> TYPE: PRT
<213> ORGANISM: Mycobacterium tuberculosis

<400> SEQUENCE: 43

Met Lys Thr Gly Thr Ala Thr Thr Arg Arg Leu Leu Ala Val Leu
  1               5                  10                  15

Ile Ala Leu Ala Leu Pro Gly Ala Ala Val Ala Leu Leu Ala Glu Pro
                 20                  25                  30

Ser Ala Thr Gly Ala Ser Asp Pro Cys Ala Ala Ser Glu Val Ala Arg
                 35                  40                  45

Thr Val Gly Ser Val Ala Lys Ser Met Gly Asp Tyr Leu Asp Ser His
             50                  55                  60

Pro Glu Thr Asn Gln Val Met Thr Ala Val Leu Gln Gln Gln Val Gly
 65                  70                  75                  80

Pro Gly Ser Val Ala Ser Leu Lys Ala His Phe Glu Ala Asn Pro Lys
                 85                  90                  95

Val Ala Ser Asp Leu His Ala Leu Ser Gln Pro Leu Thr Asp Leu Ser
                100                 105                 110

Thr Arg Cys Ser Leu Pro Ile Ser Gly Leu Gln Ala Ile Gly Leu Met
            115                 120                 125

Gln Ala Val Gln Gly Ala Arg Arg
        130                 135

<210> SEQ ID NO 44
<211> LENGTH: 148
<212> TYPE: PRT
<213> ORGANISM: Mycobacterium tuberculosis

<400> SEQUENCE: 44

Met Ser Arg Leu Ser Ser Ile Leu Arg Ala Gly Ala Ala Phe Leu Val
  1               5                  10                  15

Leu Gly Ile Ala Ala Ala Thr Phe Pro Gln Ser Ala Ala Ala Asp Ser
                 20                  25                  30

Thr Glu Asp Phe Pro Ile Pro Arg Arg Met Ile Ala Thr Thr Cys Asp
                 35                  40                  45

Ala Glu Gln Tyr Leu Ala Ala Val Arg Asp Thr Ser Pro Val Tyr Tyr
             50                  55                  60

Gln Arg Tyr Met Ile Asp Phe Asn Asn His Ala Asn Leu Gln Gln Ala
 65                  70                  75                  80

Thr Ile Asn Lys Ala His Trp Phe Phe Ser Leu Ser Pro Ala Glu Arg
                 85                  90                  95

Arg Asp Tyr Ser Glu His Phe Tyr Asn Gly Asp Pro Leu Thr Phe Ala
                100                 105                 110

Trp Val Asn His Met Lys Ile Phe Phe Asn Asn Lys Gly Val Val Ala
            115                 120                 125

Lys Gly Thr Glu Val Cys Asn Gly Tyr Pro Ala Gly Asp Met Ser Val
        130                 135                 140

Trp Asn Trp Ala
145
```

<210> SEQ ID NO 45
<211> LENGTH: 145
<212> TYPE: PRT
<213> ORGANISM: Mycobacterium tuberculosis

<400> SEQUENCE: 45

Val Thr Lys Arg Thr Ile Thr Pro Met Thr Ser Met Gly Asp Leu Leu
1               5                   10                  15

Gly Pro Glu Pro Ile Leu Leu Pro Gly Asp Ser Asp Ala Glu Ala Glu
            20                  25                  30

Leu Leu Ala Asn Glu Ser Pro Ser Ile Val Ala Ala His Pro Ser
        35                  40                  45

Ala Ser Val Ala Trp Ala Val Leu Ala Glu Gly Ala Leu Ala Asp Asp
    50                  55                  60

Lys Thr Val Thr Ala Tyr Ala Tyr Ala Arg Thr Gly Tyr His Arg Gly
65                  70                  75                  80

Leu Asp Gln Leu Arg Arg His Gly Trp Lys Gly Phe Gly Pro Val Pro
                85                  90                  95

Tyr Ser His Gln Pro Asn Arg Gly Phe Leu Arg Cys Val Ala Ala Leu
            100                 105                 110

Ala Arg Ala Ala Ala Ile Gly Glu Thr Asp Glu Tyr Gly Arg Cys
        115                 120                 125

Leu Asp Leu Leu Asp Asp Cys Asp Pro Ala Ala Arg Pro Ala Leu Gly
    130                 135                 140

Leu
145

<210> SEQ ID NO 46
<211> LENGTH: 143
<212> TYPE: PRT
<213> ORGANISM: Mycobacterium tuberculosis

<400> SEQUENCE: 46

Val Ile Ile Pro Asp Ile Asn Leu Leu Leu Tyr Ala Val Ile Thr Gly
1               5                   10                  15

Phe Pro Gln His Arg Arg Ala His Ala Trp Trp Gln Asp Thr Val Asn
            20                  25                  30

Gly His Thr Arg Ile Gly Leu Thr Tyr Pro Ala Leu Phe Gly Phe Leu
        35                  40                  45

Arg Ile Ala Thr Ser Ala Arg Val Leu Ala Ala Pro Leu Pro Thr Ala
    50                  55                  60

Asp Ala Ile Ala Tyr Val Arg Glu Trp Leu Ser Gln Pro Asn Val Asp
65                  70                  75                  80

Leu Leu Thr Ala Gly Pro Arg His Leu Asp Ile Ala Leu Gly Leu Leu
                85                  90                  95

Asp Lys Leu Gly Thr Ala Ser His Leu Thr Thr Asp Val Gln Leu Ala
            100                 105                 110

Ala Tyr Gly Ile Glu Tyr Asp Ala Glu Ile His Ser Ser Asp Thr Asp
        115                 120                 125

Phe Ala Arg Phe Ala Asp Leu Lys Trp Thr Asp Pro Leu Arg Glu
    130                 135                 140

<210> SEQ ID NO 47
<211> LENGTH: 171
<212> TYPE: PRT
<213> ORGANISM: Mycobacterium tuberculosis

```
<400> SEQUENCE: 47

Leu Thr Asp Pro Arg His Thr Val Arg Ile Ala Val Gly Ala Thr Ala
  1               5                  10                  15

Leu Gly Val Ser Ala Leu Gly Ala Thr Leu Pro Ala Cys Ser Ala His
             20                  25                  30

Ser Gly Pro Gly Ser Pro Pro Ser Ala Pro Ser Ala Pro Ala Ala Ala
         35                  40                  45

Thr Val Met Val Glu Gly His Thr His Thr Ile Ser Gly Val Val Glu
     50                  55                  60

Cys Arg Thr Ser Pro Ala Val Arg Thr Ala Thr Pro Ser Glu Ser Gly
 65                  70                  75                  80

Thr Gln Thr Thr Arg Val Asn Ala His Asp Asp Ser Ala Ser Val Thr
                 85                  90                  95

Leu Ser Leu Ser Asp Ser Thr Pro Pro Asp Val Asn Gly Phe Gly Ile
            100                 105                 110

Ser Leu Lys Ile Gly Ser Val Asp Tyr Gln Met Pro Tyr Gln Pro Val
        115                 120                 125

Gln Ser Pro Thr Gln Val Glu Ala Thr Arg Gln Gly Lys Ser Tyr Thr
    130                 135                 140

Leu Thr Gly Thr Gly His Ala Val Ile Pro Gly Gln Thr Gly Met Arg
145                 150                 155                 160

Glu Leu Pro Phe Gly Val His Val Thr Cys Pro
                165                 170

<210> SEQ ID NO 48
<211> LENGTH: 312
<212> TYPE: DNA
<213> ORGANISM: Mycobacterium tuberculosis

<400> SEQUENCE: 48
atgaatcgca tcgtgcagtt cggagtttcc gccgtggccg cggcggcgat cggcatcgga      60
gccgggtcgg ggatcgcggc ggcgttcgac ggcgaggacg aggtgaccgg ccccgacgcc     120
gaccgcgcgc cgccgccgc ggtgcaggcg gtcccgggcg caccgccgg agaagtcgag      180 accgagaccg gcgaaggcgc cgccgcctac ggcgtgctgg tcacccggcc cgacggcacc     240
cgtgtcgagg tccacctgga ccgggatttc cgggttctgg acaccgaacc ggccgacggg     300
gacggcggtt ag                                                         312

<210> SEQ ID NO 49
<211> LENGTH: 333
<212> TYPE: DNA
<213> ORGANISM: Mycobacterium tuberculosis

<400> SEQUENCE: 49
atgaggctgt cgttgaccgc attgagcgcc ggtgtaggcg ccgtggcaat gtcgttgacc      60
gtcggggccg gggtcgcctc cgcagatccc gtggacgcgg tcattaacac cacctgcaat     120
tacgggcagg tagtagctgc gctcaacgcg acggatccgg gggctgccgc acagttcaac     180
gcctcaccgg tggcgcagtc ctatttgcgc aatttcctcg ccgcaccgcc acctcagcgc     240
gctgccatgg ccgcgcaatt gcaagctgtg ccggggggcgg cacagtacat cggccttgtc     300
gagtcggttg ccggctcctg caacaactat taa                                  333

<210> SEQ ID NO 50
<211> LENGTH: 846
<212> TYPE: DNA
```

-continued

<213> ORGANISM: Mycobacterium tuberculosis

<400> SEQUENCE: 50
atgttcaccg gcatcgctag ccatgccggc gccctgggtg ccgccttagt ggtgctgatc 60
ggcgccgcaa ttctgcacga cggcccagca gcggccgacc caaaccaaga cgatcggttt 120
ctggcgctgc tcgagaaaaa ggaaatcccc gccgtcgcga atgtgcctcg cgtcatcgac 180
gcggcccaca aagtgtgtcg caaactcgat ggcggcatgc cggtgaacga cattgtggac 240
gggttacgca acgatgccta caacatagac ccggtcatgc gcctctaccc tgtccgcctc 300
acgacgacca tgacccgatt tatcagtgcg gcagtggaga tctactgccc gaaccatcac 360
agcaagatgg cgttcgccat ggccaatttc gagccgggat cgaatgaacc gacgcatcgc 420
gttgcggcgt ccacgcgcag cgcggtcaac tcgggaagcg acctgcgggc gtcggtgtcg 480
gacatgacca tcatgtcgcc gggatggcgg gaaccgacgg gtgcgatgct tgcctcggtg 540
ctcggagcgg ttcgcgcggg ggatcccctg ataccgaatc cgccgccgat tccggtaccg 600
ccgccggcgg cgcagaccct gattccaccc ccgccgatcg tggcaccgcc gccaccgcga 660
ccagcgccgc cgcaacagcc gccgccccccg ccgccagagg ttgagccgcc tgctggtgtt 720
ccgcagtccg gggcgctgc cggcagtggc ggcgccggca gcggtggtgg cggcggtggt 780
gacggaccgg tagagccgtc gcctgcacga cccatgccgc cgggctttat caggctcgcg 840
ccgtga 846

<210> SEQ ID NO 51
<211> LENGTH: 531
<212> TYPE: DNA
<213> ORGANISM: Mycobacterium tuberculosis

<400> SEQUENCE: 51
atgacgcggc tgataccggg ttgcacgctc gtcgggctga tgctgacgtt actgcccgcg 60
cccacctcgg cggccgggag caacaccgcc accaccctgt tcccggtcga cgaggtcacc 120
cagctggaga cgcacacctt cctcgattgc caccccaacg gcagctgcga cttcgtcgct 180
ggagcaaatc tgcgcacacc cgacggcccg acgggctttc cgcccgggct gtgggcgcgc 240
caaaccaccg agatccgttc gacgaaccgg ttggcctatc tggacgcgca cgccaccagc 300
cagttcgaac gggtaatgaa ggcgggcgga tccgacgtga tcaccaccgt ctacttcggc 360
gagggtccgc cggacaaata ccagaccacc ggggtcatcg actcgaccaa ttggtcgacc 420
ggtcaaccga tgaccgacgt caacgtcatc gtgtgtacac acatgcaggt ggtctacccg 480
ggggtcaacc tcacctcgcc cagcacctgc gcgcaagcca acttttccta g 531

<210> SEQ ID NO 52
<211> LENGTH: 1704
<212> TYPE: DNA
<213> ORGANISM: Mycobacterium tuberculosis

<400> SEQUENCE: 52
atggttttaa gaagtaggaa aagcacgctc ggcgttgtcg tgtgcttagc gctggtgctc 60
ggtgggccgc tcaacggttg cagcagcagc gcgagccacc gcggtccact gaacgcaatg 120
ggaagtccgg ccataccgtc gacggcgcag gagataccca acccgttgcg cggtcagtac 180
gaagacctca tggaaccgct gtttccgcag gggaaccccg cgcagcaacg ctatccgcct 240
tggcccgcgt cctacgacgc gagtttgcga gtctcctggc ggcagctgca gcctacggat 300
ccgcgcactc tgcccccgga tgctccggac gaccgcaagt acgacttcag cgtgatcgac 360

-continued

```
aacgcgttga ccaggctcgc cgaccgcggc atgcggctga cgctgcgggt gtacgcctac        420
agctcgtgct gcaaggcttc ctatccggac ggcactaaca tcgcgattcc cgactgggag        480
cgcgctatcg ccagcaccaa caccagttat ccagggccgg cgaccgatcc ctcgaccggg        540
gtggtgcagg tggtgccgaa tttcaacgat tcgacctatc ttaacgattt tgcgcagttg        600
ctcgccgcgc ttggtcgccg ctacgacggt gacgagcgcc tcagcgtgtt cgagttctcc        660
gggtacgggg acttcagcga aaatcacgtc gcatacctgc gcgacacgct cggtgcgccg        720
ggtccgggcc cggatgaaag cgtggcgacc ctgggctatt acagccagtt ccgtgatcag        780
aacatcacca ccgcgtccat caaacagcta atcgcggcga acgtcagcgc cttcccgcat        840
acccaactgg tgaccagtcc cgctaatccg gaaatcgtgc gagaactgtt cgccgacgag        900
gtcaccaaca agcttgccgc gccggtgggt gtccgctcgg attgcctggg cgtcgacgcg        960
ccgttgccgg cctgggccga gtccagcact tcgcactatg tgcagaccaa agacccggtg       1020
gtcgccgcgc tgcggcagcg gctggcaacg gcgccggtga tcaccgagtg gtgcgagttg       1080
ccgaccggca gttcgccgcg ggcttactac gagaagggcc tgcgcgacgt catcaggtat       1140
cacgtgtcga tgacgtcgag cgttaacttc cccgaccaga cggcgacctc gccgatggac       1200
cccgcgttgt acctggtgtg ggcgcaagct aacgccgccg caggctatcg gtactcggtc       1260
gaagcgcagc cggggtcgca agcgctagcg ggcaaggtcg cgacgatctc ggtcacctgg       1320
accaactacg gcgctgctgc cgccaccgaa aagtgggtgc ccggctaccg gctggtggat       1380
tccaccggac aggtggttcg gacgctgccg gcagcggtgg acctgaagac gctggtctcc       1440
gaccagcgcg gcgatcgcag cagcgaccag ccgacaccgg cgtcggtcgc cgagacggtt       1500
cgcgttgatc tgtccggctt gcccgcgggc cactacacgc tgcgggccgc gatcgactgg       1560
caacagcaca aaccgaacgg ctcccatgtg gtgaactatc cgcccatgct gttgtcccgc       1620
gacggccgcg acgattccgg gttttatccc gtcgccacgc tcgacatccc acgcgacgcg       1680
cagaccgcgg tcaacgcttc gtag                                              1704
```

<210> SEQ ID NO 53
<211> LENGTH: 657
<212> TYPE: DNA
<213> ORGANISM: Mycobacterium tuberculosis

<400> SEQUENCE: 53

```
atgagccgac tcctagcttt gctgtgcgct gcggtatgca cgggctgcgt tgctgtggtt         60
ctcgcgccag tgagcctggc cgtcgtcaac ccgtggttcg cgaactcggt cggcaatgcc        120
actcaggtgg tttcggtggt gggaaccggc ggttcgacgg ccaagatgga tgtctaccaa        180
cgcaccgccg ccggctggca gccgctcaag accggtatca ccacccatat cggttcggcg        240
ggcatggcgc cggaagccaa gagcggatat ccggccactc cgatgggggt ttacagcctg        300
gactccgctt ttggcaccgc gccgaatccc ggtggcgggt tgccgtatac ccaagtcgga        360
cccaatcact ggtggagtgg cgacgacaat agccccacct ttaactccat gcaggtctgt        420
cagaagtccc agtgcccgtt cagcacggcc gacagcgaga acctgcaaat cccgcagtac        480
aagcattcgg tcgtgatggg cgtcaacaag gccaaggtcc caggcaaagg ctccgcgttc        540
ttctttcaca ccaccgacgg cgggcccacc gcgggttgtg tggcgatcga cgatgccacg        600
ctggtgcaga tcatccgttg gctgcggcct ggtgcggtga tcgcgatcgc caagtaa           657
```

<210> SEQ ID NO 54

<211> LENGTH: 408
<212> TYPE: DNA
<213> ORGANISM: Mycobacterium tuberculosis

<400> SEQUENCE: 54

| | | |
|---|---|---|
| atgattcgcg aactggtcac caccgctgcg atcacgggtg ccgcgatcgg tggggcgcca | 60 | |
| gtcgcgggcg cagacccgca gcgttatgac ggcgatgtgc cggggatgaa ctatgacgct | 120 | |
| tcgctgggcg ccccatgctc cagctgggag cgcttcattt ttggacgagg cccctccggt | 180 | |
| caggccgaag cctgtcattt tccgcctcct aaccagttcc cgccggccga aaccggctac | 240 | |
| tgggtgatct cctacccgct atacggcgtc cagcaggtcg gtgcgccgtg tccgaagccg | 300 | |
| caggcggccg cgcagtctcc ggatgggttg ccgatgctgt gtctgggagc ccgtggatgg | 360 | |
| cagccgggat ggtttaccgg ggccgggttc ttccctccgg agccataa | 408 | |

<210> SEQ ID NO 55
<211> LENGTH: 474
<212> TYPE: DNA
<213> ORGANISM: Mycobacterium tuberculosis

<400> SEQUENCE: 55

| | | |
|---|---|---|
| atgggtgaat tacggttggt gggcggtgtg ctccgggtcc ttgtcgtggt cggtgcggtg | 60 | |
| ttcgatgtgg cggtgctaaa cgccggtgcg gctagtgccg acggcccggt ccagctgaag | 120 | |
| agccgattgg gcgatgtttg cctggacgcc ccgagtggga gctggttcag cccgctggtg | 180 | |
| atcaacccct gcaatgggac cgactttcag cgctggaatc tcaccgatga ccggcaggtc | 240 | |
| gagagcgtgg ccttccccgg ggaatgcgtg aatatcggaa atgctttgtg ggcgcgcctg | 300 | |
| cagccctgtg tgaactggat cagccagcac tggactgtcc agcccgacgg cctggtcaag | 360 | |
| agtgatcttg atgcctgcct cacggttctc ggcggtccgg atcctgggac ctgggtgtcc | 420 | |
| acccgctggt gcgaccccaa tgcacccgac caacagtggg atagcgtgcc gtaa | 474 | |

<210> SEQ ID NO 56
<211> LENGTH: 723
<212> TYPE: DNA
<213> ORGANISM: Mycobacterium tuberculosis

<400> SEQUENCE: 56

| | | |
|---|---|---|
| atgccggcca tgaccgcccg ttcggtggta ctcagcgtgc tgctcggtgc tcatcccgcg | 60 | |
| tgggccaccg caagcgaatt gatccagctg acagcggatt tcggtatcaa ggagacgacg | 120 | |
| ttgcgggtcg cgctgacccg catggtcggt gccggggatc tggtccggtc cgcggacggc | 180 | |
| taccggctct cggatcggtt gctggcccgc cagcgccgac aagatgaggc catgcgccca | 240 | |
| cggacccgcg cttggcacgg aaactggcac atgctgattg tcaccagcat cggcaccgat | 300 | |
| gctcgtaccc gggccgcact gcgaacctgc atgcaccaca agcgtttcgg tgaattgcgg | 360 | |
| gaagggggtgt ggatgcggcc ggacaatctc gacctcgact ggagtccga cgttgcggcc | 420 | |
| cgggttagga tgctgacggc ccgcgacgag gccccgccg acttggccgg gcagctgtgg | 480 | |
| gatctgtcgg ggtggaccga ggccggccac cggttgctcg cgacatggc agcggccacc | 540 | |
| gacatgcccg ggcgatttgt ggtggctgcg gcgatggtgc gccacctgct caccgatccg | 600 | |
| atgttgcccg ctgaactgtt gcccgccgac tggccgggcg ccgggttacg ggcggcgtac | 660 | |
| cacgacttcg ccactgcaat ggcgaaacga cgcgatgcaa ctcaactcct ggaggtgaca | 720 | |
| tga | 723 | |

```
<210> SEQ ID NO 57
<211> LENGTH: 465
<212> TYPE: DNA
<213> ORGANISM: Mycobacterium tuberculosis

<400> SEQUENCE: 57
gtgccggccg gcgtcggtaa cgcatccggt agcgttttag atatgacgtc cgtgcgcaca      60
gtgccaagcg ccgtcgcgct ggtgacgttt gccggagccg cgctcagcgg ggtcatcccg     120
gcgattgccc gcgcggatcc ggtcgggcat caggtgacct acaccgtcac gaccaccagc     180
gacctgatgg ccaacattcg gtacatgagc gccgatccgc ccagcatggc ggctttcaat     240
gccgattcat cgaagtacat gattaccttg cacactccga tcgctggcgg tcagccgctg     300
gtctataccg ccacgctggc aaacccgagc cagtgggcga tcgtcaccgc cagcggcggc     360
ctgcgggtca atccggagtt ccactgcgag attgttgtag acggccaggt ggtggtgtcg     420
caggacggcg gcagcggcgt gcagtgctcg actcgtccct ggtaa                     465

<210> SEQ ID NO 58
<211> LENGTH: 699
<212> TYPE: DNA
<213> ORGANISM: Mycobacterium tuberculosis

<400> SEQUENCE: 58
atgacgacca gcaaaatcgc caccgccttc aagaccgcca ccttcgcgct ggccgccggt      60
gccgttgcac tgggattggc cagccccgcc gacgcagcgg cgggcaccat gtatggcgac     120
ccggcagccg ccgccaagta ctggcgccag cagacatacg acgactgcgt cctgatgtcg     180
gccgcggacg tgatcggtca agtgaccggc agggagcctt ccgagcgcgc catcatcaaa     240
gtggcccagt cgacacccag cgtcgtgcac cccgggtcca tctacacaaa gccggccgac     300
gccgagcacc cgaactcggg aatgggtacc agcgtggccg acataccgac gctgctggcg     360
cattacggcg tcgacgccgt tatcaccgac gaggaccacg ccacagccac cggagtcgcc     420
accggcatgg ccgccctcga gcagtatctg ggcagcgggc acgccgtgat cgtcagcatc     480
aacgccgaga tgatctgggg ccagcccgtc gaggaaaccg acagtgccgg caacccgcgg     540
tctgaccacg ccgtggtggt gaccggtgtc gataccgaaa acggcattgt tcacctcaac     600
gacagcggta cccccacggg ccgcgacgag cagatcccga tggaaacctt cgtcgaggcg     660
tgggccacca gccacgactt catggccgtc accacctga                            699

<210> SEQ ID NO 59
<211> LENGTH: 642
<212> TYPE: DNA
<213> ORGANISM: Mycobacterium tuberculosis

<400> SEQUENCE: 59
atgggagtca ttcccgcgt tgtcggtgtc gccgcgtgcg gtttgtccct ggccgtgctg       60
gccgccgcgc ccaccgcggg cgcggaaccc accggcgcgc tgccccgat gacatccagc      120 ggcagcggac cggtcatcgg cgacggtgac gccgcgctgc gacagcggat ctcacagcag     180
ctgtttagct tcggagatcc caccgtccag gaggttgacg gctcggacgc ggctcaattc     240
atcacgcccg cagccgctgt cgcggaccgc gatgtggcgt cggtgttctt gccgctgcag     300
cgggtgttgg gctgccaaca gaacacagcc ggctcggggg ccggcttcgg ggcgcgcgcc     360
taccggcgaa ccgacgggca atggggaggc gcgatgctgg tcgtcgccaa gagcaccgtt     420
tccgacgtcg acgccctcaa ggcctgcgtc aagtccggtt ggcgcaaggc cacggcgggc     480
```

```
acgccgactt cgatgtgcaa caacggttgg acctacccgc cgttcgccga cacccgccgc    540
ggcgaagagg gctatttcgt cttgctggcc ggcacggcct cggacttctg cagtgcgccc    600
aacgcgaact accgaaccac cgcgagctca tggccgggct ag                       642
```

<210> SEQ ID NO 60
<211> LENGTH: 471
<212> TYPE: DNA
<213> ORGANISM: Mycobacterium tuberculosis

<400> SEQUENCE: 60

```
atgcgcttga agccagcccc atctcctgct gcagcctttg ccgtcgccgg cctgatcctc     60
gcaggctggg ccggatccgt gggcctcgcc ggcgccgatc cggagccggc accgacaccg    120
aagacggcaa ttgatagcga cggcacctat gcggtgggga ttgacatcgc tcccggcacg    180
tacagctccg cgggacccgt cggcgacggc acctgctatt ggaagcggat gggtaacccc    240 gatgcgcgc tcatcgataa cgcactcagc aagaaaccac aggtagtgac gattgagccg    300
accgacaagg cgttcaagac gcacggctgc caaccctggc agaacacggg cagcgaaggc    360 gctgccctg ccggagttcc tggacctgaa gcggggccc aactacaaaa tcagctcggc     420
atcctcaacg gcttactcgg accgactgga gggcgagtgc ctcagcccta a             471
```

<210> SEQ ID NO 61
<211> LENGTH: 432
<212> TYPE: DNA
<213> ORGANISM: Mycobacterium tuberculosis

<400> SEQUENCE: 61

```
atgatcacaa acctccgacg ccgaaccgcg atggcagccg ccggcctagg ggctgctctc     60
gggctgggca tcctgctggt tccgacggtg gacgcccatc tcgccaacgg ttcgatgtcg    120
gaagtcatga tgtcggaaat tgccgggttg cctatcctc cgattatcca ttacggggcg    180
attgcctatg cccccagcgg cgcgtcgggc aaagcgtggc accagcgcac accggcgcga    240
gcagagcaag tcgcactaga aaagtgcggt gacaagactt gcaaagtggt tagtcgcttc    300
accaggtgcg gcgcggtcgc ctacaacggc tcgaaatacc aaggcggaac cggactcacg    360
cgccgcgcgg cagaagacga cgccgtgaac cgactcgaag gcgggcggat cgtcaactgg    420
gcgtgcaact aa                                                        432
```

<210> SEQ ID NO 62
<211> LENGTH: 402
<212> TYPE: DNA
<213> ORGANISM: Mycobacterium tuberculosis

<400> SEQUENCE: 62

```
gtgacggtgc tgctcgacgc caacgtgctg atcgcattgg tggtcgccga gcatgtgcat     60
catgatgccg cagcggactg gctcatggcg tccgacaccg gatttgcgac ctgcccgatg    120
acacaaggaa gcctggttcg attcctggtg cgctcgggac agtccgcggc ggcggctcgg    180
gatgtcgtca gtgcggtcca gtgcacgagc cgccacgaat tctggcccga tgcactctct    240
ttcgccggtg tcgaggtcgc tggtgtggtt gggcaccggc aggtgaccga tgcctacctt    300
gcccagctcg cgcgaagcca cgacgggcag ttggcgacgc tcgacagcgg cttagcacac    360
ctgcacggcg acgtcgcggt actcattcca acgaccacct ga                       402
```

<210> SEQ ID NO 63
<211> LENGTH: 378

-continued

<212> TYPE: DNA
<213> ORGANISM: Mycobacterium tuberculosis

<400> SEQUENCE: 63
gtgcagcgcc aatcattgat gccccagcag acccttgccg ccggcgtttt cgtgggtgcg 60
ctgctatgcg gtgtcgtgac ggcggcggtg ccaccacacg cacgcgccga cgtggtcgcc 120
tatctggtca acgtgacggt acgcccgggc tacaacttcg ccaacgccga cgccgcgttg 180
agttacggac atggcctctg cgagaaggtg tctcggggcc gcccttacgc acagatcatc 240
gccgacgtca aggctgattt cgacacccgc gaccaatacc aggcctcgta tctgctcagc 300
caggctgtca acgaactctg ccccgcgctg atctggcagt tgcgaaactc cgcagtcgac 360
aatcggcgct cgggctga 378

<210> SEQ ID NO 64
<211> LENGTH: 657
<212> TYPE: DNA
<213> ORGANISM: Mycobacterium tuberculosis

<400> SEQUENCE: 64
gtgcgttcgt atctattgcg tatcgagctg gccgaccggc cgggcagcct tgggtcgctg 60
gcggtcgcgc tcggctcggt gggcgccgac atcctctcgc tcgacgtggt cgagcgcggc 120
aacggctatg cgatcgacga cctggtggtc gaactgcccc cgggagcgat gcccgacacg 180
ctgatcactg ctgccgaggc gctgaacggc gtccgggtag acagcgtccg cccgcacacc 240
ggcctgttgg aagcccaccg cgagctggaa ctgctcgatc atgtggccgc ggctgagggc 300
gcgaccgcac ggctccaggt tctggtcaac gaggcccccc gggtgctccg ggtgagctgg 360
tgcacggtgt tgcgcagttc cggcggggag ctgcaccgtc tggccggcag cccaggtgcg 420
ccggagaccc gggccaattc ggcgccctgg ctgccgatcg agcgggccgc ggcgctggac 480
ggcggcgccg actgggtgcc gcaagcctgg cgcgacatgg ataccaccat ggtcgcggct 540
ccattgggtg acacgcacac cgcggtggtg ctgggcaggc caggcccgga atttcgcccg 600
tcggaggtgg cgcggttggg ttatctagcc ggcatcgtgg cgacgatgct gcgctga 657

<210> SEQ ID NO 65
<211> LENGTH: 660
<212> TYPE: DNA
<213> ORGANISM: Mycobacterium tuberculosis

<400> SEQUENCE: 65
atgcctgacg gggagcagag ccagccaccg gcccaagaag atgcggaaga cgactcgcgg 60
cccgacgccg cggaggccgc cgcggccgaa cccaaatcat cagccggtcc gatgttctcg 120
acctacggta tcgcctcgac actactcggc gtgctatcgg tcgccgcggt cgtgctgggt 180
gcgatgatct ggtccgcaca ccgcgatgac tccggcgagc gtacctacct gacccgggtc 240
atgctgaccg ccgctgaatg gacggccgtg ctgatcaaca tgaacgccga caacatcgat 300
gccagcctgc agcgactgca cgacggaacg gtcggtcaac tcaacaccga cttcgacgct 360
gtcgtgcagc cctaccggca ggtggtggag aagttgcgga cgcacagcag cggcaggatc 420
gaggcggtag cgatcgatac ggtgcaccgc gagctggata cccagtccgg tgccgcccga 480
ccggtagtaa ccacgaaatt gccaccgttt gccactcgca ccgactcggt gctgctggtc 540
gcgacgtcgg tcagtgagaa cgccggcgcc aaaccccaga ccgtgcactg gaacttgcgg 600
ctcgatgtct ccgatgtgga cggcaagctg atgatctccc ggttggagtc gattcgatga 660

<210> SEQ ID NO 66
<211> LENGTH: 507
<212> TYPE: DNA
<213> ORGANISM: Mycobacterium tuberculosis

<400> SEQUENCE: 66

| | | | | | |
|---|---|---|---|---|---|
| atgaagatgg | tgaaatcgat | cgccgcaggt | ctgaccgccg | cggctgcaat | cggcgccgct | 60 |
| gcggccggtg | tgacttcgat | catggctggc | ggcccggtcg | tataccagat | gcagccggtc | 120 |
| gtcttcggcg | cgccactgcc | gttggacccg | gcatccgccc | ctgacgtccc | gaccgccgcc | 180 |
| cagttgacca | gcctgctcaa | cagcctcgcc | gatcccaacg | tgtcgtttgc | gaacaagggc | 240 |
| agtctggtcg | agggcggcat | cggggggcacc | gaggcgcgca | tcgccgacca | caagctgaag | 300 |
| aaggccgccg | agcacgggga | tctgccgctg | tcgttcagcg | tgacgaacat | ccagccggcg | 360 |
| gccgccggtt | cggccaccgc | cgacgtttcc | gtctcgggtc | cgaagctctc | gtcgccggtc | 420 |
| acgcagaacg | tcacgttcgt | gaatcaaggc | ggctggatgc | tgtcacgcgc | atcggcgatg | 480 |
| gagttgctgc | aggccgcagg | gaactga | | | | 507 |

<210> SEQ ID NO 67
<211> LENGTH: 390
<212> TYPE: DNA
<213> ORGANISM: Mycobacterium tuberculosis

<400> SEQUENCE: 67

| | | | | | |
|---|---|---|---|---|---|
| atgaacctac | ggcgccatca | gaccctgacg | ctgcgactgc | tggcggcatc | cgcgggcatt | 60 |
| ctcagcgccg | cggccttcgc | cgcgccagca | caggcaaaacc | ccgtcgacga | cgcgttcatc | 120 |
| gccgcgctga | acaatgccgg | cgtcaactac | ggcgatccgg | tcgacgccaa | agcgctgggt | 180 |
| cagtccgtct | gcccgatcct | ggccgagccc | ggcgggtcgt | ttaacaccgc | ggtagccagc | 240 |
| gttgtggcgc | gcgcccaagg | catgtcccag | gacatggcgc | aaaccttcac | cagtatcgcg | 300 |
| atttcgatgt | actgcccctc | ggtgatggca | gacgtcgcca | gcggcaacct | gccggccctg | 360 |
| ccagacatgc | cggggctgcc | cgggtcctag | | | | 390 |

<210> SEQ ID NO 68
<211> LENGTH: 327
<212> TYPE: DNA
<213> ORGANISM: Mycobacterium tuberculosis

<400> SEQUENCE: 68

| | | | | | |
|---|---|---|---|---|---|
| atgagagttg | tgtcaacgct | actcagcatt | ccgttgatga | tcggcttggc | ggttccggcc | 60 |
| cacgcggggc | ccagcggtga | cgacgcggtc | tttcttgcct | cgctagagcg | ggcaggcatt | 120 |
| acctacagcc | acccggatca | agccatagca | tcgggcaagg | ccgtatgcgc | gttagtcgaa | 180 |
| agcggcgaat | cgggtcttca | ggtcgtcaac | gagctgcgga | cccgcaatcc | cgggttttcg | 240 |
| atggacggtt | gttgcaagtt | cgctgcgatc | tccgcgcatg | tctattgccc | ccaccagatc | 300 |
| actaaaacca | gcgtcagcgc | gaaatag | | | | 327 |

<210> SEQ ID NO 69
<211> LENGTH: 372
<212> TYPE: DNA
<213> ORGANISM: Mycobacterium tuberculosis

<400> SEQUENCE: 69

| | | | | | |
|---|---|---|---|---|---|
| atggcccgca | cgcttgcgtt | gcgcgcatcg | gcgggactcg | tcgcgggtat | ggcaatggcc | 60 |
| gcgatcacgc | tcgcacctgg | ggcccgcgcc | gaaaccggtg | agcaattccc | cggggatggg | 120 |

```
gtgtttctcg tgggaactga cattgcgcca ggcacctacc gcacggaggg gccgtcgaat      180
cccttatttt tggtgttcgg cagggtgtcc gagctctcaa cctgctcatg gtcgacacac      240
agcgcacccg aggtgagcaa tgagaacatt gtcgacacca acacctctat gggcccgatg      300
tcagtggtga tcccgccgac cgtggcagcc ttccagacgc ataactgcaa gctttggatg      360
cggatctcat ag                                                          372

<210> SEQ ID NO 70
<211> LENGTH: 342
<212> TYPE: DNA
<213> ORGANISM: Mycobacterium tuberculosis

<400> SEQUENCE: 70
atgttatcgc cgttatcgcc tcgcattatc gcagcgttca ccactgcagt cggcgccgcc      60
gccatcggac ttgccgtcgc caccgccggc accgccggcg ccaacaccaa agacgaagcc     120
ttcattgctc agatggagtc cattggcgtc accttctcct caccgcaggt ggccacccag     180
caagcccagc tggtctgcaa gaagctggcc agcggcgaaa ccggcaccga gatcgccgag     240
gaggtcctca gccaaaccaa cctgaccact aagcaggcag cctacttcgt cgtcgacgca     300
accaaggcct actgcccgca atacgccagc cagctcacct ag                         342

<210> SEQ ID NO 71
<211> LENGTH: 375
<212> TYPE: DNA
<213> ORGANISM: Mycobacterium tuberculosis

<400> SEQUENCE: 71
atgacgacga tgattactct tcggcgacgg ttcgcggtgg ccgtcgccgg cgtcgccact      60
gccgccgcga cgaccgtcac cctggctccc gcaccagcaa atgccgccga tgtctatggc     120
gcaattgcct actccggcaa cggctcgtgg ggccgatcgt gggactaccc aacccggggcg     180 gctgccgaag ccaccgccgt caagtcgtgt ggctactccg actgcaaggt gctcaccagt     240
ttcaccgcct gcggcgccgt cgccgccaac gatagggcat accagggagg agttggaccc     300
accttggccg ccgccatgaa ggacgccctg accaagctcg gcggcggcta catcgacacc     360
tgggcctgca actaa                                                       375

<210> SEQ ID NO 72
<211> LENGTH: 465
<212> TYPE: DNA
<213> ORGANISM: Mycobacterium tuberculosis

<400> SEQUENCE: 72
atgacaccgg gtttgcttac tactgcgggt gctggccgac cacgtgacag gtgcgccagg      60
atcgtatgca cggtgttcat cgaaaccgcc gttgtcgcga ccatgtttgt cgcgttgttg     120
ggtctgtcca ccatcagctc gaaagccgac gacatcgatt gggacgccat cgcgcaatgc     180
gaatccggcg gcaattgggc ggccaacacc ggtaacgggt tatacggtgg tctgcagatc     240
agccaggcga cgtgggattc caacggtggt gtcgggtcgc cggcggccgc gagtccccag     300
caacagatcg aggtcgcaga caacattatg aaaacccaag gcccgggtgc gtggccgaaa     360
tgtagttctt gtagtcaggg agacgcaccg ctgggctcgc tcacccacat cctgacgttc     420
ctcgcggccg agactggagg ttgttcgggg agcagggacg attga                      465

<210> SEQ ID NO 73
```

-continued

<211> LENGTH: 1146
<212> TYPE: DNA
<213> ORGANISM: Mycobacterium tuberculosis

<400> SEQUENCE: 73

```
gtgcaaggag ccgttgctgg tctggtgttt ctggccgtcc tggtgatttt cgccatcatc      60
gtggtggcca agtcggtggc gctgatcccg caggcggagg ccgcggtgat cgagcggctg     120
ggtcgctata gtcgtacggt cagtgggcag ttgacgctgt tggtgccgtt catcgaccgc     180
gtccgggctc gggtggacct gcgcgagcgg gtggtgtcgt ttccgccgca accggtgatc     240
accgaggaca acttgacgct gaacatcgac accgtcgtct acttccaggt gaccgttccg     300
caggcggcgg tgtacgagat cagcaattac atcgtcgggg tcgaacagct caccaccacc     360
accctgcgca acgttgtcgg cgggatgacg ctggagcaga cgttgacctc gcgtgaccag     420
atcaacgccc agctgcgcgg cgttctcgat gaggcgaccg gccgctgggg tctgcgggtg     480
gcgcgggtgg agctgcgcag catcgatccg ccgccgtcga ttcaggcgtc gatggaaaag     540
cagatgaagg ccgaccggga gaagcgagcg atgattctga ccgccgaagg tacccgggag     600
gcggcgataa aacaggccga ggggcaaaag caggcgcaga tcctggccgc cgagggcgcc     660
aagcaggccg cgatcttggc tgctgaggcc gatcggcagt ctcggatgct gcgcgctcag     720
ggtgagcgcg ccgcggccta cctgcaggcg caagggcagg ccaaggccat cgagaagacg     780
ttcgccgcga tcaaggctgg ccggcccacc ccggagatgc tggcctacca atacctgcag     840
acgctgccgg agatggcgcg tggggacgcc aacaaggtat gggtggtgcc cagcgacttc     900
aacgccgcac tgcaggggtt caccaggctg ctgggcaagc cgggtgagga cggggtgttc     960
cggttcgagc cgtccccggt cgaagaccag cccaagcacg cggccgacgg tgacgacgcc    1020
gaggtcgccg gctggttctc caccgatacc gacccgtcga tcgctcgggc ggtggctaca    1080
gccgaggcga tagcccgcaa gccggtcgag ggttcgctgg ggacgccccc caggttgact    1140
caatag                                                                1146
```

<210> SEQ ID NO 74
<211> LENGTH: 699
<212> TYPE: DNA
<213> ORGANISM: Mycobacterium tuberculosis

<400> SEQUENCE: 74

```
ttgcagacgg cgcacaggcg ctttgccgcg gcattcgcgg ccgtgctttt ggccgttgtg      60
tgcctacctg cgaacaccgc ggcagccgac gacaagctac cgctgggcgg tggtgcgggc     120
atcgtcgtca acggggacac catgtgcacc ctaaccacca tcggccatga caagaacggt     180
gacctcatcg gcttcacttc cgcccactgt gggggcccgg gcgcgcagat cgccgctgag     240
ggtgccgaga acgcgggccc ggtaggcatc atggtcgccg gcaacgacgg cctggactac     300
gcggtgatca agttcgaccc ggccaaggtg accccggtgg ccgtcttcaa cgggtttgcg     360
atcaacggca ttggcccgga cccgtcgttc ggccagatcg cctgcaagca gggccgcacc     420
accggtaact cgtgcggggt tacctggggg ccaggggaga gtccgggcac ccttgtgatg     480
caggtctgcg gcggaccggg cgactccggt gcgccggtga ccgtcgacaa tctgctggtc     540
gggatgatcc acggcgcatt cagcgacaat ctgccgagtt gcatcaccaa atacatcccg     600
ctgcacaccc cggcggtggt gatgtcgatc aacgccgacc tggccgacat caacgccaag     660
aaccggccgg gcgcgggatt cgtcccggta ccggcctga                            699
```

-continued

<210> SEQ ID NO 75
<211> LENGTH: 885
<212> TYPE: DNA
<213> ORGANISM: Mycobacterium tuberculosis

<400> SEQUENCE: 75

```
atgcttatgc ctgagatgga tcgtcgccga atgatgatga tggcggggtt cggcgccctg     60
gctgccgcgc ttcccgcccc gacagcctgg gccgacccgt cccggccggc cgcgccggct    120
ggtccgacac cggcgcccgc cgcgccggct gcggcaaccg gtgggctttt gttccacgac    180
gagttcgacg ggccggccgg ttcggtcccg gacccgtcca agtggcaggt gtcgaaccac    240
cggacgccca tcaagaaccc ggtgggcttt gaccggcccc agtttttgg gcagtaccgc    300
gacagtcgac agaacgtgtt cctcgacggc aactccaatc tcgtgctgcg cgctacccga    360
gagggcaaca ggtatttcgg tggcctggtc cacggcctgt ggcggggtgg catcgggacc    420
acctgggagg cccggatcaa gttcaactgc ctggctccgg gcatgtggcc cgcctggtgg    480
ttgtccaatg acgatcctgg tcgcagcggc gaaatcgacc tgatcgagtg gtatggcaac    540
gggacttggc cgtcgggaac caccgtgcac gccaacccgg acggcaccgc attcgagacc    600
tgcccgatcg gtgtggacgg tggttggcac aactggcgcg tcacgtggaa tccgagcggc    660
atgtacttct ggctggatta cgccgacggc attgagccct acttctcggt tccggcgacc    720
ggaatcgaag acctcaacga gcccatccgc gagtggccgt tcaacgaccc cggctacaag    780
gtgtttccgg tgttgaacct tgcggttggc ggttctggtg gcggcgatcc cgcgacgggt    840
tcctatccac aggagatgct cgtcgactgg gtgcgcgtct tttaa                    885
```

<210> SEQ ID NO 76
<211> LENGTH: 1140
<212> TYPE: DNA
<213> ORGANISM: Mycobacterium tuberculosis

<400> SEQUENCE: 76

```
gtgcaccgtc gaacggccct gaagctcccg ctgctgctgg cggcaggcac ggtgctgggc     60
caagcgccgc gggccgccgc cgaagaacca ggccggtggt cggccgaccg cgcacatcgc    120
tggtatcaag cgcacggctg gctcgtcggt gcaaactaca tcacctcgaa cgccatcaac    180
cagctcgaga tgttccagcc aggcacatac gatccccggc gcatcgacaa cgagctgggc    240
cttgcgcggt ttcacgggtt caacaccgtg cgagtcttcc tccacgacct gctgtgggcc    300
caagacgcgc ccggtttcca aacccggctc gcgcagttcg tcgccatcgc ggcgcgatac    360
cacatcaaac cgctctttgt cctgttcgac tcctgctggg acccgctccc cagaccgggt    420
cggcagcggg cgccaagggc tggggtgcac aactccgggt gggtgcaaag tccgggtgct    480
gaacgcctcg atgaccgccg ctatgccagc acgctgtaca actacgtcac gggtgtgttg    540
ggccaattcc gcaacgacga tcgcgtgttg ggttgggacc tgtggaatga acccgacaat    600
cccgcgcgcg tgtatcgcaa ggtggaaagg aaagacaagc tcgagcgcgt cgcggagctc    660
ctcccccaag tgttccgatg ggcccgcacg gtcgatccgg ttcaaccgct gaccagtggt    720
gtctggcaag ggaattgggg agatcccgga cgccgcagca ccatcagcgc cattcaactc    780
gacaacgccg acgtgatcac cttccacagt tacgccgcgc cggccgaatt cgagggccgc    840
atcgctgagc tcgctccgtt gcagcggcca atcctgtgca ccgagtacct ggcgcggtcc    900
caaggcagca ctgtcgaggg aatcctgccg attgctaagc ggcacaacgt tggtgcgttc    960
aattggggtt tggtggcggg aaagactcag acctatttgc cgtgggattc gtgggatcac   1020
```

```
ccctaccgcg cgcccccgaa ggtgtggttt cacgacctgc tacaccccaa cggccggccg   1080
tatcgggacg gcgaagttca aacgattcgg aagctgaacg ggatgccgag ccaggactag   1140

<210> SEQ ID NO 77
<211> LENGTH: 858
<212> TYPE: DNA
<213> ORGANISM: Mycobacterium tuberculosis

<400> SEQUENCE: 77
gtgtccacgt acggctggcg cgcctacgcc ctgccggttc tgatggtgct gaccacggtg     60
gtggtgtacc agacggtgac cgggacgagc acgccaaggc ccgcggcggc ccagaccgtc    120
cgggactcgc cggccattgg tgtggtgggg accgcgatcc tcgacgcacc gcctcgcggt    180
cttgcagtgt tcgatgccaa tctgccggcc gggacgctgc cggatggcgg cccgttcacc    240
gaggctggtg acaagacctg gcgtgtcgtt ccgggcacta ctccccaggt cggtcaaggc    300
accgtcaaag tgttcaggta taccgtcgag atcgagaacg gtcttgatcc acaatgtac    360 ggcggtgaca acgcattcgc ccagatggtc gaccagacgt tgaccaatcc caagggctgg    420
acccacaatc cgcaattcgc gttcgtgcgg atcgacagcg gaaaacccga cttccggatt    480
tcgctggtgt cgccgacgac agtgcgcggg gggtgtggct acgaattccg gctcgagacg    540
tcctgctaca acccgtcgtt cggcggcatg gatcgccaat cgcgggtgtt catcaacgag    600
gcgcgctggg tacgcggagc cgttccattc gaaggtgacg taggttccta tcggcaatat    660
gtgatcaacc acgaggtcgg tcatgccatc ggttacctgc ccacgagcc gtgcgaccaa    720 caaggcggtc tggctccggt aatgatgcag cagacgtttt ccacctccaa tgacgacgcg    780
gccaagtttg accccgactt cgttaaggcg gatggaaaga cctgccgatt caatccctgg    840
ccctacccga ttccctaa                                                 858

<210> SEQ ID NO 78
<211> LENGTH: 1371
<212> TYPE: DNA
<213> ORGANISM: Mycobacterium tuberculosis

<400> SEQUENCE: 78
atgcgtccct attacatcgc catcgtgggc tccgggccgt cggcgttctt cgccgcggca     60
tccttgctga aggccgccga cacgaccgag gacctcgaca tggccgtcga catgctggag    120
atgttgccga ctccctgggg gctggtgcgc tccggggtcg cgccggatca ccccaagatc    180
aagtcgatca gcaagcaatt cgaaaagacg gccgaggacc cccgcttccg cttcttcggc    240
aatgtggtcg tcggcgaaca cgtccagccc ggcgagctct ccgagcgcta cgacgccgtg    300
atctacgccg tcggcgcgca gtccgatcgc atgttgaaca tccccggtga ggacctgccg    360
ggcagtatcg ccgccgtcga tttcgtcggc tggtacaacg cacatccaca cttcgagcag    420
gtatcacccg atctgtcggg cgcccgggcc gtagttatcg gcaatggaaa cgtcgcgcta    480
gacgtggcac ggattctgct caccgatccc gacgtgttgg cacgcaccga tatcgccgat    540
cacgctttgg aatcgctacg cccacgcggt atccaggagg tggtgatcgt cgggcgccga    600
ggtccgctgc aggccgcgtt caccacgttg gagttgcgcg agctggccga cctcgacggg    660
gttgacgtgt tgatcgatcc ggcggagctg acggcatta ccgacgagga cgcggccgcg    720
gtgggcaagg tctgcaagca gaacatcaag gtgctgcgtg gctatgcgga ccgcgaaccc    780
cgccccggga accgccgcat ggtgttccgg ttcttgacct ctccgatcga gatcaagggc    840
aagcgcaaag tggagcggat cgtgctgggc cgcaacgagc tggtctccga cggcagcggg    900
```

```
cgagtggcgg ccaaggacac cggcgagcgc gaggagctgc cagctcagct ggtcgtgcgg    960
tcggtcggct accgcggggt gcccacgccc gggctgccgt tcgacgacca gagcgggacc   1020
atccccaacg tcggcggccg aatcaacggc agccccaacg aatacgtcgt cgggtggatc   1080
aagcgcgggc cgaccggggt gatcgggacc aacaagaagg acgcccaaga caccgtcgac   1140
accttgatca agaatcttgg caacgccaag gagggcgccg agtgcaagag ctttccggaa   1200
gatcatgccg accaggtggc cgactggcta gcagcacgcc agccgaagct ggtcacgtcg   1260
gcccactggc aggtgatcga cgctttcgag cggggccgcc gcgagccgca cgggcgtccc   1320
cgggtcaagt tggccagcct ggccgagctg ttgcggattg ggctcggctg a            1371
```

<210> SEQ ID NO 79
<211> LENGTH: 1347
<212> TYPE: DNA
<213> ORGANISM: Mycobacterium tuberculosis

<400> SEQUENCE: 79

```
gtgacaaacc caccgtggac tgtcgatgtt gtcgtggtgg gcgcgggctt cgccgggctg     60
gccgcggccc gcgagctgac gcgacagggt cacgaggtgc tggtgttcga aggccgcgat    120
cgggtgggcg gccgctcgtt aaccggtcgc gtggcagggg tgcccgcgga tatgggcggc    180
tcgttcatcg gcccgaccca agacgccgtg ctggcgttgg ccaccgagct ggggatcccg    240
acaaccccga cccaccgcga cggccgaaac gtcatccagt ggcggggatc ggcacgcagc    300
tatcgtggca ccatccccaa gctgtcgctg accgggctca tcgacatcgg ccggttgcgt    360
tggcaattcg agcgaattgc ccgcggcgtt ccggtggccg cccctggga tgcgcggcgc     420
gcgcgtgaac tcgacgacgt gtcgctcggg gagtggttgc gcttggtgcg cgccacatcg    480
tcctcgcgga acctgatggc catcatgacc cgggtgacct ggggttgtga gcccgacgat    540
gtctcgatgc tgcacgccgc ccgctacgta cgcgcggccg cgggcctgga ccggctgctc    600
gacgtcaaaa atggtgccca gcaggaccgt gtgccggggg ggacacagca gatcgcccag    660
gcggccgccg cccaactcgg cgcacgcgtc ctgctcaacg ccgcggtgcg tcgcatcgac    720
cggcacggag cgggtgtgac ggtcacgtcc gatcagggtc aggccgaggc cgggttcgtc    780
atcgtcgcca ttccaccggc ccatcgcgtg gccatcgagt tcgatccccc gctgccgccg    840
gaatatcagc agctcgccca ccattggccg cagggccggc tgagcaaggc ctacgcggcc    900
tattcgacgc cgttctggcg ggccagcggg tattccggcc aggcgctgtc cgatgaggcg    960
ccggtgttca tcaccttcga cgtcagtccg cacgccgacg ggccaggcat tctgatgggg   1020
ttcgtcgatg ctcgcgggtt cgactcgcta cccatcgaag agcgccgccg cgatgcattg   1080
cgctgctttg cgtcgctgtt cggcgacgaa gcgctcgacc cccttgatta tgttgactat   1140
cgttggggta cagaggaatt cgcgccgggt ggtccgaccg cggcggtacc gccggggtcg   1200
tggacgaaat acggtcactg gttacgtgag ccggtcggtc cgattcactg ggcgagcact   1260
gagaccgcgg acgaatggac cgggtatttc gacggcgccg tcagatccgg tcagcgtgcc   1320
gccgccgagg tcgccgccct gctatga                                      1347
```

<210> SEQ ID NO 80
<211> LENGTH: 339
<212> TYPE: DNA
<213> ORGANISM: Mycobacterium tuberculosis

<400> SEQUENCE: 80

-continued

| | |
|---|---|
| atgaagggaa caaagctggc tgttgtcgtc ggcatgacgg tggctgccgt tagtttggca | 60 |
| gcgccggcgc aggccgacga ctacgacgcc cccttcaaca cacgatcca tcgcttcggg | 120 |
| atctacggcc cgcaggacta caacgcttgg cttgccaaga tcagctgcga acggctgagc | 180 |
| agaggcgttg acgcgatgc gtacaagtcg gccactttcc tgcaacgcaa cctgccgcgc | 240 |
| ggaaccaccc agggccaagc gtttcagttc ctgggcgccg cgatcgatca ctactgccct | 300 |
| gagcatgtgg gcgtcctgca acgggctggc acccgctaa | 339 |

```
<210> SEQ ID NO 81
<211> LENGTH: 447
<212> TYPE: DNA
<213> ORGANISM: Mycobacterium tuberculosis

<400> SEQUENCE: 81
```

| | |
|---|---|
| atgaaagccc tggtggccgt gtcggcggtg gccgtcgtcg cactgctcgg tgtatcttcc | 60 |
| gcccaagctg atcccgaggc ggatcccggc gcaggtgagg ccaactatgg tggcccccca | 120 |
| agttccccac gtcttgtcga tcacaccgaa tgggcgcagt ggggaagtct gcccagcctc | 180 |
| cgggtctacc cgtcccaagt tgggcgtaca gcctcccgcc gcctcgggat ggccgctgcc | 240 |
| gacgcggcct gggccgaggt tctcgcgctg tcaccggagg ccgacactgc cggcatgcgc | 300 |
| gcgcagttca tctgccactg gcagtacgcc gaaatcagac aacccggcaa acccagctgg | 360 |
| aacctcgagc cgtggcggcc ggtcgtcgac gactcggaga tgttggcttc cggctgcaat | 420 |
| ccgggcagcc ctgaagagtc gttttag | 447 |

```
<210> SEQ ID NO 82
<211> LENGTH: 1224
<212> TYPE: DNA
<213> ORGANISM: Mycobacterium tuberculosis

<400> SEQUENCE: 82
```

| | |
|---|---|
| atgagtggac gccaccgtaa gcccaccaca tccaacgtca gcgtcgccaa gatcgccttt | 60 |
| accggcgcag tactcggtgg cggcggcatc gccatggccg ctcaggcgac cgcgccacc | 120 |
| gacggggaat gggatcaggt ggcccgctgc gagtcgggcg gcaactggtc gatcaacacc | 180 |
| ggcaacggtt acctcggtgg cttgcagttc actcaaagca cctgggccgc acatggtggc | 240 |
| ggcgagttcg ccccgtcggc tcagctggcc agccgggagc agcagattgc cgtcggtgag | 300 |
| cgggtgctgg ccacccaggg tcgcggcgcc tggccggtgt gcggccgcgg gttatcgaac | 360 |
| gcaacacccc gcgaagtgct tcccgcttcg gcagcgatgg acgctccgtt ggacgcggcc | 420 |
| gcggtcaacg gcgaaccagc accgctggcc ccgccgcccg ccgacccggc gccacccgtg | 480 |
| gaacttgccg ctaacgacct gcccgcaccg ctgggtgaac cctccccggc agctcccgcc | 540 |
| gacccggcac cacccgccga cctggcacca cccgcgcccg ccgacgtcgc gccacccgtg | 600 |
| gaacttgccg taaacgacct gcccgcaccg ctgggtgaac cctccccggc agctcccgcc | 660 |
| gacccggcac cacccgccga cctggcacca cccgcgcccg ccgacctggc gccacccgcg | 720 |
| cccgccgacc tggcgccacc cgcgcccgcc gacctggcac cacccgtgga acttgccgta | 780 |
| aacgacctgc ccgcgccgct gggtgaaccc ctccggcag ctcccgccga actggcgcca | 840 |
| cccgccgatc tggcacccgc gtccgccgac ctggcgccac ccgcgcccgc cgacctggcg | 900 |
| ccacccgcgc ccgccgaact ggccgcaccc gcgccgccg acctggcacc accgctgcg | 960 |
| gtgaacgagc aaaccgcgcc gggcgatcag ccgccacag ctccaggcgg cccggttggc | 1020 |
| cttgccaccg atttggaact ccccgagccc gaccccaac cagctgacgc accgccgccc | 1080 |

```
ggcgacgtca ccgaggcgcc cgccgaaacg ccccaagtct cgaacatcgc ctatacgaag      1140
aagctgtggc aggcgattcg ggcccaggac gtctgcggca acgatgcgct ggactcgctc      1200
gcacagccgt acgtcatcgg ctga                                             1224

<210> SEQ ID NO 83
<211> LENGTH: 504
<212> TYPE: DNA
<213> ORGANISM: Mycobacterium tuberculosis

<400> SEQUENCE: 83
atgtccggac accgcaagaa ggcaatgctc gccttggcgg ctgcgtcgct ggcagcgacg        60
ctggccccga acgcagtcgc ggccgcagaa ccgtcgtgga acgggcagta cctcgtgacg       120
ttgtctgcca acgcgaaaac cggcaccagc atggcggcca accggccaga gtatccacac       180
aaagcgaact acacgttcag ctcgcgctgc gcgtccgatg tctgcattgc caccgtggtc       240
gacgctccgc caccaaaaaa cgagttcatc ccgcggccaa tcgaatacac ctggaatggg       300
actcaatggg tacgggagat cagctggcaa tgggactgcc tgctacccga cggcacaatc       360
gaatatgccc cagccaaatc gatcacggcc tacacgcccg gtcagtacgg aatcctcacc       420
ggcgtctttc ataccgatat cgccagcggc acgtgtaaag gcaatgtcga catgccagtg       480
tcggccaaac cgatcgttgg ctga                                             504

<210> SEQ ID NO 84
<211> LENGTH: 684
<212> TYPE: DNA
<213> ORGANISM: Mycobacterium tuberculosis

<400> SEQUENCE: 84
atgcgttatc tgatagcgac cgcagtgctc gttgctgtgg tcctggtggg ctggccggcg        60
gctggtgcgc cgccgtcatg cgccggcctg ggcggcactg tgcaggccgg ccagatctgc       120
catgtgcacg cctcgggccc taagtacatg ctggatatga catttcctgt cgactatccc       180
gaccagcagg cgctgaccga ctacatcacg caaaaccgcg acgggttcgt caacgtcgcg       240
caggggtccc cgctgcgaga ccagccctac caaatggacg ccaccagcga acagcacagc       300
tccggccagc cgccgcaggc cacccgcagc gtagtgctca aattcttcca ggacctcggt       360
ggggcacatc cgtccacctg gtacaaggcc ttcaactaca acctcgcgac ctcgcagccc       420
atcaccttcg acacgttgtt cgtgcccggc accacgccac tggacagcat ctaccccatc       480
gttcagcgcg agctggcacg tcagaccggt ttcggtgccg cgatattgcc ttcgaccggc       540
ctcgacccgg ctcactacca gaactttgct atcaccgacg acagtctgat tttctacttc       600
gcccagggtg agctgctgcc gtcgtttgtc ggcgcttgcc aagcccaggt gccgcgcagc       660
gccattccgc cgctggcaat ctaa                                             684

<210> SEQ ID NO 85
<211> LENGTH: 519
<212> TYPE: DNA
<213> ORGANISM: Mycobacterium tuberculosis

<400> SEQUENCE: 85
ttgaagaacg cccgtacgac gctcatcgcc gccgcgattg ccgggacgtt ggtgaccacg        60
tcaccagccg gtatcgccaa tgccgacgac gcgggcttgg acccaaacgc cgcagccggc       120
ccggatgccg tgggctttga cccgaacctg ccgccggccc cggacgctgc accgtcgat       180
```

```
actccgccgg ctccggagga cgcgggcttt gatcccaacc tcccccgcc gctggccccg    240 gacttcctgt ccccgcctgc ggaggaagcg cctcccgtgc ccgtggccta cagcgtgaac    300
tgggacgcga tcgcgcagtg cgagtccggt ggaaactggt cgatcaacac cggtaacggt    360
tactacggcg gcctgcggtt caccgccggc acctggcgtg ccaacggtgg ctcggggtcc    420
gcggccaacg cgagccggga ggagcagatc cgggtggctg agaacgtgct gcgttcgcag    480
ggtatccgcg cctggccggt ctgcggccgc cgcggctga                           519

<210> SEQ ID NO 86
<211> LENGTH: 1527
<212> TYPE: DNA
<213> ORGANISM: Mycobacterium tuberculosis

<400> SEQUENCE: 86
atgagcacca tcttcgacat ccgcagcctg cgactgccga actgtctgc aaaggtagtg     60 gtcgtcggcg ggttggtggt ggtcttggcg gtcgtggccg ctgcggccgg cgcgcggctc    120
taccggaaac tgactaccac taccgtggtc gcgtatttct ctgaggcgct cgcgctgtac    180
ccaggagaca aagtccagat catgggtgtg cgggtcggtt ctatcgacaa gatcgagccg    240
gccggcgaca agatgcgagt cacgttgcac tacagcaaca ataccaggt gccggccacg     300 gctaccgcgt cgatcctcaa ccccagcctg gtggcctcgc gcaccatcca gctgtcaccg    360
ccgtacaccg gcggcccggt cttgcaagac ggcgcggtga tcccaatcga gcgcacccag    420
gtgcccgtcg agtgggatca gttgcgcgat tccatcaatg ggatcctccg ccagctcggc    480
ccgacggagc ggcagccgaa ggggccgttc ggcgacctca tcgaatcggc cgcggacaac    540
ctggccggca agggcaggca gctcaacgaa acgctgaaca gtttgtcgca ggcgttgacc    600
gcgctgaacg agggccgggg agacttcgtt gcgatcacgc gaagcctggc gctatttgtc    660
agcgcgctct accagaatga tcaacagttc gttgcgctca cgaaaaacct tgccgagttc    720
accgactggt tcaccaaatc cgaccatgac ttggccgaca cggtggaacg gatcgacgac    780
gttctcggca ccgtccgaaa gttcgtgagc gacaacagat ccgtgctggc tgccgatgtc    840
aacaacctcg ccgacgcgac cactacacta gtgcaacccg agccgcggga cggtctggaa    900
accgcgttgc acgtgttgcc gacctacgcc agcaacttca acaacctta ctatccactg     960 cacagctctc tggtgggcca gttcgtgttc cccaacttcg cgaacccaat tcagctcatt    1020
tgcagcgcta ttcaggccgg cagccgactc ggctatcagg aatccgccga gctgtgcgcg    1080
cagtacttgg caccggttct ggacgctctc aagttcaatt acttgccgtt cggctcaaac    1140
ccgttcagtt cggcggccac tttgcccaag gaggtggctt actccgagga gcggctccgc    1200
ccgccgcccg ggtacaagga caccactgtc ccagggatct tctcgcggga cacaccgttt    1260
tcacacggca accatgaacc gggctgggtc gttgcgcccg ggatgcaggg tatgcaggtt    1320 cagccgtta ccgcgaacat gctcaccccg gaatcgctgg cagagctgct gggtggtccg     1380
gatattgccc ccccgccgcc gggaaccaac ttgcccggac cgccgaatgc gtatgacgag    1440
tccaatccgt tgccgccgcc gtggtacccg cagcccgcgt ccctcccggc tgcgggcgcc    1500
acaggacagc caggcccggg ccagtga                                        1527

<210> SEQ ID NO 87
<211> LENGTH: 693
<212> TYPE: DNA
<213> ORGANISM: Mycobacterium tuberculosis

<400> SEQUENCE: 87
```

-continued

```
atgaaacgca gcatgaaaag cggctccttc gcgatcggtc tggcaatgat gctcgccccg     60
atggtggccg cgcccggtct tgcggccgca gacccggcca cgcggccggt ggattatcaa    120
cagatcaccg acgtcgtgat cgcgcgcggg ctgtcgcagc gcggcgtgcc gttctcctgg    180
gccggcggcg gcatcagcgg ccccacgcgc ggcaccggta ccggcatcaa caccgtcggg    240
ttcgacgcct ccggtttgat ccagtacgcc tatgccggtg ccgggctaaa gctgccgcgt    300
tcttccggcc agatgtacaa ggttgggcaa aaggtcctgc cgcagcaagc gcgcaagggc    360
gacctgatct tctacggccc cgaaggcacg caaagcgtcg cgttatacct cgggaagggc    420
cagatgctgg aggtgggcga cgtcgtccag gtttcgccgg tgcgcaccaa cggcatgacg    480
ccttacctgg tccgggttct cgggacccag ccgacgcccg tccaacaggc gccggtccag    540
ccagcgccgg tccagcaagc gcccgtccag caagcgcccg tccaacaggc gcccgtccaa    600
caggcgccgg tccaacaggc gccggtccag caagcgcccg tccagcaagc gcccgtccag    660
ccgcctccct tcggcaccgc gcgctcacgc taa                                 693
```

<210> SEQ ID NO 88
<211> LENGTH: 336
<212> TYPE: DNA
<213> ORGANISM: Mycobacterium tuberculosis

<400> SEQUENCE: 88

```
atgttcactc gccgtttcgc cgcctccatg gttggcacca ccttgactgc cgctactttg     60
ggcctggccg cactcggctt cgccgggacc gccagcgcaa gctcgaccga cgaagcgttc    120
ctcgcgcagc tgcaggcgga cgggatcact ccgccgagcg cagcgcgcgc catcaaggac    180
gcgcacgccg tctgcgacgc cctcgacgag ggtcactcgg ccaaagcggt catcaaggcg    240
gtggccaagg cgaccggtct gagcgccaag ggcgccaaga cgttcgccgt tgacgccgcg    300
tcggcctact gcccgcagta cgtgacctcg agctaa                              336
```

<210> SEQ ID NO 89
<211> LENGTH: 1563
<212> TYPE: DNA
<213> ORGANISM: Mycobacterium tuberculosis

<400> SEQUENCE: 89

```
atggcggcca tgtggcgccg cagaccgttg agctcggcgc tgctgtcctt cgggttgctg     60
ctcggcggac tgcccctagc agcgccccccg ttggccggcg cgactgaaga acccggcgcc   120
ggccaaaccc cgggtgcgcc ggtcgtggcg ccgcaacaga gttggaacag ctgccgcgag    180
ttcatcgccg acaccagcga aattcgcact gcacgctgcg cgacggtgtc cgtccccgtc    240
gactacgacc aacccggtgg gacacaagcg aagttggcgg tgatccgcgt ccccgcgacg    300
ggacagcgat tcggagcact gctggtcaat cctgggggac ccggggcgtc ggcggtcgac    360
atggtcgccg ctatggcacc cgcgatcgcc gacaccgaca ttctccgcca cttcgacctg    420
gtgggcttcg acccgagagg ggtcggccac tcgacccctg cgttgcggtg tcgcaccgac    480
gccgagttcg acgcgtaccg gcgcgatccg atggccgact acagtccggc cggtgtcacc    540
cacgtcgaac aggtctaccg gcagttggcc caggactgtg ttgaccggat gggcttcagc    600
ttcttggcca atatcggtac cgcgtccgtc gcacgggaca tggacatggt tcgccaagcg    660
ttaggtgacg atcagatcaa ctacctcgga tacagctacg gcaccgagtt gggcaccgct    720
tacctggaac ggttcggtac tcatgtgcgg gcgatggtcc tcgacggcgc tatcgatcca    780
```

```
gccgttagcc caatcgagga aagcatcagc caaatggcgg gatttcagac cgctttcaat    840
gactacgccg ccgactgcgc cgctcgccg gcctgccctc tgggcaccga ctcggcccag     900
tgggtcaacc gctaccacgc cctggttgac ccgctggtgc agaagccggg taagacgtcg    960
gatccacgtg gcctgagcta cgccgacgcg acgacgggca ccatcaacgc gctgtacagc   1020
cctcagcgct ggaagtacct gaccagtggt ctgctggggc tgcagcgcgg cagcgacgcc   1080
ggcgacttgc tggtgcttgc cgacgactat gacggccggg atgcagacgg gcactacagc   1140
aacgaccagg acgcgttcaa cgcggtccgg tgcgtcgatg cgcccacacc ggccgatcca   1200
gcggcctggg tggccgccga ccaacggatc cgtcaggtcg ccccgttcct tagctacggg   1260
cagttcaccg gatccgcccc ccgcgatctg tgcgcgctgt ggccggtgcc ggcaacgtcg   1320
acgccgcacc ccgcggcgcc ggccggggct ggcaaggtcg tcgtggtgtc caccacccac   1380
gacccggcca ctccgtatca gtccggggta gacctggccc gccagctggg cgcaccgctg   1440
atcaccttcg acggcaccca acacactgcg gtgttcgatg caaccagtg tgtggactct    1500 gcggtgatgc actatttct cgacgggacc ttgccgccga cgagtctgcg gtgcgcgccc    1560
tga                                                                  1563

<210> SEQ ID NO 90
<211> LENGTH: 411
<212> TYPE: DNA
<213> ORGANISM: Mycobacterium tuberculosis

<400> SEQUENCE: 90
atgaagacag gcaccgcgac gacgcggcgc aggctgttgg cagtactgat cgccctcgcg     60
ttgccggggg ccgccgttgc gctgctggcc gaaccatcag cgaccggcgc gtcggacccg    120
tgcgcggcca gcgaagtggc gaggacggtc ggttcggtcg ccaagtcgat gggcgactac    180
ctggattcac acccagagac caaccaggtg atgaccgcgg tcttgcagca gcaggtaggg    240
ccggggtcgg tcgcatcgct gaaggcccat tcgaggcga atcccaaggt cgcatcggat     300
ctgcacgcgc tttcgcaacc gctgaccgat cttccgactc ggtgctcgct gccgatcagc    360
ggcctgcagg cgatcggttt gatgcaggcg gtgcaggggcg cccgccggta g            411

<210> SEQ ID NO 91
<211> LENGTH: 447
<212> TYPE: DNA
<213> ORGANISM: Mycobacterium tuberculosis

<400> SEQUENCE: 91
atgtctcggc tgagttccat cctgcgtgcc ggcgcggcat ttctggttct cggcatcgcc     60
gctgcgacat ttccacaaag cgcggcagcc gactccacgg aagactttcc aatacctcgc    120
cggatgatcg caaccacctg cgacgccgaa caatatctgg cggcggtgcg ggataccagt    180
ccggtgtact accagcggta catgatcgac ttcaacaacc atgcaaacct tcagcaagcg    240
acgatcaaca aggcgcactg gttcttctcg ctgtcaccgg cggagcgccg agactactcc    300
gaacactttt acaatggcga tccgctgacg tttgcctggg tcaatcacat gaaaatcttc    360
ttcaacaaca agggcgtcgt cgctaaaggg accgaggtgt gcaatggata cccagccggc    420
gacatgtcgg tgtggaactg ggcctaa                                        447

<210> SEQ ID NO 92
<211> LENGTH: 435
<212> TYPE: DNA
<213> ORGANISM: Mycobacterium tuberculosis
```

<400> SEQUENCE: 92

```
gtgaccaagc gcacaataac tcccatgacg tcgatgggtg atctcttggg acctgagcca      60
atcctgttgc ctggcgacag cgacgccgaa gcggagctgc ttgccaacga aagtccgagc     120
atcgtcgcgg ccgcgcatcc gtcggcgtcg gtcgcctggg cggtgctcgc cgaaggggcg     180
ctggccgacg acaagaccgt cacggcctac gcatacgcgc gtaccgggta ccaccgcggc     240
ctggaccagc tgcgccgcca tggctggaag ggcttcggcc cggtgccgta ttcccaccag     300
cccaaccggg gtttcctacg gtgtgtggcg cgctggcgc gcgccgcagc cgctatcggc      360
gagaccgacg agtatggacg ctgcctggat ctgcttgacg actgtgaccc cgcggcccgt     420
ccggcgcttg ggctc                                                     435
```

<210> SEQ ID NO 93
<211> LENGTH: 429
<212> TYPE: DNA
<213> ORGANISM: Mycobacterium tuberculosis

<400> SEQUENCE: 93

```
gtgatcatcc ctgacatcaa tctgctgctc tacgcggtca tcaccggatt cccgcagcac      60
cggcgcgcgc atgcgtggtg gcaagacacc gtcaacggcc acaccgtat cgggctgacg      120
tatccggcgt tgttcggggtt cctacggatc gccaccagtg cccgcgtgct cgccgcgcca    180
ctgccaaccg cggatgcgat cgcctatgtg cgcgagtggc tttcgcagcc gaacgtggac     240
ctactcacgg cgggtccgcg ccacctggac atcgcgttgg gcctgctcga caagctcggc    300
acagccagcc acctaaccac cgatgtgcaa ctggccgcct acggcatcga atacgacgcc    360
gagatccatt ccagtgacac cgactttgcc cgattcgccg atctgaagtg gaccgacccg    420
ttgcgcgaa                                                            429
```

<210> SEQ ID NO 94
<211> LENGTH: 513
<212> TYPE: DNA
<213> ORGANISM: Mycobacterium tuberculosis

<400> SEQUENCE: 94

```
ttgactgatc cgcgccacac cgttcgaatc gctgtcggag ctaccgcgct cggcgtgtcg      60
gcactcgggg caactctgcc ggcctgctcc gcacacagcg ggccgggttc tccccccagt    120
gcgccgtcag ctcccgcggc cgcgaccgtc atggtagagg acatacgca cacaatttcc     180
ggagtggtcg agtgccgcac ctcgccagcg gtaaggacgg cgacgccgtc ggagtcgggg    240
actcaaacta cacggttaa cgcacacgac gattcggcct cggtgacact gtccctgtcc     300
gactccacgc ccccagacgt caatggtttt ggtatctccc ttaaaatcgg aagcgtcgac    360
taccagatgc cctaccagcc ggttcagtcc ccaactcagg tcgaagcgac caggcagggc   420
aagagttaca cactgaccgg gacgggtcac gcggtgatcc cgggccaaac cggcatgcgt   480
gagctgccgt tcggggtaca tgtaacctgt ccg                                513
```